(12) United States Patent
Davies

(10) Patent No.: US 8,738,124 B2
(45) Date of Patent: May 27, 2014

(54) ELECTRICAL BIOIMPEDANCE ANALYSIS AS A BIOMARKER OF BREAST DENSITY AND/OR BREAST CANCER RISK

(75) Inventor: Richard J. Davies, Saddle River, NJ (US)

(73) Assignee: Epi-Sci, LLC, Saddle River, NJ (US)

( * ) Notice: Subject to any disclaimer, the term of this patent is extended or adjusted under 35 U.S.C. 154(b) by 75 days.

(21) Appl. No.: 12/316,032

(22) Filed: Dec. 8, 2008

(65) Prior Publication Data

US 2009/0171236 A1 Jul. 2, 2009

Related U.S. Application Data

(60) Provisional application No. 61/007,128, filed on Dec. 11, 2007.

(51) Int. Cl.
*A61B 5/05* (2006.01)
(52) U.S. Cl.
USPC .......................... 600/547; 600/554; 702/137
(58) Field of Classification Search
USPC ......... 600/300, 547, 587, 372, 382, 384, 386, 600/388, 393, 546, 549, 554; 702/137, 155; 607/1, 2, 3, 50, 51, 52
See application file for complete search history.

(56) References Cited

U.S. PATENT DOCUMENTS

| | | | |
|---|---|---|---|
| 3,786,801 A | 1/1974 | Sartorius | |
| 3,949,736 A | 4/1976 | Vrana et al. | |
| 4,729,385 A | 3/1988 | Juncosa et al. | |
| 4,955,383 A | 9/1990 | Faupel | |
| 5,099,844 A | 3/1992 | Faupel | |
| 5,109,849 A | 5/1992 | Goodman et al. | |
| 5,345,935 A | 9/1994 | Hirsch et al. | |
| 5,417,222 A | 5/1995 | Dempsey et al. | |
| 5,697,369 A | 12/1997 | Long, Jr. et al. | |
| 5,722,404 A | 3/1998 | Lundback | |
| 5,810,742 A | 9/1998 | Pearlman | |

(Continued)

FOREIGN PATENT DOCUMENTS

| | | |
|---|---|---|
| WO | 98/23204 A1 | 6/1998 |
| WO | 2007017634 A2 | 2/2007 |

OTHER PUBLICATIONS

Dua et al., Detection of basal cell carcinoma using electrical Impedance and neural networks; Biomedical Engineering, IEEE Transactions on; vol. 51, Issue 1, Jan. 2004 pp. 66-71.
Duric, N., et al. Med Phys 34.2 (2007): 773-85.

(Continued)

*Primary Examiner* — Max Hindenburg
*Assistant Examiner* — Renee Danega
(74) *Attorney, Agent, or Firm* — Lerner, David, Littenberg, Krumholz & Mentlik, LLP

(57) ABSTRACT

Methods and systems are provided for the noninvasive measurement of the subepithelial impedance of the breast and for assessing the risk that a substantially asymptomatic female patient will develop or be at substantially increased risk of developing proliferative or pre-cancerous changes in the breast, or may be at subsequent risk for the development of pre-cancerous or cancerous changes. A plurality of electrodes are used to measure subepithelial impedance of parenchymal breast tissue of a patient at one or more locations and at least one frequency, particularly moderately high frequencies. The risk of developing breast cancer is assessed according to measured and expected or estimated values of subepithelial impedance for the patient and according to one or more experienced-based algorithms. Devices for practicing the disclosed methods are also provided.

14 Claims, 11 Drawing Sheets

(56) References Cited

U.S. PATENT DOCUMENTS

| | | | |
|---|---|---|---|
| 5,906,208 | A | 5/1999 | Ishikawa |
| 6,026,322 | A | 2/2000 | Korenman et al. |
| 6,122,544 | A | 9/2000 | Organ |
| 6,135,953 | A | 10/2000 | Carim |
| 6,138,044 | A | 10/2000 | Svedman |
| 6,251,681 | B1 | 6/2001 | Davies et al. |
| 6,308,097 | B1 | 10/2001 | Pearlman |
| 6,314,315 | B1 | 11/2001 | Hung |
| 6,328,735 | B1 | 12/2001 | Curley et al. |
| 6,363,275 | B1 | 3/2002 | Kaiser |
| 6,389,305 | B1 | 5/2002 | Deban et al. |
| 6,456,865 | B2 | 9/2002 | Samson |
| 6,471,660 | B1 | 10/2002 | Covington |
| 6,496,725 | B2 | 12/2002 | Kamada et al. |
| 6,641,604 | B1 | 11/2003 | Adelman et al. |
| 6,773,418 | B1 | 8/2004 | Sharrow et al. |
| 6,823,203 | B2 | 11/2004 | Jordan |
| 6,887,239 | B2 | 5/2005 | Elstrom et al. |
| 6,898,303 | B2 | 5/2005 | Armato, III et al. |
| 6,922,586 | B2 | 7/2005 | Davies |
| 7,050,847 | B2 | 5/2006 | Ollmar et al. |
| 7,223,239 | B2 | 5/2007 | Schulze et al. |
| 2001/0051774 | A1 | 12/2001 | Littrup et al. |
| 2003/0010987 | A1 | 1/2003 | Banin et al. |
| 2003/0109871 | A1 | 6/2003 | Johnson et al. |
| 2003/0216661 | A1 | 11/2003 | Davies |
| 2004/0253652 | A1 | 12/2004 | Davies |
| 2005/0059928 | A1 | 3/2005 | Larsson |
| 2006/0122653 | A1 | 6/2006 | Bradley et al. |
| 2006/0173352 | A1 | 8/2006 | Lilge et al. |
| 2006/0241514 | A1* | 10/2006 | Davies ............... 600/547 |
| 2007/0265512 | A1 | 11/2007 | Ollmar et al. |

OTHER PUBLICATIONS

Elble RC, Pauli BU. Tumor Suppression by a Proapoptotic Calcium-Activated Chloride Channel in Mammary Epithelium, The Journal of Biological Chemistry, Nov. 2001, pp. 40510-40517, vol. 276, No. 44, The American Society for Biochemistry and Molecular Biology.

Emtestam L, Ollmar S. Electrical Impedance Index in Human Skin: Measurements After Occlusion, In 5 Anatomical Regions and in Mild Irritant Contact Dermatitis. Contact Dermatitis Environmental and Occupational Dermatitis, Feb. 1993, pp. 104-108, vol. 28, No. 2, RJG Rycroft, London, England.

Ernst M, Adam G. Regulation of Passive Potassium Transport of Normal and Transformed 3T3 Mouse Cell Cultures by External Calcium Concentration and Temperature. Journal of Member Biology, 1981; pp. 155-172, vol. 61, No. 3, Springer-Verlag New York Inc.

Farinha, BS, et al., Skin Impedance Reduction for Electrophysiology Measurements Using Ultrasonic Skin Permeation, Biomedical Instrumentation & Technology, Jan./Feb. 2006, pp. 72-77.

Faupel M, Vanel D, Barth V, Davies R, Fentiman IS, Holland R et al. Electropotential Evaluation as a New Technique for Diagnosing Breast Lesions. European Journal of Radiology, Jan. 1997, pp. 33-38. vol. 24, No. 1, Elsevier.

Fehlmann M, Canivet B, Freychet P. Epidermal Growth Factor Stimulates Monovalent Cation Transport in Isolated Rat Hepatocytes, Biochemical and Biophysical Research Communications, May 1981, pp. 254-260, vol. 100, No. 1, Academic Press Inc.

Felber SM, Brand MD. Concanavalin A Causes an Increase in Sodium Permeability and Intracellular Sodium Content of Pig Lymphocytes, The Biochemical Journal, Mar. 1983, pp. 893-897, vol. 210, No. 3, The Biochemical Society, London.

Foster KR, Schwan HP. Dielectric Properties of Tissues and Biological Materials: A Critical Review. Critical Reviews in Biomedical Engineering, 1989, pp. 25-104 vol. 17, Issue 1, CRC Press, England.

Foster, Kenneth R., Bioimpedance as Medical Technology: What Does it Take to Succeed; University of Pennsylvania, Philadelphia, PA.

Fraser GM, Portnoy M, Bleich M, Ecke D, Niv Y, Greger R et al. Characterization of Sodium and Chloride Conductances in Preneoplastic and Neoplastic Murine Colonocytes, Pflugers Archive European Journal of Physiology, Nov. 1997, pp. 801-808, vol. 434, No. 6, Springer.

Fraser SP, Grimes JA, Djamgoz MB. Effects of Voltage-Gated Ion Channel Modulators on Rat Prostatic Cancer Cell Proliferation: Comparison of Strongly and Weakly Metastatic Cell Lines, The Prostate, 2000, pp. 61-76, vol. 44, No. 1, Wiley-Liss, Inc.

Fukuda M, Shimizu K, Okamoto N, Arimura T, Ohta T, Yamaguchi S et al. Prospective Evaluation of Skin Surface Electropotentials in Japanese Patients With Suspicious Breast Lesions, Japanese Journal of Cancer Research, Oct. 1996, pp. 1092-1096, vol. 87, No. 10, Elsevier Science, Ltd., Ireland and Business Center for Academic Societies, Japan.

Funkhouser WK, Pilch YH, Davies RJ. The Electrophysiologic Changes Associated with Premalignancy in Colon Carcinogenesis, Federation Proceedings, Mar. 1986, p. 742, vol. 45, No. 4, Federation of American Societies for Experimental Biology.

Glide, C., et al. Med Phys 34 (2007): 744-53.

Glide-Hurst, C. K., et al. Medical Physics 34 (2007): 4491-98.

Goller DA, Weidema WF, Davies RJ. Transmural Electrical Potential Difference as an Early Marker in Colon Cancer. Archives of Surgery, Mar. 1986, pp. 345-350, vol. 121, No. 3, The American Medical Association, USA.

Gonzalez-Correa CA, Brown BH, Smallwood RH, Kalia N, Stoddard CJ, Stephenson TJ et al. Assessing the Conditions for In Vivo Electrical Virtual Biopsies in Barrett's Oesophagus, Medical & Biological Engineering & Computing, Jul. 2000, pp. 373-376, vol. 38, No. 4.

Gonzalez-Correa CA, Brown BH, Smallwood RH, Kalia N, Stoddard CJ, Stephenson TJ et al. Virtual Biopsies in Barrett's Esophagus Using an Impedance Probe, Annals of New York Academy of Sciences, 1999, pp. 313-321, vol. 873, The New York Academy of Sciences, New York, NY, USA.

Goodwin, P. J., et al. Am J Epidemiol 127 (1988): 1097-108.

Gorecki J, Dolan EJ, Tasker RR, Kucharczyk W. Correlation of CT and MR With Impedance Monitoring and Histopathology in Stereotactic Biopsies, The Canadian Journal of Neurological Sciences, May 1990, pp. 184-189, vol. 17, No. 2.

Graham, S. J., et al. Br J Cancer 73 (1996): 162-68.

Gram, I. T., et al. Breast Cancer Res 7 (2005): R854-R861.

Grimes JA, Djamgoz MB. Electrophysiological Characterization of Voltage-Gated Na+ Current Expressed in the Highly Metastatic Mat-LyLu Cell Line of Rat Prostate Cancer, Journal of Cellular Physiology, Apr. 1998, pp. 50-58, vol. 175, No. 1, Wiley-Liss, Inc.

Grimes JA, Fraser SP, Stephens GJ, Downing JE, Laniado ME, Foster CS et al. Differential Expression of Voltage-Activated Na+ currents in Two Prostatic Tumour Cell Lines: Contribution to Invasiveness In Vitro, FEBS Letters, Aug. 1995, pp. 290-294, vol. 369, No. 2-3, Elsevier on Behalf of the Federation of European Biochemical Societies.

Gutierrez AA, Arias JM, Garcia L, Mas-Oliva J, Guerrero-Hernandez A. Activation of a Ca2+-Permeable Cation Channel by Two Different Inducers of Apoptosis in a Human Prostatic Cancer Cell Line, The Journal of Physiology, May 1999, pp. 95-107, vol. 517, Pt 1, The Physiological Society.

Hartman, Keith et al., "Volumetric assessment of breast tissue composition from FFDM images", IWDM 2008. Ed. E.A. Krupinski (Ed.). Berlin Heidelberg: Springer-Verlag, 2008. 33-39.

Hay JG, Geddes DM. Transepithelial Potential Difference in Cystic Fibrosis, The Journal of the British Thoracic Society, Jul. 1985, pp. 493-496, vol. 40, No. 7, British Medical Association, London, England.

Hebestreit A, Kersting U, Basler B, Jeschke R, Hebestreit H. Exercise Inhibits Epithelial Sodium Channels in Patients With Cystic Fibrosis, American Journal of Respiratory and Critical Care Medicine, Jul. 2001, pp. 443-446, vol. 164, No. 3.

Highnam, R. P., et al. Mammographic Image Analysis (1999).

Hope et al., Technology review: The use of electrical impedance scanning in the detection of breast cancer, Breast Cancer Res 2004, 6:69-74.

Huang Y, Rane SG. Single Channel Study of a Ca(2+)-31 Activated K+ Current Associated With Ras-Induced Cell Transformation, The Journal of Physiological Society, 1993, pp. 601-618, vol. 461, Cambridge University Press.

(56) References Cited

OTHER PUBLICATIONS

Huo, Z., et al. Med Phys 27 (2000): 4-12.
Hülser DF, Frank W. Stimulation of Embryonic Rat Cell in Culture by a Protein Fraction Isolated From Fetal Calf Serum, Publishing House of the Periodical for Nature Research, Jul. 1971, pp. 1045-1048, vol. 26b, No. 7.
International Search Report, PCT/US2008/13567, dated May 22, 2009.
Jhappan, C., Geiser, A.G., Kordon, E.C., Bagheri, D., Hennighausen, L., Roberts, A.B., Smith, G.H., and Merlino, G. EMBO J. 1993 12:1835-1845. [6] Stojadinovic A, Nissan A, Gallimidi Z, et.al. J Clin Oncol Apr. 20, 2005; 23 (12):2703-15.
Jossinet J, Schmitt M. A Review of Parameters for the Bioelectrical Characterization of Breast Tissue, Annals of the New York Academy of Sciences, 1999, pp. 30-41, vol. 873, The New York Academy of Sciences, New York, NY.
Jossinet J. The Impedivity of Freshly Excised Human Breast Tissue, Physiological Measurement, Feb. 1998, pp. 61-75, vol. 19, No. 1, Institute of Physics Publishing.
Jossinet J. Variability of Impedivity in Normal and Pathological Breast Tissue, Medical & Biological Engineering & Computing, Sep. 1996, pp. 246-350, vol. 34, No. 5.
Kapural L, Fein A. Changes in the Expression of Voltage-Gated K+ Currents During Development of Human Megakaryocytic Cells, Biochimica et Biophysica Acta 1997, pp. 319-328; vol. 1326, No. 2, Elsevier, USA.
Karssemeijer, N. Phys Med Biol 43 (1998): 365-78.
Kaufhold, J., et al. Med Phys 29 (2002): 1867-80.
Khan et al., "Correlation of mammographic breast density with Ki-67 expression in benign breast epithelial cells obtained by random periareolar fine needle aspiration of high risk women", Journall of Clinical Oncology, vol. 24, No. 18S (2006): 1011.
Kiefer H, Blume AJ, Kaback HR. Membrane Potential Changes During Mitogenic Stimulation of Mouse Spleen Lymphocytes, Proceedings of the National Academy of Sciences, of the United States of America, Apr. 1980, pp. 2200-2204, vol. 77, No. 4.
Kim JA, Kang YS, Jung MW, Lee SH, Lee YS. Involvement of Ca2+ Influx in the Mechanism of Tamoxifen-Induced Apoptosis in HepG2 Human Hepatoblastoma Cells, Cancer Letters, Dec. 1999, pp. 115-123, vol. 147, No. 1-2, Elsevier.
Kim JA, Kang YS, Lee YS. Involvement of K(+)-Cl(−)-cotransport in the Apoptosis Induced by N- Ethylmaleimide in HepG2 Human Hepatoblastoma Cells, European Journal of Pharmacology, Apr. 2001, pp. 1-5, vol. 418, Nos. 1-2, Elsevier.
Kimura S, Morimoto T, Uyama T, Monden Y, Kinouchi Y, Iritani T. Application of Electrical Impedance Analysis for Diagnosis of a Pulmonary Mass, Chest, 1994, pp. 1679-1682, vol. 105, No. 6, Official Publication of American College of Chest Physicians.
Klifa, C., et al. IEMBS '04: 26th Annual International Conference of the IEEE: San Francisco, CA; Sep. 1-4, 2004 1 (2004): 1667-70.
Klimatcheva E, Wonderlin WF. An ATP-Sensitive K(+) Current That Regulates Progression Through Early G1 Phase of the Cell Cycle in MCF-7 Human Breast Cancer Cells, The Journal of Membrane Biology, Sep. 1999, pp. 35-46, vol. 171, No. 1, Spinger.
Knowles M, Gatzy J, Boucher R. Increased Bioelectric Potential Difference Across Respiratory Epithelia in Cystic Fibrosis, New England Journal of Medicine, Dec. 1981, pp. 1489-1495, vol. 305, No. 25, Massachusets Medical Society.
Koch KS, Leffert HL. Growth Control of Differentiated Adult Rat Hepatocytes in Primary Culture, Annals of the New York Academy of Sciences, 1980, pp. 111-127, vol. 349, The New York Academy of Sciences, New York, USA.
Kopans, D. B. Radiology 246.2 (2008): 348-53.
Kristt D, Winston GJ, Mellov MM, Veltman V, Koren R. Patterns of Proliferative Changes in Crypts Bordering Colonic Tumors: Zonal Histology and Cell Cycle Marker Expression. Pathology Oncology Research, 1999; pp. 297-303, vol. 5, No. 4.
Lackermeier AH, McAdams ET, Moss GP, Woolfson AD. In Vivo AC Impedance Spectroscopy of Human Skin. Theory and Problems in Monitoring of Passive Percutaneous Drug Delivery. Annals of the New York Academy of Sciences, 1999, pp. 197-213, vol. 873.
Lai CN, Gallick GE, Arlinghaus RB, Becker FF. Temperature-Dependent Transmembrane Potential Changes in Cells Infected With a Temperature-Sensitive Moloney Sarcoma Virus, Journal of Cellular Physiology, Oct. 1984, pp. 139-142, vol. 121, No. 1, Alan R. Liss, Inc.
Laniado ME, Fraser SP, Djamgoz MB. Voltage-Gated K(+) Channel Activity in Human Prostate Cancer Cell Lines of Markedly Different Metastatic Potential: Distinguishing Characteristics of PC-3 and LNCaP cells, The Prostate, 2001, pp. 262-274, vol. 46, No. 4, Wiley-Liss, Inc.
Laniado ME, Lalani EN, Fraser SP, Grimes JA, Bhangal G, Djamgoz MB et al. Expression and Functional Analysis of Voltage-Activated Na+ channels in Human Prostate Cancer Cell Lines and Their Contribution to Invasion In Vitro, The American Journal of Pathology, Apr. 1997, pp. 1213-1221, vol. 150, No. 4, American Society for Investigative Pathology.
Lee, N. A., et al. AJR Am J Roentgenol 168 (1997): 501-06.
Leffert HL, Koch KS. Ionic Events at the Membrane Initiate Rat Liver Regeneration. Ann the New York Academy of Sciences, 1980, pp. 201-215, vol. 339, New York, USA.
Li, H., et al. "Computerized analysis of mammographic parenchymal patters for assessing breast cancer risk" effect of ROI size and location, Medical Physics 31 (2004): 549-555.
Li, H., et al. Acad Radiol 12 (2005): 863-73.
Liu MP, Handschumacher RE. Tamoxifen Induces Na+-Dependent Uridine Transport and Dome Formation in a Human Breast Tumor Cell Line, The Cancer Journal from Scientific American, Aug. 1995, pp. 210-214, vol. 1, No. 3.
Loewenstein WR. Junctional Cell-To-Cell Communication and Growth Control, Annals of the New York Academy of Sciences, 1980, pp. 39-45, vol. 339, The New York Academy of Sciences, New York, USA.
Loewenstein WR. Junctional Intercellular Communication and the Control of Growth, Biochimica et Biophysica Acta , Feb. 1979, pp. 1-65, vol. 560, No. 1, Elsevier/North-Holland.
Macara IG. Oncogenes, ions, and Phospholipids, American Journal of Physiology, Jan. 1985, pp. C3-11, vol. 248, No. 1 Pt 1, The American Physiological Society.
Magnin et al., "Mammographic texture analysis: an evaluation of risk for developing breast cancer", Optical Engineering 25 (1986): 780-784.
Malich A, Boehm T, Facius M, Freesmeyer MG, Fleck M, Anderson R et al. Differentiation of Mammographically Suspicious Lesions: Evaluation of Breast Ultrasound, MRI Mammography and Electrical Impedance Scanning as Adjunctive Technologies in Breast Cancer Detection, Clinical Radiology, Apr. 2001, pp. 278-283, vol. 56, No. 4, WB Saunders Company Ltd.
Malich A, Fritsch T, Anderson R, Boehm T, Freesmeyer MG, Fleck M et al. Electrical Impedance Scanning for Classifying Suspicious Breast Lesions: First Results, European Radiology, 2000, pp. 1555-1561, vol. 10, No. 10, Springer-Verlag.
Malich A, Fritsch T, Mauch C, Boehm T, Freesmeyer M, Fleck M et al. Electrical impedance Scanning: A New Technique in the Diagnosis of Lymph Nodes in Which Malignancy Is Suspected on Ultrasound, British Journal of Radiology, 2001, pp. 42-47, vol. 74, No. 877.
Marino AA, Iliev IG, Schwalke MA, Gonzalez E, Marler KC, Flanagan CA. Association Between Cell Membrane Potential and Breast Cancer, Tumour Biology, 1994, pp. 82-89, vol. 15, No. 2.
Marino AA, Morris DM, Schwalke MA, Iliev IG, Rogers S. Electrical Potential Measurements in Human Breast Cancer and Benign Lesions, Tumour Biology, Jan. 1994, pp. 147-152, vol. 15, No. 3, S. Karger.
Martin, K. E., et al. Radiology 240 (2006): 656-65.
McCormack, V. A., et al. Cancer Epidemiol Biomarkers Prev 16 (2007): 1148-54.
Megalooikonomou et al., "Analysis of texture patterns in medical images with an application to breast imaging", Proceedings of SPIE Medical Imaging 2007: Computer-Aided Diagnosis: Feb. 20, 2007; San Diego, CA, USA 6514 (2007): 651421.
Miller et al., "Classification of breast tissue by texture analysis", Image and Vision Computing 10 (1992): 277-282.

(56) References Cited

OTHER PUBLICATIONS

Mitchell, G., et al. Cancer Res 66 (2006): 1866-72.

Moolenaar WH, De Laat SW, Mummery CL, Van Der Saag PT. Na+/H+ Exchange in the Action of Growth Factors. In: Boynton AL, McKeehan WL, Whitfield JF, editors. Ions, Cell Proliferation and Cancer, Academic Press, Inc., 1982, pp. 151-162, New York.

Moolenaar WH, De Laat SW, Van Der Saag PT. Serum Triggers a Sequence of Rapid Ionic Conductance Changes in Quiescent Neuroblastoma Cells, Nature, Jun. 14, 1979, pp. 721-723, vol. 279, No. 5714.

Moolenaar WH, Mummery CL, Van Der Saag PT, De Laat SW. Rapid Ionic Events and the Initiation of Growth in Serum-Stimulated Neuroblastoma Cells, Cell Mar. 1981, pp. 789-798, vol. 23, No. 3.

Moolenaar WH, Tertoolen LG, De Laat SW. The Regulation of Cytoplasmic pH in Human Fibroblasts, The Journal of Biological Chemistry. Jun. 1984, pp. 7563-7569, vol. 259, No. 12, The American Society of Biological Chemists, Inc., USA.

Moolenaar WH, Tsien RY, Van Der Saag PT, De Laat SW. Na+/H+ Exchange and Cytoplasmic Ph in the Action of Growth Factors in Human Fibroblasts. Nature, International Weekly Journal of Science, Aug. 1983, pp. 645-648, vol. 304, No. 5927, MacMillan Journals, Ltd.

Morimoto T, Kimura S, Konishi Y, Komaki K, Uyama T, Monden Yet al. A Study of the Electrical Bio-Impedance of Tumors, Journal of Investigative Surgeries, 1993, pp. 25-32, vol. 6, No. 1, Taylor & Francis, New York, USA.

Morimoto T, Kinouchi Y, Iritani T, Kimura S, Konishi Y, Mitsuyama N et al. Measurement of the Electrical Bio-Impedance of Breast Tumors, European Surgical Research, Apr. 1990, pp. 86-92, vol. 22, No. 2, S. Karger Medical and Scientific Publishers.

Morris AP, Cunningham SA, Benos DJ, Frizzell RA. Cellular Differentiation is Required for cAMP but Not Ca(2+)-dependent Cl-Secretion in Colonic Epithelial Cells Expressing High Levels of Cystic Fibrosis Transmembrane Conductance Regulator, The Journal of Biological Chemistry, Mar. 1992, pp. 5575-5583, vol. 267, No. 8, The American Society for Biochemistry and Molecular Biology.

Nagy IZ, Lustyik G, Nagy VZ, Zarandi B, Bertoni-Freddari C. Intracellular Na+:K+ Ratios in Human Cancer Cells as Revealed by Energy Dispersive X-Ray Microanalysis, The Journal of Cell Biology, Sep. 1981, pp. 769-777, vol. 90, No. 3, The Rockefeller University Press, USA.

Nicander I, Ollmar S, Rozell BL, Eek A, Emtestam L. Electrical Impedance Measured to Five Skin Depths in Mild Irritant Dermatitis Induced by Sodium Lauryl Sulphate, British Journal of Dermatology, May 1995, pp. 718-724, vol. 132, No. 5, Blackwell Scientific Publications.

Niemeyer BA, Bergs C, Wissenbach U, Flockerzi V, Trost C. Competitive Regulation of CaT-Like Mediated Ca2+ Entry by Protein Kinase C and Calmodulin, Proceedings of the National Academy of Sciences of the United States of America, Mar. 2001, pp. 3600-3605, vol. 98, No. 6.

Niklason, L. T., et al. Radiology 205 (1997): 399-406.

Nilius B, Bohm T, Wohlrab W. Properties of a Potassium-Selective Ion Channel in Human Melanoma Cells, Pflägers Archive European Journal of Physiology, Nov. 1990, pp. 269-277, vol. 417, No. 3, Springer International.

Nilius B, Wohlrab W. Potassium Channels and Regulation of Proliferation of Human Melanoma Cells, The Journal of Physiology, 1992, pp. 537-548, vol. 445, Cambridge University Press.

O'Donnell ME, Villereal ML. Membrane Potential and Sodium Flux in Neuroblastoma X Glioma Hybrid Cells: Effects of Amiloride and Serum, Journal of Cellular Physiology, Dec. 1982, pp. 405-412, vol. 113, No. 3, Alan R. Liss, Inc.

Ohmine Y, Morimoto T, Kinouchi Y, Iritani T, Takeuchi M, Monden Y. Noninvasive Measurement of the Electrical Bioimpedance of Breast Tumors, Anticancer Research, Jun. 2000, pp. 1941-1946, vol. 20, No. 3B.

Oksiejczuk E, Figaszewski Z. Electrokinetic Potential of Lung Cancer Cells, Rocziniki Akademii Medycznej Bialymstoku, 1997, pp. 340-354, vol. 42, Supplement 1.

Ollmar S, Eek A, Sundstrom F, Emtestam L. Electrical Impedance for Estimation of Irritation in Oral Mucosa and Skin. Medical Progress Technology, Feb. 1995, pp. 29-37, vol. 21. No. 1, Kluwer Academic Publishers.

Ollmar S, Nyren M, Nicander I, Emtestam L. Electrical Impedance Compared With Other Non-Invasive Bioengineering Techniques and Visual Scoring for Detection of Irritation in Human Skin, British Journal of Dermatology, Jan. 1994, pp. 29-36, vol. 130, No. 1, Blackwell Scientific Publications.

Orlando RC, Powell DW, Croom RD, Berschneideri HM, Boucher RC, Knowles MR. Colonic and Esophageal Transepithelial Potential Difference in Cystic Fibrosis, Gastroenterology, Apr. 1989, pp. 1041-1048, vol. 96, No. 4, American Gastroentrological Association.

Ouadid-Ahidouch H, Roudbaraki M, Delcourt P, et.al. Am. J Physiol. Cell Physiol. Jul. 2004;287(1):C125-34.

Owen NE, Villereal ML. Role of Ca2+ in Serum-Stimulated Na+ Influx in Normal and Transformed Cells, American Journal of Physiology, Mar. 1985, pp. C288-C295, vol. 248, No. 3 Pt 1, The American Physiological Society.

Palomares, M. R., et al. Cancer Epidemiol Biomarkers Prey 15 (2006): 1324-30.

Allen DH, Lepple-Wienhues A, Cahalan MD. Ion Channel Phenotype of Melanoma Cell Lines, The Journal of Membrane Biology, 1997, pp. 27-34, vol. 155, No. 1, Springer.

American College of Radiology. Breast Imaging Reporting and Data System (BIRADS) (1993) as in Kopans, D.B., Breast Imaging 2d Ed. (1998) (BIRADS) Lippincott-Raven Publ, Phil.

Balitsky KP, Shuba EP. Resting Potential of Malignant Cells, ACTA, Eighth International Cancer Congress, 1964, pp. 1391-1393, vol. 20, No. 67.

Bernstein JM, Gorfien J, Noble B, Yankaskas JR. Nasal polyposis: Immunohistochemistry and Bioelectrical Findings (A Hypothesis for the Development of Nasal Polyps), The Journal of Allergy and Clinical Immunology, Feb. 1997, pp. 165-175, vol. 99, No. 2, Mosby.

Bernstein JM, Yankaskas JR. Increased Ion transport in Cultured Nasal Polyp Epithelial Cells, Archives of Otolaryngology of Head & Neck Surgery, Sep. 1994, pp. 993-996, vol. 120, No. 9, American Medical Association.

Binggeli R, Cameron Il. Cellular Potentials of Normal and Cancerous Fibroblasts and Hepatocytes, Cancer Research, Jun. 1980, pp. 1830-1835, vol. 40, No. 6.

Blend, R., et al., "Parenchymal patters of the breast defined by real time ultrasound", European Journal of Cancer Prevention 4 (1995): 293-298.

Boone, J., et al., "Computed tomography of the breast: Design, Fabrication, Characterization, and Intial Clinical Testing", Medical Physics, vol. 33, No. 6 (2006): 2185.

Boonstra J, Moolenaar WH, Harrison PH, Moed P, Van Der Saag PT, De Laat SW. Ionic Responses and Growth Stimulation Induced by Nerve Growth Factor and Epidermal Growth Factor in Rat Pheochromocytoma (PC12) cells, The Journal of Cell Biology, Jul. 1983, pp. 92-98, vol. 97, No. 1, The Rockefeller University Press.

Boyd, N. F., et al. N.Engl.J Med 356.3 (2007): 227-36.

Brasitus TA, Dudeja PK, Foster ES. 1,2-Dimethylhydrazine-induced Alterations in Na+—H+ Exchange in Rat Colonic Brush-Border Membrane Vesicles, Biochimica et Biophysica Acta, Mar. 1988, pp. 483-488, vol. 938, No. 3, Elsevier.

Broaddus RR, Wargovich MJ, Castro GA. Early stages of 1,2-dimethylhydrazine-Induced Colon Carcinogenesis Suppress Immune-Regulated Ion Transport of Mouse Distal Colon, Cancer Research, Nov. 1994, pp. 5930-5936, vol. 54, No. 22, Official Journal of the American Association for Cancer Research, USA.

Broggi G, Franzini A. Value of Serial Stereotactic Biopsies and Impedance Monitoring in the Treatment of Deep Brain Tumours, Journal of Neurology Neurosurgery and Psychiatry, May 1981, pp. 397-401, vol. 44, No. 5, British Medical Association, London, England.

Brown BH, Tidy JA, Boston K, Blackett AD, Smallwood RH, Sharp F. Relation Between Tissue Structure and Imposed Electrical Current Flow in Cervical Neoplasia, The Lancet, Mar. 2000, pp. 892-895, vol. 355, No. 9207, The Lancet Publishing Group, Ltd., Elsevier Sciences Ltd.

(56) References Cited

OTHER PUBLICATIONS

Brown BH. Impedance Tomography and Spectroscopy: What can and what will we see? In: Sverre Grimnes, Ørjan G.Martinsen, Heidi Bruvoll, editors. Proceedings XI International Conference on Electrical Bio-Impedance. Oslo, Norway, University of Oslo, 2001: 9-13.
Buist, D. S., et al. Cancer Epidemiol Biomarkers Prev 15 (2006): 2303-06.
Buist, D. S., et al. J Natl Cancer Inst 96 (2004): 1432-40.
Bustin SA, Li SR, Dorudi S. Expression of the Ca2+-Activated Chloride Channel Genes CLCA1 and CLCA2 Is Downregulated in Human Colorectal Cancer, DNA and Cell Biology, Nov. 2001, pp. 331-338, vol. 20, No. 6, Mary Ann Liebert, Inc., London, U.K.
Byng, J. W., et al. Phys Med Biol 39 (1994): 1629-38.
Caldwell, C. B., et al. Phys Med Biol 35 (1990): 235-47.
Cameron IL, Smith NK, Pool TB, Sparks RL. Intracellular Concentration of Sodium and Other Elements as Related to Mitogenesis and Oncogenesis In Vivo, Cancer Research, May 1980, pp. 1493-1500, vol. 40, No. 5.
Carney, P. A., et al. Ann Intern Med 138 (2003): 168-75.
Cartman ML, Morris JA, Huddart H, Staff WG. Electrolyte Homeostasis in Urothelial Neoplasia: The Effects of Amiloride, British Journal of Urology, May 1995, pp. 599-603. vol. 75, No. 5, Blackwell Science, Ltd.
Champigny G, Verrier B, Lazdunski M. A Voltage, Calcium, and ATP Sensitive Non Selective Cation Channel in Human Colonic Tumor Cells, Biochemical and Biophysical Research Communications, May 1991, pp. 1196-1203, vol. 176, No. 3, Academic Press, Inc.
Chang, Y. H., et al. Acad Radiol 9 (2002): 899-905.
Chapman LM, Wondergem R. Transmembrane Potential and Intracellular Potassium Ion Activity in Fetal and Maternal Liver, Journal of Cellular Physiology, Oct. 1984, pp. 7-12, vol. 121, No. 1, Alan R. Liss, Inc.
Chauveau N, Hamzaoui L, Rochaix P, Rigaud B, Voigt JJ, Morucci JP. Ex Vivo Discrimination Between Normal and Pathological Tissues in Human Breast Surgical Biopsies Using Bioimpedance Spectroscopy, Annals of the New York Academy of Sciences, 1999, pp. 42-50, vol. 873, The New York Academy of Science, New York, NY, USA.
Chen CF, Corbley MJ, Roberts TM, Hess P. Voltage-Sensitive Calcium Channels in Normal and Transformed 3T3 Fibroblasts, Science, Feb. 1988, pp. 1024-1026, vol. 239, No. 4843.
Chen, B., et al. Med Phys 29 (2002): 755-70.
Cherepenin V, Karpov A, Korjenevsky A, Kornienko V, Mazaletskaya A, Mazourov D et al. A 3D Electrical Impedance Tomography (EIT) System for Breast Cancer Detection, Physiological Measurement, Feb. 2001, pp. 9-18, vol. 22, No. 1, Institute of Physics Publishing.
Chien JL, Warren JR. Free Calcium and Calmodulin Levels in Acinar Carcinoma and Normal Acinar Cells of Rat Pancreas, International Journal of Pancreatology, Mar. 1988, pp. 113-127, vol. 3, No. 2-3, Elsevier.
Chou CY, Shen MR, Wu SN. Volume-sensitive Chloride Channels Associated With Human Cervical Carcinogenesis, Cancer Research, Dec. 1995, pp. 6077-6083, vol. 55, No. 24, Official Journal of the American Association for Cancer Research.
Cone CD, JR. The Role of the Surface Electrical Transmembrane Potential in Normal and Malignant Mitogenesis, Annals of the New York Academy of Sciences, 1974, pp. 420-435, vol. 238, The New York Academy of Sciences, USA.
Cone CD, JR. Unified Theory on the Basic Mechanism of Normal Mitotic Control and Oncogenesis, Journal of Theoretical Biology, Jan. 1971, pp. 151-181, vol. 30, No. 1, Academic Press.
Cone CD, JR., Cone CM. Induction of Mitosis in Mature Neurons in Central Nervous System by Sustained Depolarization, Science, Apr. 1976, pp. 155-158, vol. 192, No. 4235.
Cuzick J, Holland R, Barth V, Davies R, Faupel M, Fentiman I et al. Electropotential Measurements as a New Diagnostic Modality for Breast Cancer. The Lancet, Aug. 1998, pp. 359-363, vol. 352, No. 9125.
dA Silva JE, DE SA JP, Jossinet J. Classification of Breast Tissue by Electrical Impedance Spectroscopy, Medical and Biological Engineering & Computing, Jan. 2000, pp. 26-30, vol. 38, No. 1.
Davies RJ, Asbun H, Thompson SM, Goller DA, Sandle GI. Uncoupling of Sodium Chloride Transport in Premalignant Mouse Colon, Gastroenterology, Jun. 1990, pp. 1502-1508, vol. 98, No. 6, American Gastroenterological Association.
Davies RJ, Joseph R, Asbun H, Sedwitz M. Detection of the Cancer-Prone Colon, Using Transepithelial Impedance Analysis, Archives of Surgery, Apr. 1989, pp. 480-484, vol. 124, No. 4, The American Medical Association, USA.
Davies RJ, Joseph R, Kaplan D, Juncosa RD, Pempinello C, Asbun H et al. Epithelial Impedance Analysis in Experimentally Induced Colon Cancer, Biophysical Journal, Nov. 1987, pp. 783-790, vol. 52, No. 5, The Biophysical Society by the Rockefeller University Press, USA.
Davies RJ, Juncosa RD, Kaplan D, Pempinello C, Asbun H, Pilch YH. Colonic Epithelial Impedance Analysis in a Murine Model of Large-Bowel Cancer, Archives of Surgery, Nov. 1986, pp. 1253-1258, vol. 121, No. 11, The American Medical Association, USA.
Davies RJ, Weidema WF, Sandle GI, Palmer L, Deschner EE, Decosse JJ. Sodium Transport in a Mouse Model of Colonic Carcinogenesis, Cancer Research, Sep. 1987, pp. 4646-4650, vol. 47, No. 17.
Davies RJ, Weiss A, Capko D, Brenner BM. Cell Membrane Potential in Benign and Malignant Breast Epithelial Cells. Breast Cancer Research and Treatment, 1996, p. 331, vol. 41, No. 3 Ref Type: Abstract, Kluwer Academic Publishers.
Davies, R.J., Quinn, D.A., Davisson T.H. Breast Cancer Res. and Treat.vol. 88, (Suppl. 1) S221: 6005, 2004.
Davies, R.J., Quinn, D.A., Davisson T.H. Breast Cancer Res. and Treat.vol. 88, (Suppl. 1) S222-3: 6009, 2004.
Decoursey TE, Cherny W. Voltage-Activated Proton Currents in Human THP-1 Monocytes, The Journal of Membrane Biology, Jul. 1996, pp. 131-140, vol. 152, No. 2, Springer.
Deutsch C, Price M. Role of Extracellular Na and K in Lymphocyte Activation, Journal of Cellular Physiology, Oct. 1982, pp. 73-79, vol. 113, No. 1, Alan R. Liss, Inc.
Ding, J., et al. Cancer Epidemiol Biomarkers Prev 17 (2008): 1074-81.
Diserbo M, Fatome M, Verdetti J. Activation of Large Conductance Ca(2+)-Activated K+ Channels in N1E-115 Neuroblastoma Cells by Platelet-Activating Factor. Biochemical and Biophysical Research Community, Jan. 1996, pp. 745-749, vol. 218, No. 3, Academic Press.
Diss JK, Stewart D, Fraser SP, Black JA, Dib-Hajj S, Waxman SG et al. Expression of Skeletal Muscle-Type Voltage-Gated Na+ Channel in Rat and Human Prostate Cancer Cell Lines, FEBS Letters, May 1998, pp. 5-10, vol. 427, No. 1, Elsevier on Behalf of the Federation of European Biochemical Sciences.
Wolfe, J. N., et al. AJR Am J Roentgenol 148 (1987): 1087-92.
Wu et al., "Tomographic mammography using a limited number of low-dose cone-beam projection iamages", Med Phys 30 (2003): 365-380.
Wykoff CC, Beasley N, Watson PH, Campo L, Chia SK, English R et al. Expression of the Hypoxia-Inducible and Tumor-Associated Carbonic Anhydrases in Ductal Carcinoma In Situ of the Breast, The American Journal of Pathology, Mar. 2001, pp. 1011-1019, vol. 158, No. 3, American Society for Investigative Pathology.
Yaffe, Martin Breast Cancer Research 10.3 (2008): 209.
Yao X, Kwan HY. Activity of Voltage-Gated K+ Channels is Associated With Cell Proliferation and Ca2+ Influx in Carcinoma Cells of Colon Cancer, Life Sciences Including Pharmacology Letters, May 1999, pp. 55-62, vol. 65, No. 1, Elsevier Science, Inc.
Zhou et al., "Computerized image analysis: Estimation of breast density on mammograms", Med Phys 28 (6), 1056-1069, (2001).
Paris S, Pouyssegur J. Biochemical Characterization of the Amiloride-Sensitive Na+/H+ Antiport in Chinese Hamster Lung Fibroblasts, The Journal of Biological Chemistry, Mar. 1983, pp. 3503-3508, vol. 258, No. 6, The American Society of Biological Chemists, Inc., USA.

(56) References Cited

OTHER PUBLICATIONS

Paris S, Pouyssegur J. Growth Factors Activate the Na+/H+ Antiporter in Quiescent Fibroblasts by Increasing Its Affinity for Intracellular H+, The Journal of Biological Chemistry, Sep. 1984, pp. 10989-10994, vol. 259, No. 17, The American Society of Biological Chemists, Inc., USA.
Pauli BU, Weinstein RS. Structure of Gap Junctions in Cultures of Normal and Neoplastic Bladder Epithelial Cells, Experientia, 1981, pp. 248-250, vol. 37, No. 3, Birkhaüser Verlag.
Pawluczyk et al., "A volumetric method for estimation of breast density on digitized screen-film mammograms", Med Phys 30 (2003): 352-364.
Piperno G, Frei EH, Moshitzky M. Breast Cancer Screening by Impedance Measurements, Frontiers in Medical and Biological Engineering, 1990, pp. 111-117, vol. 2, No. 2.
Poplack et al., Electromagnetic Breast Imaging: Average Tissue Property Values in Women with Negative Clinical Findings; Radiology 2004; 231:571-580.
Poupa V, Setka J, Vrana J. [Diagnosis of Malignant Diseases of the Mucosa of the Gastrointestinal Tract by Impedance Measurement Using the DIACA Apparatus], Rozhledy Chirurgii, 1986, pp. 316-321, vol. 65, No. 5.
Pouyssegur J, Chambard JC, Franchi A, Paris S, Obberghen-Schilling E. Growth Factor Activation of an Amiloride-Sensitive Na+/H+ Exchange System in Quiescent Fibroblasts: Coupling to Ribosomal Protein S6 Phosphorylation, Proceedings of the National Academy of Sciences of the United States of America, Jul. 1982, pp. 3935-3939, vol. 79, No. 13, National Academy of Sciences, USA.
Pouyssegur J, Sardet C, Franchi A, L'Allemain G, Paris S. A Specific Mutation Abolishing Na+/H+ Antiport Activity in Hamster Fibroblasts Precludes Growth at Neutral and Acidic Ph., Proceedings of the National Academy of Sciences of the United States of America, Aug. 1984, pp. 4833-4837, vol. 81, No. 15, National Academy of Sciences, USA.
Prat AG, Cunningham CC, Jackson GR, JR., Borkan SC, Wang Y, Ausiello DA et al. Actin Filament Organization is Required for Proper Camp-Dependent Activation of CFTR., American Journal of Physiology, Dec. 1999, pp. C1160-C1169 vol. 277, No. 6 Part 1, The American Physiology Society.
Rane SG. A Ca2(+)-Activated K+ Current in Ras-Transformed Fibroblasts is Absent From Nontransformed Cells, American Journal of Physiology, Jan. 1991, pp. C104-C112, vol. 260, No. 1, Part 1, The American Physiological Society.
Rane SG. The Growth Regulatory Fibroblast IK Channel is the Prominent Electrophysiological Feature of Rat Prostatic Cancer Cells, Biochemical and Biophysical Research Communications, Mar. 2000, pp. 457-463, vol. 269, No. 2, Academic Press.
Redmann K, Walliser S. Different Changes in Transmembrane Potential of Cultured Cells After Ouabain-Inhibited Active Na+/K+-Transport. Archiv Fur Geschwulstforsch, 1981; pp. 96-102. vol. 51, No. 1, Volk und Gesundheit, Berlin.
Reuss L, Cassel D, Rothenberg P, Whiteley P, Mancuso D, Glaser L. Mitogens and Ion Fluxes. In: Mandel LJ, Benos DJ, Editors. The Role of Membranes in Cell Growth and Differentiation, Academic Press Inc., Hartcourt Brace Jovanovich, 1986, pp. 3-54, vol. 27, Orlando, Fla.
Rothenberg P, Reuss L, Glaser L. Serum and Epidermal Growth Factor Transiently Depolarize Quiescent BSC- 1 Epithelial Cells, Proceedings of the National Academy of Sciences of the United States of America, Dec. 1982, pp. 7783-7787, vol. 79, No. 24.
Rouzaire-Dubois B, Milandri JB, Bostel S, Dubois JM. Control of Cell Proliferation by Cell Volume Alterations in Rat C6 Glioma Cells. Pflugers Archiv European Journal of Physiology, Oct. 2000, vol. 440, No. 6, Springer.
Sachs HG, Stambrook PJ, Ebert JD. Changes in Membrane Potential During the Cell Cycle, Experimental Cell Research, Feb. 1974, pp. 362-366, vol. 83, No. 2, Academic Press, New York and London.
Saftlas et al., "Mammographic parenchymal patterns and breast cancer risk", Epidemiologic Reviews, vol. 9 (1987): 146-174.
Saqr He, Guan Z, Yates AJ, Stokes BT. Mechanisms Through Which PDGF Alters Intracellular Calcium Levels in U- 1242 MG Human Glioma Cells, Neurochemistry International, Dec. 1999, pp. 411-422, vol. 35, No. 6, Elsevier Science Ltd.
Schaefer H, Schanne O. Membranpotentiale Von Einzelzellen in Gewebekulturen, Naturwissenschaften 1956, p. 445, vol. 43, Springer-Verlag.
Schultz SG. Basic Principles of Membrane Transport, 1 ed. 1980, Cambridge University Press, London and New York.
Schultz SG. Homocellular Regulatory Mechanisms in Sodium-Transporting Epithelia: Avoidance of Extinction by "Flush-Through", American Journal of Physiology, Dec. 1981, pp. F579-F590, vol. 241, No. 6, The American Physiological Society.
Schwan, H.P., Electrical Properties of Tissue and Cell Suspensions In: "Advances in Biological and Medical Physics," J.H. Lawrence and C.A. Tobias, Eds. vol. V, 1957, p. 147, Aladdin Press, Inc., New York.
Setka J, Vrana J. [Impedance in the Endoscopy of Rectal Neoplasms], Sb Ornik Lekarsky, 1970, pp. 89-93, vol. 72, No. 4.
Setka J, Vrana J. [Impedance of the Recto-Sigmoidal Mucosa Measured by Endoscopy in the Diagnosis of Rectal Neoplasms], Archives Francaises des Maladies de L'Appareil Digestif, 1969, pp. 477-482, vol. 58, No. 7, Masson & Cie, Paris, France.
Shen MR, Chou CY, Ellory JC. Volume-Sensitive KCl cotransport Associated With Human Cervical Carcinogenesis, Pflügers Archibe European Journal of Physiology, Sep. 2000, pp. 751-760, vol. 440, No. 5, Springer.
Shen MR, Droogmans G, Eggermont J, Voets T, Ellory JC, Nilius B. Differential expression of Volume-Regulated Anion Channels During Cell Cycle Progression of Human Cervical Cancer Cells, The Journal of Physiology, Dec. 2000, pp. 385-394, vol. 529, Pt 2, The Physiological Society.
Shepherd, J. A., et al. Radiology 223 (2002): 554-57.
Shuba YM, Prevarskaya N, Lemonnier L, Van Coppenolle F, Kostyuk PG, Mauroy B et al. Volume-Regulated Chloride Conductance in the LNCaP Human Prostate Cancer Cell Line, American Journal of Physiology Cell Physiology, Oct. 2000, pp. C1144-C1154, vol. 279, No. 4, The American Physiological Society.
Simonneau M, Distasi C, Tauc L, Poujeoi C. Development of Ionic Channels During Mouse Neuronal Differentiation, Journal de Physiologie, 1985, pp. 312-332, vol. 80, No. 2, Masson, Paris, France.
Sivaramakrishna, R., et al. Acad Radiol 8 (2001): 250-56.
Skryma R, Van Coppenolle F, Dufy-Barbe L, Dufy B, Prevarskaya N. Characterization of Ca(2+)-Inhibited Potassium Channels in the LNCaP Human Prostate Cancer Cell Line, Receptors and Channels, 1999, pp. 241-253, vol. 6, No. 4, Harwood Academic Publishers, Malaysia.
Skryma RN, Prevarskaya NB, Dufy-Barbe L, Odessa MF, Audin J, Dufy B. Potassium conductance in the Androgen-Sensitive Prostate Cancer Cell Line, LNCaP: Involvement in Cell Proliferation, The Prostate, 1997, pp. 112-122, vol. 33, No. 2, Wiley-Liss, Inc.
Slaughter DP, Southwick HW, Smejkal W. "Field Cancerization" in Oral Squamous Epithelium: Clinical Implications of Multicentric Origin, Cancer, A Journal of American Cancer, Jul. 1953, pp. 963-968, vol. 6, No. 4, J.B. Lippincott Company, Philadelphia, PA, USA.
Stemmer-Rachamimov AO, Wiederhold T, Nielsen GP, James M, Pinney-Michalowski D, Roy JE et al. NHE-RF, A Merlin-Interacting Protein, Is Primarily Expressed in Luminal Epithelia, Proliferative Endometrium, and Estrogen Receptor-Positive Breast Carcinomas, The American Journal of Pathology, Jan. 2001, pp. 57-62, vol. 158, No. 1, American Society for Investigative Pathology.
Stojadinovic A, Nissan A, Gallimidi Z, et.al. J Clin Oncol Apr. 20, 2005; 23(12):2703-11.
Tapia-Vieyra JV, Mas-Oliva J. Apoptosis and Cell Death Channels in Prostate Cancer, Archives of Medical Research, 2001, pp. 175-185, vol. 32, No. 3, Elsevier Science, Inc.
Thompson SM, Suzuki Y, Schultz SG. The Electrophysiology of Rabbit Descending Colon. I. Instantaneous Transepithelial Current-Voltage Relations and the Current-Voltage Relations of the Na-Entry Mechanism, Journal of Membrane Biology, 1982, pp. 41-45, vol. 66, No. 1, Springer-Verlag, New York New York, USA.

(56) References Cited

OTHER PUBLICATIONS

Thurnherr N, Deschner EE, Stonehill EH, Lipkin M. Induction of Adenocarcinomas of the Colon in Mice by Weekly Injections of 1,2-dimethylhydrazine, Cancer Research, May 1973, pp. 940-945, vol. 33, No. 5.

Tokuoka S, Morioka H. The Membrane Potential of the Human Cancer and Related Cells, "GANN" The Japanese Journal of Cancer Research, Gann, 1957, pp. 353-354, vol. 48, The Japanese Cancer Association and the Japanese Foundation for Cancer Research, Nishi-Sugamo, Toshima-ku, Tokyo, Japan.

Vachon, C. M., et al. Cancer Epidemiol Biomarkers Prev 11 (2002): 1382-88.

Veselovskii NS, Fomina AF. [Sodium and Calcium Channels of the Somatic Membrane of Neuroblastoma Cells During Artificially Induced Differentiation]. Neirofiziologiia 1986; pp. 207-214, vol. 18, No. 2.

Villereal ML. Sodium Fluxes in Human Fibroblasts: Effect of Serum, Ca+2, and Amiloride. Journal of Cellular Physiology, Jun. 1981, pp. 359-369, vol. 107, No. 3, Alan R. Liss, Inc.

Vyklicky L, JR., Michl J, Vlachova V, Vyklicky L, Vyskocil F. Ionic Currents in Neuroblastoma Clone E-7 Cells, Neuroscience Letters, 1985, pp. 197-201, vol. 55, No. 2, Elsevier Scientific Publishers, Ireland.

Warner et al., "The risk of breast cancer associated with Mammographic Parenchymal Patterns: A meta-analysis of the published literature to examine the effect of method of classification", Cancer Detect Prev 16 (1992): 67-72.

Webster, M.A., Cardiff, R.D., and Muller, W.J. Proc. Natl. Acad. Sci. U.S.A. 1995 92:7849-7853.

Wieland SJ, Chou RH, Chen TA. Elevation of a Potassium Current in Differentiating Human Leukemic (HI-60) Cells, Journal of Cell Physiology, Aug. 1987, pp. 371-375, vol. 132, No, 2, Alan R. Liss, Inc.

Wissenbach U, Niemeyer BA, Fixemer T, Schneidewind A, Trost C, Cavalie A et al. Expression of CaT-like, A Novel Calcium-Selective Channel, Correlates With the Malignancy of Prostate Cancer, The Journal of Biological Chemistry, Jun. 2001, pp. 19461-19468, vol. 276, No. 22, The American Society for Biochemistry and Molecular Biology.

Wolf, J. N., "Risk for breast cancer development determined by mammographic parenchymal pattern", Cancer 37 (1976): 2486-92 (Abstract only.).

Wolfe, J. N. AJR Am J Roentgenol 126.6 (1976): 1130-37.

Ihara et al., "Finite Element Analysis of Breast Bioimpedace", Technical Report of IEICE MBE99-57, (Jul. 1999), pp. 13-18.

Koki et al., "Automatic classification algorithm of the mammary gland structure in Mammogram", IEICE Technical Report MBE2006-51, 2006, pp. 49-52.

\* cited by examiner

Correlation of Sub-Epithelial Impedance with Age

Effect of Menstrual Cycle on Sub Epithelial Impedance

Changes in Sub-Epithelial Impedance
During Menstrual Cycle by Parity

Correlation of Sub Epithelial Impedance with Weight

Correlation of Sub Epithelial Impedance with Distance from Nipple

Correlation of Density Estimate (DE) with BiRads and DE Between Two Independent Observers

Correlation of Estimate of Mammographic Density with Subepithelial Impedance (Zsub)

ELECTRICAL BIOIMPEDANCE ANALYSIS AS A BIOMARKER OF BREAST DENSITY AND/OR BREAST CANCER RISK

CROSS-REFERENCE TO RELATED APPLICATIONS

This application claims the benefit of the filing date of U.S. Provisional Patent Application No. 61/007,128 filed Dec. 11, 2007, the disclosure of which is hereby incorporated herein by reference.

BACKGROUND OF THE INVENTION

The ideal or preferred biomarker of breast density and/or cancer risk includes the following characteristics: (1) biologic plausibility; (2) a higher rate of expression in high-risk compared to low-risk populations; (3) an association with cancer in prospective studies; (4) expression minimally influenced by normal physiologic processes, or the ability to control for the influences of physiology; (5) the ability to obtain the biomarker using minimally invasive techniques at low costs; and (6) reproducibility. For purposes of the present invention the generally accepted National Institutes of Health definition of a "biomarker" is adopted: "a characteristic that is objectively measured and evaluated as an indicator of normal biologic processes, pathogenic processes, or pharmacologic responses to a therapeutic intervention." (Biomarkers Definitions working Group: Biomarkers And Surrogate Endpoints: Preferred Definitions And Conceptual Framework. Clin. Pharmacol. Ther. 2001; 69:89-95). As will be shown hereinbelow, the present invention relates generally to the measurement, especially the non-invasive measurement, of electrophysiological characteristics, preferably subepithelial impedance, as a biomarker for estimating breast density and further, the use of such estimated breast density as a further biomarker for breast cancer or abnormal tissue, preferably for use in assessing the risk that an individual will develop breast cancer or abnormal tissue.

The present invention relates generally to the detection of proliferative, abnormal or cancerous tissue, and more particularly, to the detection of changes in the electrophysiological characteristics of proliferative, abnormal or cancerous tissue and to changes in those electrophysiological characteristics related to the functional, structural and topographic (the interaction of shape, position and function) relationships of the tissue during the development of malignancy. These measurements can be made in the absence and presence of pharmacological and hormonal agents to reveal and accentuate the electrophysiological characteristics of proliferative, abnormal or cancerous tissue.

Cancer is a leading cause of death in both men and women in the United States. Difficulty in detecting proliferative, abnormal pre-cancerous or cancerous tissue before treatment options become non-viable is one of the reasons for the high mortality rate. Detecting of the presence of proliferative, abnormal or cancerous tissues is difficult, in part, because such tissues are largely located deep within the body, thus requiring expensive, complex, invasive, and/or uncomfortable procedures. For this reason, the use of detection procedures is often restricted until a patient is experiencing symptoms related to the abnormal tissue. Many forms of cancers or tumors, however, require extended periods of time to attain a detectable size (and thus to produce significant symptoms or signs in the patient). It is often too late for effective treatment by the time the detection is performed with currently available diagnostic modalities.

Breast cancer is the most common malignancy affecting women in the Western World. The reduction in mortality for this common disease depends on early detection. The mainstay of early detection are X-ray mammography and clinical breast examination. Both are fraught with problems of inaccuracy. For example, mammography has a lower sensitivity in women with dense breasts, and is unable to discriminate between morphologically similar benign or malignant breast lesions.

Clinical breast examinations are limited because lesions less than one cm are usually undetectable and larger lesions may be obscured by diffuse nodularity, fibrocystic change, or may be too deep in the breast to enable clinical detection. Patients with positive mammographic or equivocal clinical findings often require biopsy to make a definitive diagnosis. Moreover, biopsies may be negative for malignancy in up to 80% of patients.

Accordingly, mammography and clinical breast examination have relatively poor specificity in diagnosing breast cancer. Therefore many positive mammographic findings or lesions detected on clinical breast examination ultimately prove to be false positives resulting in physical and emotional trauma for patients. Improved methods and technologies to identify patients who need to undergo biopsy would reduce healthcare costs and avoid unnecessary diagnostic biopsies.

It is also desirable to develop improved technology suitable for characterizing pre-cancerous tissue and cancer in other tissue types and elsewhere in the body, particularly methods and devices suitable for ascertaining the condition of bodily ductal structures, e.g., the prostate, pancreas, etc., as well as the breast. Such characterization may ultimately be useful in diagnosis or risk assessment.

One proposed method for early detection of cancerous and pre-cancerous tissue includes measuring of the electrical impedance of biological tissue. For example, U.S. Pat. No. 3,949,736 discloses a low-level electric current passed through tissue, with a measurement of the voltage drop across the tissue providing an indirect indication of the overall tissue impedance. This method teaches that a change in impedance of the tissue is associated with an abnormal condition of the cells composing the tissue, indicating a tumor, carcinoma, or other abnormal biological condition. This disclosure, however, does not discuss either an increase or decrease in impedance associated with abnormal cells, nor does it specifically address tumor cells or other patient-specific factors that affect electrophysiological properties.

It is also noted that the above and similar systems do not consider DC electrical properties of the epithelium. Most common malignancies develop in an epithelium (the cell layer that lines a hollow organ, such as the bowel, or ductal structures such as the breast or prostate), that maintains a transepithelial electropotential. Early in the malignant process the epithelium loses its transepithelial potential, particularly when compared to epithelium some distance away from the developing malignancy. The combination of transepithelial electropotential measurements with impedance are more accurate in diagnosing pre-cancerous and cancerous conditions.

Another disadvantage of the above referenced system is that the frequency range of the electrical signal is not defined. Certain information is obtained about cells according to the range of frequencies selected. Different frequency bands may be associated with different structural or functional aspects of the tissue. See, for example, F. A. Duck, Physical Properties of Tissues, London: Academic Press, 2001; K. R. Foster, H. P. Schwan, *Dielectric properties of tissues and biological materials: a critical review*, Crit. Rev. Biomed. Eng., 1989, 17 (1):

25-104. For example at high frequencies such as greater than about 1 GHz molecular structure has a dominating effect on the relaxation characteristics of the impedance profile. Relaxation characteristics include the delay in the response of a tissue to a change in the applied electric field. For example, an applied AC current results in a voltage change across the tissue which will be delayed or phase shifted, because of the impedance characteristics of the tissue. Relaxation and dispersion characteristics of the tissue vary according to the frequency of the applied signal.

At lower frequencies, such as less than about 100 Hz, or the so called α-dispersion range, alterations in ion transport and charge accumulations at large cell membrane interfaces dominate the relaxation characteristics of the impedance profile. In the frequency range between a few kHz and about 1 MHz, or the so-called β-dispersion range, cell structure dominates the relaxation characteristics of the epithelial impedance profile. Within this range at low kHz frequencies, most of the applied current passes between the cells through the paracellular pathway and tight junctions. At higher frequencies in the β-dispersion range the current can penetrate the cell membrane and therefore passes both between and through the cells, and the current density will depend on the composition and volume of the cytoplasm and cell nucleus. Characteristic alterations occur in the ion transport of an epithelium during the process of malignant transformation affecting the impedance characteristics of the epithelium measured at frequencies in the α-dispersion range. Later in the malignant process, structural alterations with opening of the tight junctions and decreasing resistance of the paracellular pathways, together with changes in the composition and volume of the cell cytoplasm and nucleus, affect the impedance measured in the β-dispersion range.

Another disadvantage with the above referenced system is that the topography of altered impedance is not examined. By spacing the measuring electrodes differently the epithelium can be probed to different depths. The depth that is measured by two surface electrodes is approximately half the distance between the electrodes. Therefore electrodes 1 mm apart will measure the impedance of the underlying epithelium to a depth of approximately 500 microns. It is known, for example, that the thickness of bowel epithelium increases at the edge of a developing tumor to $1356\pm208\mu$ compared with $716\pm112\mu$ in normal bowel. D. Kristt, et al., *Patterns of proliferative changes in crypts bordering colonic tumors: zonal histology and cell cycle marker expression*, Pathol. Oncol. Res 1999; 5 (4): 297-303. Thickening of the ductal epithelium of the breast is also observed as ductal carcinoma in-situ develops. By comparing the measured impedance between electrodes spaced approximately 2.8 mm apart and compared with the impedance of electrodes spaced approximately 1.4 mm apart, information about the deeper and thickened epithelium may be obtained. See, for example, L. Emtestam, S. Ollmar, *Electrical impedance index in human skin: measurements after occlusion, in 5 anatomical regions and in mild irritant contact dermatitis*, Contact Dermatitis 1993; 28 (2): 104-108.

A further disadvantage of the above referenced methods is that they do not probe the specific conductive pathways that are altered during the malignant process. For example, potassium conductance is reduced in the surface epithelium of the colon early in the malignant process. By using electrodes spaced less than 1 mm apart with varying concentrations of potassium chloride the potassium conductance and permeability may be estimated in the surface epithelium at a depth from less than $500\mu$ to the surface.

A number of non-invasive impedance imaging techniques have been developed in an attempt to diagnose breast cancer. Electrical impedance tomography (EIT) is an impedance imaging technique that employs a large number of electrodes placed on the body surface. The impedance measurements obtained at each electrode are then processed by a computer to generate a 2-dimensional or 3-dimensional reconstructed tomographic image of the impedance and its distribution in 2 or 3 dimensions. This approach relies on the differences in conductivity and impedivity between different tissue types and relies on data acquisition and image reconstruction algorithms which are difficult to apply clinically.

The majority of EIT systems employ "current-driving mode," which applies a constant AC current between two or more current-passing electrodes, and measures the voltage drop between other voltage-sensing electrodes on the body surface. Another approach is to use a "voltage-driving approach," which applies a constant AC voltage between two or more current-passing electrodes, and then measures the current at other current-sensing electrodes. Different systems vary in the electrode configuration, current or voltage excitation mode, the excitation signal pattern, and AC frequency range employed.

Another disadvantage with using EIT to diagnose breast cancer is the inhomogeneity of breast tissue. The image reconstruction assumes that current passes homogeneously through the breast tissue which is unlikely given the varying electrical properties of different types of tissue comprising the breast. In addition image reconstruction depends upon the calculation of the voltage distribution on the surface of the breast from a known impedance distribution (the so called forward problem), and then estimating the impedance distribution within the breast from the measured voltage distribution measured with surface electrodes (the inverse problem). Reconstruction algorithms are frequently based on finite element modeling using Poisson's equation and with assumptions with regard to quasi-static conditions, because of the low frequencies used in most EIT systems.

Other electrically-based methods for cancer diagnosis are disclosed in the patent and journal literature. A brief discussion of such disclosures can be found in the copending patent application by the inventor herein, U.S. Ser. No. 11/879,805, filed Jul. 18, 2007, the disclosure of which is incorporated herein by reference.

Another potential source of information for the detection of abnormal tissue is the measurement of transport alterations in the epithelium. Epithelial cells line the surfaces of the body and act as a barrier to isolate the body from the outside world. Not only do epithelial cells serve to insulate the body, but they also modify the body's environment by transporting salts, nutrients, and water across the cell barrier while maintaining their own cytoplasmic environment within fairly narrow limits. One mechanism by which the epithelial layer withstands the constant battering is by continuous proliferation and replacement of the barrier. This continued cell proliferation may partly explain why more than 80% of cancers are of epithelial cell origin. Moreover, given their special abilities to vectorially transport solutes from blood to outside and vice versa, it appears that a disease process involving altered growth regulation may have associated changes in transport properties of epithelia.

Epithelial cells are bound together by tight junctions, which consist of cell-to-cell adhesion molecules. These adhesion proteins regulate the paracellular transport of molecules and ions between cells and are dynamic structures that can tighten the epithelium, preventing the movement of substances, or loosen allowing substances to pass between cells.

Tight junctions consist of integral membrane proteins, claudins, occludins and JAMs (junctional adhesion molecules). Tight junctions will open and close in response to intra and extracellular stimuli.

A number of substances will open or close tight junctions. The pro-inflammatory agent TGF-alpha, cytokines, IGF and VEGF opens tight junctions. Zonula occludens toxin, nitric oxide donors, and phorbol esters also reversibly open tight junctions. Other substances close tight junctions including calcium, H2 antagonists and retinoids. Various hormones such as prolactin and glucocorticoids will also regulate the tight junctions. Other substances added to drug formulations act as non-specific tight junction modulators including chitosan and wheat germ agglutinin.

The above referenced substances and others may act directly or indirectly on the tight junction proteins, which are altered during carcinogenesis. For example claudin-7 is lost in breast ductal epithelium during the development of breast cancer. The response of the tight junctions varies according to the malignant state of the epithelium and their constituent proteins. As a result the opening or closing of tight junctions is affected by the malignant state of the epithelium.

Surface measurements of potential or impedance are not the same as measurements performed across the breast epithelium where electrical contact is made between the luminal surface of the duct and the overlying skin. Transepithelial depolarization is an early event during carcinogenesis, which may affect a significant region of the epithelium (a "field defect"). This depolarization is accompanied by functional changes in the epithelium including ion transport and impedance alterations. Early on in the process these take the form of increased impedance because of decreased specific electrogenic ion transport processes. As the tumor begins to develop in the pre-malignant epithelium, structural changes occur in the transformed cells such as a breakdown in tight junctions and nuclear atypia. The structural changes result in a marked reduction in the impedance of the tumor. As previously described by the present inventor, understanding and interpreting the pattern and gradient of electrical changes in the epithelium can assist in the diagnosis of cancer from a combination of DC electrical and impedance measurements.

Breast cancer is thought to originate from epithelial cells in the terminal ductal lobular units (TDLUs) of mammary tissue. These cells proliferate and have a functional role in the absorption and secretion of various substances when quiescent and may produce milk when lactating. Functional alterations in breast epithelium have largely been ignored as a possible approach to breast cancer diagnosis. Breast epithelium is responsible for milk formation during lactation. Every month pre-menopausal breast epithelium undergoes a "rehearsal" for pregnancy with involution following menstruation. The flattened epithelium becomes more columnar as the epithelium enters the luteal phase from the follicular phase. In addition, duct branching and the number of acini reach a maximum during the latter half of the luteal phase. Just before menstruation apoptosis of the epithelium occurs and the process starts over again unless the woman becomes pregnant.

It is known that various hormones affect breast epithelial ion transport. For example, prolactin decreases the permeability of the tight-junctions between breast epithelial cells, stimulates mucosal to serosal $Na^+$ flux, upregulates $Na^+$:$K^+$:$2Cl^-$ cotransport and increases the $[K^+]$ and decreases the $[Na^+]$ in milk. Glucocorticoids control the formation of tight-junctions increasing transepithelial resistance and decreasing epithelial permeability. Administration of cortisol into breast ducts late in pregnancy has been shown to increase the $[K^+]$ and decrease $[Na^+]$ of ductal secretions. Progesterone inhibits tight-junction closure during pregnancy and may be responsible for the fluctuations in ductal fluid electrolytes observed during menstrual cycle in non-pregnant women, and discussed above. Estrogen has been observed to increase cell membrane and transepithelial potential and may stimulate the opening of $K^+$-channels in breast epithelial cells. The hormones mentioned above vary diurnally and during menstrual cycle. It is likely that these variations influence the functional properties of breast epithelium altering the ionic concentrations within the lumen, the transepithelial potential and impedance properties, which are dependent upon the ion transport properties of epithelial cells and the transcellular and paracellular conductance pathways.

Breast cancer biomarkers have recently attracted national attention and various markers that have been studied in women at risk for breast cancer include the following:

Germline Mutations and Polymorphisms: Highly penetrant genes such as BRCA1/BRCA2 with deleterious germline mutations are strong predictors of breast cancer development, but are found in less than 5-10% of women with breast cancer and in only 1% of the general population. Single nucleotide polymorphisms of genes whose protein products are involved in carcinogen and hormone metabolism and/or DNA repair are associated with relative risks of 1.4-2.0, however combined polymorphisms may be associated with significantly higher relative risks.

Hormones and Metabolites: Serum bioavailable estradiol and testosterone may represent risk biomarkers in postmenopausal women, and serum insulin-like growth factor-I (IGF-I) and its binding protein-3 (IGFBP-3) in premenopausal women. However none have been established to definitively identify high-risk women.

Mammographic Breast density and Intraepithelial Neoplasia: Mammographic breast density and breast intra-epithelial neoplasia apply to many more of the female population than germline mutations in tumor-suppressor genes. Furthermore, since they are subject to modulation, these risk biomarkers might be used to monitor change in breast cancer susceptibility from a prevention intervention standpoint. Mammographic breast density and intra-epithelial neoplasia are useful in both pre- and post-menopausal women. However, Tice et al. (*Breast Cancer Res. Treat.* 94:115-22, 2005) and Chen et al. (*J. Natl. Cancer Inst.* 98:1215-26, 2006) have reported that mammographic density adds modestly to the Gail model (M. H. Gail et al., J. Natl. Cancer Inst. 81 (24): 1879-86, 1989) in improving discriminatory accuracy. Assessing density typically requires the use of radiation-based methods and is subject to inter-observer variability. Improvements in the estimation of breast density have been proposed using volumetric and three dimensional magnetic resonance imaging (MRI) approaches.

Breast intra-epithelial neoplasia is a risk biomarker with close biologic association with cancer, and is least likely to be affected by normal physiological processes, although ductal proliferation may be influenced by position in menstrual cycle. (See Fabian et al., *Endocr. Relat Cancer* 12:185-213, 2005, for a review). This includes proliferative breast disease without atypia, atypical ductal and lobular hyperplasia and in situ cancer. Within the spectrum of intra-epithelial neoplasia, an increase in morphologic abnormality is associated with a progressive increase in relative risk and a shorter time (decreased latency) to the development of breast cancer. Proliferative breast disease without atypia (moderate to florid hyperplasia, sclerosing adenosis, papillomas, etc.) is found in approximately 25-30% of diagnostic biopsies and is associated with a 1.4-2.0-fold increase in the relative risk for breast cancer. Higher relative risks associated with proliferative disease without atypia (e.g. 2.0 versus 1.4) may be associated with older age (>50 years), because of a failure to down-regulate proliferation at menopause, or a positive family history.

Ductal or lobular atypical hyperplasia, identified on diagnostic biopsies, is associated with an approximate 5-fold increase in relative risk regardless of other risk factors. Women identified with atypia, but without a positive family history, have an approximately 4 to 5-fold increased risk, whereas women with a positive family history double their relative risk of breast cancer to approximately 10-fold. Atypical ductal and lobular hyperplasia are observed in 3-10% of unselected diagnostic surgical and core needle biopsies. Those women who ultimately develop cancer have a higher proportion of prior benign biopsies exhibiting atypical hyperplasia than those who do not. Several investigators have suggested that atypical hyperplasia may arise more commonly from an intermediate lesion called an unfolded lobule (A for ductal, B for lobular) than hyperplasia of the usual type (HUT). Both atypical hyperplasia and HUT may arise from unfolded lobules. These unfolded lobules are characterized by increased cellularity and proliferation with distension of the terminal lobule duct unit.

Genetic changes associated with Intraepithelial Neoplasia: ADH and DCIS often have similar molecular and genetic changes as assessed by immunocytology or mRNA gene profiles. Approximately 50% of ADH lesions demonstrate loss of heterozygosity, which is observed somewhat less frequently for HUT lesions. The most frequent chromosomal losses are at 16q and 17p for both HUT and atypical hyperplasia, similar to those observed for DCIS. Similar chromosomal gains and losses for non-invasive and invasive lobular cancer are observed using comparative genomic hybridization techniques. The loss of 16q, which contains E-cadherin, a tumor-suppressor gene involved in cell adhesion and cell-cycle regulation. It is reported that E-cadherin is expressed in normal cells, but is lost in LCIS and invasive lobular cancer. ADH is reported in 5% or less of diagnostic biopsies, and has been reported in 9% of autopsy specimens from average-risk women. However, it is observed in 39% of prophylactic mastectomy specimens from high-risk women. Furthermore, it has been reported that 57% of women with a family history consistent with that of a mutation in BRCA1 and/or BRCA2 had atypical ductal or lobular lesions and/or in situ cancer and these lesions were often multifocal or multicentric.

Altered Hormonal receptor status: An inverse relationship has been observed between serum estradiol and ER-α of breast epithelium in women without breast cancer, which is dependent on position in menstrual cycle. This relationship has not been observed in breast epithelium derived from women with breast cancer. Epithelial proliferation was inversely correlated to ER in controls, but was positively related in breast cancer cases. These observations have lead to the suggestion that that the surrounding epithelium of women with breast cancer may display an aberrant response to estradiol with ER up-regulating in the luteal phase of menstrual cycle, whereas it down-regulates in breast epithelium from women without breast cancer. The effect of this aberrant response on breast epithelial morphology is unknown. Women with an increased risk appear not to down-regulate in their menstrual cycle as do normal risk women. Proliferative up-regulation may persist in women at increased risk for breast cancer based on the inventor's observations in women undergoing breast biopsy for proliferative breast disease.

Thus, there remains a need for effective and practical methods for characterizing tissue, particularly breast tissue and the density of the breast, that is susceptible to abnormal changes and for using such information to assess the risk that a patient, and particularly one that is substantially asymptomatic, will be found to have proliferative, abnormal or pre-cancerous breast tissue.

The disclosures of the following patent applications, each to Richard J. Davies, the inventor herein, are hereby incorporated by reference herein: U.S. patent application Ser. No. 11/879,805, filed Jul. 18, 2007, entitled "Method and System for Detecting Electrophysiological Changes in Pre-Cancerous and Cancerous Tissue" published as US 2008/0009764 Jan. 10, 2008; U.S. patent application Ser. No. 10/151,233, filed May 20, 2002, entitled "Method and System for Detecting Electrophysiological Changes in Pre-Cancerous and Cancerous Tissue," now U.S. Pat. No. 6,922,586, issued Jul. 26, 2005; U.S. patent application Ser. No. 10/717,074, filed Nov. 19, 2003, entitled "Method And System For Detecting Electrophysiological Changes In Pre-Cancerous And Cancerous Breast Tissue And Epithelium"; and U.S. patent application Ser. No. 10/716,789, filed Nov. 19, 2003, published as US 2004/0253652 Dec. 16, 2004, entitled "Electrophysiological Approaches To Assess Resection and Tumor Ablation Margins and Responses To Drug Therapy" published as US 2004/0152997 Aug. 5, 2004.

SUMMARY OF THE INVENTION

Several embodiments of the invention are set forth in the following paragraphs:

1. A method for estimating the percent mammographic density (MD) of at least one breast of an individual, the breast comprising an overlying skin surface and nipple, the method comprising the following steps:

(A) establishing a connection between a first electrode and subepithelial parenchymal tissue in the breast of the individual;

(B) placing at least one second electrode in contact with the skin surface of the breast proximate the subepithelial tissue at a fixed distance from the nipple of the breast;

(C) establishing at least one electrical signal having a frequency between the first and second electrodes;

(D) measuring the subepithelial impedance (Zsub) at least one frequency between the first and second electrode;

(E) obtaining an estimate of the density of the breast according to an algorithm relating Zsub to mammographic breast density estimated or calculated according to a method independent of steps (A) through (D).

2. The method according to paragraph 1 wherein the algorithm includes variables associated with (i) characteristics of the individual; (ii) conditions under which the electrical measurement are made; or (iii) both (i) and (ii).

3. The method according to paragraph 2 wherein the variables are selected from the group consisting of the individuals age, body mass index, weight, parity, whether such individual is a premenopausal female, whether such individual is a postmenopausal female, where a female individual is in her menstrual cycle, and distance from the nipple that the skin surface electrode is placed.

4. The method according to paragraph 1 wherein the independent method for estimating or calculating breast density is based on images selected from the group consisting of X-rays, ultrasound and magnetic resonance imaging (MRI).

5. The method according to paragraph 4 wherein said method based on X-ray images is selected from the group consisting of: the Wolfe Pattern; Six Category Classification; BI-RADS; ACR BI-RADS; planimetry; image digitization; interactive threshold of digitized X-ray images; texture measurement of X-ray images; computer-calculated image texture measurements; computed tomography (CT) imaging; breast tomosynthesis; dual-energy X-ray absorptiometry; and digital mammography.

6. The method according to paragraph 1 wherein the algorithm is selected from the group consisting of:

$$MD=141.788+(-0.716*age)+(-1.113*BMI)+(-0.199*Zsub); \quad (I)$$

$$MDpmw=127.770+(-1.339*BMI)+(-0.259*Zsub); \text{ and} \quad (II)$$

$$MDpstmw=127.178+(-0.874*Age)+(-0.219*Zsub); \quad (III)$$

wherein the symbol * indicates multiplication of the terms preceding and following the symbol; BMI=body mass index calculated as $(Wt*703)/Height^2(inches^2)$, or $(Wt*4.88/Height^2(ft^2))$, where Wt is in pounds; Zsub is expressed in ohms; age is expressed in years; MDpmw=mammographic density for pre-menopausal women; MDpstmw=mammographic density for post-menopausal women.

7. The method according to paragraph 1 wherein Zsub is adjusted for the distance that the electrode is from the nipple (ADJZsub) according to the equation:

$$ADJZsub=Zsub_M/Zsub_{DFN} \text{ (where subscript } M\text{=measured); and}$$

$$Zsub_{DFN}=169.512+(6.668*DFN), \text{ where DFN=distance of the electrode from the nipple in cm.}$$

8. The method according to paragraph 1 wherein Zsub is adjusted for the distance that the electrode is from the nipple (ADJZsub) and the algorithm is selected from the group consisting of:

$$MDpmw=131.936+(-1.444*BMI)+(-54.752*ADJZsub) \quad (I)$$

or $$MDpstmw=120.178+(-0.869*Age)+(-39.179*ADJZsub); \quad (II)$$

wherein
MDpmw=mammographic density for pre-menopausal women;
MDpstmw=mammographic density for post-menopausal women;
$ADJZsub=Zsub_M/Zsub_{DFN}$ (where subscript M=measured); and
$Zsub_{DFN}=169.512+(6.668*DFN)$, where DFN=distance of the electrode from the nipple in cm.

9. A method for assessing the risk that a substantially asymptomatic female patient will be found to have proliferative or pre-cancerous changes in the breast, or may be at subsequent risk for the development of pre-cancerous or cancerous changes, said method comprising the following steps:

(A) establishing a connection between a first electrode and subepithelial parenchymal tissue in the breast of the patient;

(B) placing at least one second electrode in contact with the skin surface of the breast proximate the subepithelial tissue at a fixed distance from the nipple of the breast;

(C) establishing at least one electrical signal having a frequency between the first and second electrodes;

(D) measuring the subepithelial impedance at least one frequency between the first and second electrode;

(E) obtaining an estimate of subepithelial impedance ($Zsub_e$) of parenchymal breast tissue for the patient according to variables pertaining to the patient based on the following equation:

$$Zsub_e=107.753+(1.083*Age)+(-1.074*Breast Density)+(3.196*Body Mass Index);$$

wherein Age is measured in years; Breast Density is expressed in % and is estimated from the appearance of the breast(s) on a mammogram; and Body Mass Index, BMI, is defined as:
Wt $(lbs)*703/Height^2(inches^2)$, or
Wt $(lbs)*4.88/Height^2(ft^2)$;

(F) obtaining at least one measured value of subepithelial impedance ($Zsub_m$) of parenchymal breast tissue for the patient; and (G) calculating a value for the ratio of $Zsub_m/Zsub_e$;
wherein there is a statistically significant increased risk that the female patient will be found to have breast cancer or be at increased risk of developing breast cancer provided that the ratio of $Zsub_m/Zsub_e$ is less than about 0.8 or greater than about 1.2.

Several computer implemented methods are set forth in the following paragraphs:

10. A computer-readable medium having computer-executable instructions for performing a method for assessing the risk that a substantially asymptomatic female patient will be found to have breast cancer or be at increased risk of developing breast cancer, or may be at subsequent risk for the development of pre-cancerous or cancerous changes, the method comprising the following steps:

(A) establishing a connection between a first electrode and subepithelial parenchymal tissue in the breast of the patient;

(B) placing at least one second electrode in contact with the skin surface of the breast proximate the subepithelial tissue at a fixed distance from the nipple of the breast;

(C) establishing at least one electrical signal having a frequency between the first and second electrodes;

(D) measuring the subepithelial impedance at least one frequency between the first and second electrode;

(E) calculating an estimate of subepithelial impedance ($Zsub_e$) of parenchymal breast tissue for the patient according to input values for variables pertaining to the patient based on the following equation:

$$Zsub_e=107.753+(1.083*Age)+(-1.074*Breast Density)+(3.196*Body Mass Index);$$

wherein Age is measured in years; Breast Density is expressed in % and is estimated from the appearance of the breast(s) on a mammogram; and Body Mass Index, BMI, is defined as:
Wt $(lbs)*703/Height^2(inches^2)$, or
Wt $(lbs)*4.88/Height^2(ft^2)$;

(F) obtaining at least one measured value of subepithelial impedance ($Zsub_m$) of parenchymal breast tissue for the patient; and (G) calculating a value for the ratio of $Zsub_m/Zsub_e$;
wherein there is a statistically significant increased risk that the female patient will be found to have breast cancer provided that the ratio of $Zsub_m/Zsub_e$ is less than about 0.8 or greater than about 1.2.

11. A computer-readable medium having computer-executable instructions for performing a method for estimating the percent mammographic density (MD) of at least one breast of an individual, the breast comprising an overlying skin surface and nipple, the method comprising the following steps:

(A) establishing a connection between a first electrode and subepithelial parenchymal tissue in the breast of the individual;

(B) placing at least one second electrode in contact with the skin surface of the breast proximate the subepithelial tissue at a fixed distance from the nipple of the breast;

(C) establishing at least one electrical signal having a frequency between the first and second electrodes;

(D) measuring the subepithelial impedance (Zsub) at least one frequency between the first and second electrode;

(E) calculating an estimate of the density of the breast according to an algorithm relating Zsub to mammographic breast density estimated or calculated according to a method independent of steps (A) through (D).

12. The method according to paragraph 11 wherein the algorithm is selected from the group consisting of:

$$MD = 141.788 + (-0.716*age) + (-1.113*BMI) + (-0.199*Zsub); \quad (I)$$

$$MDpmw = 127.770 + (-1.339*BMI) + (-0.259*Zsub); \text{ and} \quad (II)$$

$$MDpstmw = 127.178 + (-0.874*Age) + (-0.219*Zsub); \quad (III)$$

wherein the symbol * indicates multiplication of the terms preceding and following the symbol; BMI=body mass index calculated as $(Wt*703)/Height^2(inches^2)$, or $(Wt*4.88/Height^2(ft^2))$ where Wt is in pounds; Zsub is expressed in ohms; age is expressed in years; MDpmw=mammographic density for pre-menopausal women; MDpstmw=mammographic density for post-menopausal women.

13. The method according to paragraph 11 wherein Zsub is adjusted for the distance that the electrode is from the nipple (ADJZsub) according to the equation:

$$ADJZsub = Zsub_M/Zsub_{DFN} \text{ (where subscript } M = \text{measured); and}$$

$$Zsub_{DFN} = 169.512 + (6.668*DFN), \text{ where } DFN = \text{distance of the electrode from the nipple in cm.}$$

14. The method according to paragraph 11 wherein Zsub is adjusted for the distance that the electrode is from the nipple (ADJZsub) and the algorithm is selected from the group consisting of:

$$MDpmw = 131.936 + (-1.444*BMI) + (-54.752*ADJZsub) \quad (I)$$

or $$MDpstmw = 120.178 + (-0.869*Age) + (-39.179*ADJZsub); \quad (II)$$

wherein
MDpmw=mammographic density for pre-menopausal women;
MDpstmw=mammographic density for post-menopausal women;
$ADJZsub = Zsub_M/Zsub_{DFN}$ (where subscript M=measured); and
$Zsub_{DFN} = 169.512 + (6.668*DFN)$, where DFN=distance of the electrode from the nipple in cm.

BRIEF DESCRIPTION OF THE DRAWINGS

The accompanying drawings, which are incorporated in and constitute a part of this specification, illustrate one embodiment of the invention and together with the description, serve to explain the principles of the invention.

DETAILED DESCRIPTION

Figure 1:
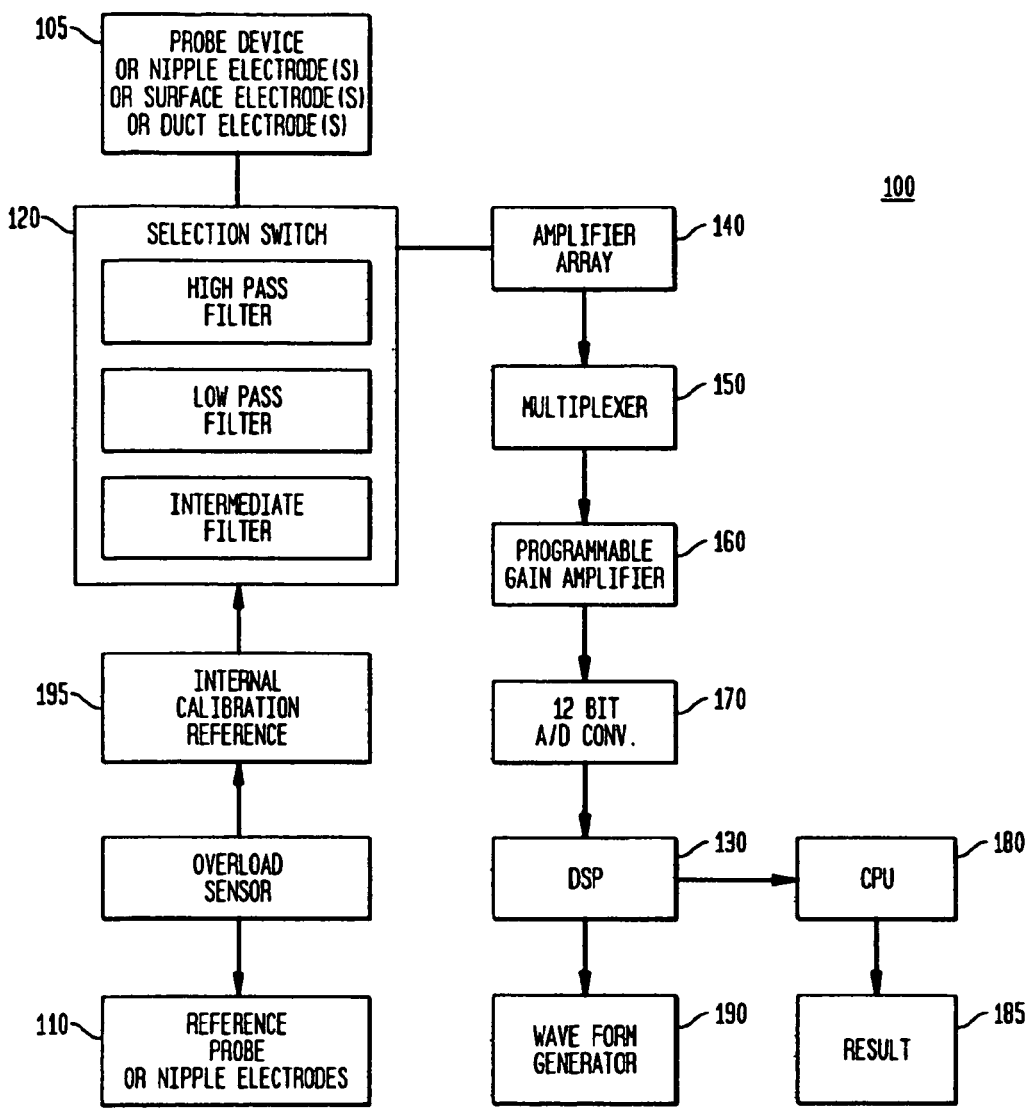
FIG. 1 is a schematic diagram of a DC and AC impedance measuring device, consistent with an embodiment of the present invention.

For purposes of the present invention the following terms have the indicated meanings:

Sub-epithelial impedance, referred to herein as Zsub, means the impedance of the breast tissue that is underneath (sub) or beyond the ducts of the breast, i.e., the stroma or mesenchymal tissue of the breast (including fat, fibroglandular tissue, etc.). At high frequencies, such as about 50 KHz to about 60 KHz and higher, the epithelia (ducts and ductal-alveolar units of the breast) and overlying skin of the breast contribute very little to the total measured impedance, so the remainder is the sub-epithelial impedance (Zsub). Technically, Zsub is defined as the impedance at infinite frequency or the highest frequency tested, provided that the frequency is sufficiently high that the dielectric properties of the epithelial breast cells and the overlying skin break down and thus do not cause the test result to differ significantly from the true value at infinite frequency or at a significantly higher frequency than used for the measurement. Typically, it is the impedance value corresponding to the point on a Nyquist plot obtained using the technology of the present invention, sometimes referred to as ductal epithelial impedance spectra (DEIS) where the curve intersects the x-axis at the highest frequency tested.

"Transepithelial impedance", in contrast to subepithelial impedance, means the impedance of the breast measured through the epithelium, i.e., through the lining or epithelia of the ducts.

"Mammographic density" (MD) means either: (1) a value calculated according to one or more algorithm described according to at least one aspect of the present invention and including a measured value of Zsub; or (2) a value derived from or based on one or more images of at least one breast of an individual obtained, for example, using X-ray, magnetic resonance imaging (MRI), computed tomography (CT or CAT) scan, dual-energy X-ray absorptiometry (DXA), tomosynthesis, ultrasound and the like. The value represents the fractional amount or percentage of breast tissue appearing to be more dense ("dense breast tissue") compared to other tissue of the same breast, such dense breast tissue typically characterized by one or more areas of increased opacity, or brightness, in an image obtained by one or more of the above-described methods. A value for mammographic density can be expressed as a fraction or percentage based on the image area or as a volumetric fraction or percentage, depending on the imaging method used, of a single breast. Alternatively, a value can be expressed as an average for both breasts of an individual. Although mammographic density and breast imaging typically refers to the female breast, the methods, tests and calculations of the present invention are not limited by gender and can be applied to both males and females.

For purposes of the present invention, reference to "dense breast tissue" can be understood from the fact that fibroglandular tissue and fat tissue present in a breast have different radiological (or MRI or ultrasound) appearances on mammograms. Fibroglandular tissue is a composite of fibrous connective tissue (the stroma), and the functional epithelial cells that line the breast ducts (the glandular component), which lines the breast and collectively is known as the parenchyma. Fat has a lower X-ray attenuation on a mammogram and appears dark compared with the fibroglandular tissue which appears bright, white or radio-opaque. The areas of brightness, whiteness or opacity, are referred to as areas of higher mammographic density which, when compared with the whole breast, exhibit a pattern of breast density or relative density of different areas of the breast.

There are several methods and classification schemes for estimating mammographic breast density using X-ray, magnetic or acoustic techniques. Most of the literature discussing breast density as a predictive biomarker has focused on subjective assessment of density, rather than numeric measures of density. The classifications are area-based as assessments are made from single view mammograms. Although the scientific literature may use the "Wolfe" and Six Category Classification (SCC), it should be noted that in clinical practice most radiologists report breast composition using the Breast Imaging Reporting and Data System, or BI-RADS classifications. It should also be noted that BI-RADS reports describe breast composition or pattern, rather than percent breast density. Composition, as described in BI-RADS, is a rough combination of pattern and density. Radiologists generally assess pattern, rather than density, as pattern is purely a subjective visual assessment and not numeric. These classification systems are discussed further hereinbelow. (Citations to references appearing below can be found in the compilation of references included at the end of the specification).

In 1976, Wolfe published his first well-known work on breast density (Wolfe 1130-37). Wolfe divided breast composition into four categories, but without the strong categorization by density implied using the BI-RADS classification scheme.

| Wolfe Pattern | Description |
| --- | --- |
| N1 | Parenchyma composed primarily of fat with at most small amounts of "dysplasia". No ducts visible. |
| P1 | Parenchyma chiefly fat with prominent ducts in anterior portion occupying up to 25% of the volume of the breast. There may be a thin band of ducts extending into a quadrant. |
| P2 | Severe involvement with prominent duct pattern occupying more than 25% of the volume of breast. |
| DY | Severe involvement with "dysplasia", often describes an underlying prominent duct pattern. |

Subsequent reviews have confirmed the association of the increasing Wolfe patterns (N1 to DY) with breast cancer (Goodwin and Boyd 1097-108; Saftlas and Szklo 146-74), and they concluded two- to three-fold risk increase between the N and DY pattern. Because it appears that the increasing amount of fibroglandular tissue is responsible for the increased risk, most of the subsequent work has focused on density rather than pattern.

The Six Category Classification, or SCC, method is based on a radiologist's assessment of the percentage of breast area considered dense (Byng, 1994). This approach utilizes an interactive thresholding technique applied to digitized film-screen mammograms, and assesses the proportion of the mammographic image representing radiographically dense tissue. Observers view images on a computer screen and select grey-level thresholds from which the breast and regions of dense (radio-opaque) tissue in the breast are identified. The proportion of radiographic density is calculated from the image histogram. The technique was evaluated in Byng's original study in mammograms from 30 women and was well correlated ($R>0.91$, Spearman coefficient) with a six-category subjective classification of radiographic density by radiologists. The technique was also considered to be very reliable with an intra-class correlation coefficient between observers typically with an $R>0.9$. It should be noted that, SCC provides non-uniform ranges for the various classifications; the quartile of density from 0-25% is divided into three classifications.

| SCC Range | Description |
| --- | --- |
| 0% | No density visible |
| 1-10% | Very limited density visible |
| 11-25% | Limited density visible |
| 26-50% | Considerable density visible |
| 51-75% | Majority of breast is dense |
| >75% | Extremely dense |

ACR BI-RAD is a further modification of the BI-RAD scheme. Radiologists practicing in the United States are required to visually assess the composition of the breasts, giving a single assessment for the patient. ACR BI-RAD is one of the methods used in the examples of the present invention for comparing and correlating Zsub with Estimated Density (ED) of the breast. ED (percent) was also determined by visually examining the X-ray mammogram and calculating the percent dense tissue compared to the total amount of breast tissue. However, it is noted that since Zsub is determined objectively and independently from a density assessment or estimate based on X-ray, MRI, ultrasound and the like, such other imaging and other assessment methods can be employed to obtain Estimated Density values.

ACR BI-RAD assessment is a combination of pattern and percent density and therefore it is somewhat arbitrary and subjective. The ACR added the requirement to report a breast density classification for each study when the BI-RADS® Atlas (the replacement for the older BI-RADS Lexicon) was published in 2003. The BI-RADS Breast Imaging Reporting and Data System, 2003, under the Chapter "Report Organization", page 179, recommends the following assessment categories:

| BI-RADS Composition | Description |
|---|---|
| 1 | The breast is almost entirely fat (<25% glandular) |
| 2 | There are scattered fibroglandular densities (approximately 25%-50% glandular) |
| 3 | The breast tissue is heterogeneously dense, which could obscure detection of small masses (approximately 51%-75% glandular |
| 4 | The breast tissue is extremely dense. This may lower the sensitivity of mammography (>75% glandular) |

Some radiologists report BI-RADS composition for each individual breast, as opposed to for the patient as a whole, as the breast density may differ from one breast to the other due to natural asymmetry, although it is usually not greater than about 5-10%. A minority of radiologists or clinical researchers report BI-RADS composition on each of the screening views.

Figure 13:
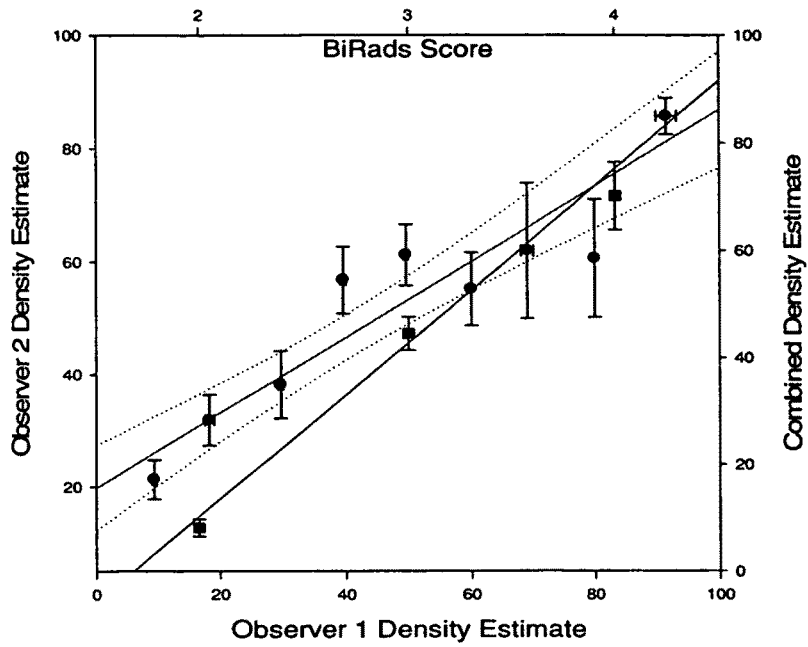
FIG. 13 illustrates the correlation of density estimate with the BI-RADS classification system for X-ray mammograms and density estimate between two observers.

FIG. 13 illustrates two methods used to estimate mammographic density, BI-RADS Score (more specifically, ACR BI-RADS) and Density Estimate based on the X-ray images. The Density Estimate was obtained from two mammographic views of one breast (CC, the craniocaudal view, and MLO, the mediolateral oblique view). The area of density was calculated as the more radio-opaque area expressed as a percent of the entire area of the whole breast. The average between the two views was then expressed as a percent density estimate. The value represents a subjective estimate of breast density and such density values have been found to correlate with breast cancer risk.

Specifically, FIG. 13 illustrates the correlation of BI-RADS score, upper x-axis, with combined density estimate (based on 2 observers) right y-axis, and the correlation is based on the data represented by the squares on the graph. The correlation of density estimate (DE) between two independent blinded observers (left y-axis, and lower x-axis), is represented by the data indicated as circles on the graph. The error bars indicate the standard error of the mean (SEM) for the density estimates or BI-RADS score measured against their respective axes. BI-RADS score tends to underestimate the DE and in the mid-range of density there is significant overlap in the DE between observers, suggesting a need for a more objective measure of density. Note that BiRad score is scaled between 2 and 4 because no examples of a completely fat replaced breast (BI-RADS score=1) were identified in this series.

Further discussion of methods for measuring breast density are covered in detail in M. Yaffe, "Mammographic Density. Measurement of mammographic density." Breast Cancer Research, 10.3 (2008): 209, incorporated herein by reference to the extent permitted. These methods are summarized below:

Qualitative density assessment methods include the six-category classification (SCC) defined above. It was the first attempt to qualitatively estimate density. It suffers from a somewhat arbitrary classification, with most of the categories being at the lower end of percent density, without an attempt to make the distribution of percent density more continuous. Qualitative methods include the breast imaging reporting and data system density categories (BI-RADS) also discussed above, and is the classification system most widely used by radiologists to estimate density in a qualitative manner (American College of Radiology). The classification is described above and it was updated in 2003 to replace the 1993 lexicon. It combines density and pattern information and remains highly subjective. It is used more to advise the clinician that other imaging modalities may be needed, particularly where a large amount of dense tissue is present, because of the nature of dense breast tissue in masking small breast cancers, and not to quantify risk (Carney et al. 168-75; Buist et al. 1432-40).

Quantitative methods can be characterized, for example, as two-dimensional and three-dimensional or volumetric methods.

Two-dimensional methods include the following:

Planimetry is a tracing technique around regions of higher density seen on a mammogram using an instrument called a planimeter. The planimeter integrates the area traced. A similar tracing is performed on the whole area of the breast excluding the pectoralis muscle when visible. The ratio of the dense area to the whole breast area is then used to estimate the percentage of higher density breast tissue (or regions). This is highly labor intensive when islands of density have to be added in to the equation and was used in the original work of Boyd (Wolfe, Saftlas, and Salane 1087-92). It also does not allay concerns that have been expressed regarding the use of two-dimensional images to obtain three-dimensional density information.

Image digitization techniques have largely replaced planimetry. Unlike planimetry, the mammographic image has to be digitized with a scanner (raster scanning) usually requiring at least 12-bit precision, the avoidance of extraneous glare light, and adequate spatial resolution. For texture estimation, resolution to 50 μm may be required (see Li et al. 863-73; Miller and Astley 277-82; Megalooikonomou et al. 651421).

Interactive threshold of digitized (X-ray) images, sometimes referred to as thresholding, requires less human interaction than planimetry, but still requires subjective decisions by the observer. The threshold of intensity (density) is selected on the digitized image and the optimal level is selected. A second threshold is selected to delineate the edge of the breast from the background, excluding the pectoralis muscle. The area of each higher intensity is then added, and ratio to the entire breast area is used to calculate the percent area of higher density on the two dimensional X-ray of the breast. The software for performing this estimate is known as the "Cumulus" program and it has been used in a number of studies (Khan et al. 1011; Vachon et al. 1382-88; Palomares et al. 1324-30; Mitchell et al. 1866-72; Gram et al. R854-R861; Buist et al. 2303-06). The two-dimensional considerations and operator decisions limit the widespread adopt-ion of this approach. Automated density measurements based on thresholding are under development, but are not yet in clinical use (Karssemeijer 365-78; Sivaramakrishna et al. 250-56; Zhou et al. 1056-69; Chang et al. 899-905; Glide-Hurst, Duric, and Littrup 4491-98).

Texture measurements on mammograms may be useful for predicting the risk of developing breast cancer and have been used by a number of investigators. Caldwell has correlated the Wolfe parenchymal pattern with the fractal dimension of the digitized mammogram (Caldwell et al. 235-47), and others have used a number of computer-calculated image texture measurements to predict risk (Magnin et al. 780-84; Li et al. 549-55; Huo et al. 4-12). None of these techniques however demonstrate greater accuracy in predicting breast cancer risk than plain or standard mammographic density measurements.

It has been recommended that three-dimensional information be used to come up with more accurate estimation of percent density since two-dimensional films or images cannot give three-dimensional density information (Kopans 348-53). With the realization that two dimensional films cannot provide accurate information about the volume of dense breast tissue in a given breast, and the probability that the risk of developing breast cancer is related to the volume of target cells (epithelium or fibroglandular tissue), increasing focus has been directed at volumetric density assessment.

Three-dimensional methods include the following:

Breast CT Scan: Volumetric radiologic density can be computed from computed tomography (CT) imaging, which is a three-dimensional reconstruction of the X-ray attenuation coefficient of a series of images presented as a series of two-dimensional planar images. The pixel images in terms of effective atomic number and electron density can be displayed continuously, or a simple binary threshold can be established to distinguish between fat-like and water-like tissue and their respective volumes. The total breast volume and the fraction of each type of tissue are then used as an estimate of volumetric breast density. Dedicated breast CT systems are now under development (Boone et al. 2185; Chen and Ning 755-70). These systems are unlikely to be used regularly for younger women because of concerns about X-ray exposure, even though breast cancer risk assessment in younger women may be particularly important. The pendant position of the breast may also introduce inaccuracies.

Breast Tomosynthesis: Probably less accurate than breast CT is tomosynthesis, because of the quasi three-dimensional images used to obtain the X-ray attenuation coefficients of the breast tissue, using a limited range of angular projections. The technique may be able to distinguish fat from fibroglandular tissue (Niklason et al. 399-406; Wu et al. 365-80).

Dual-energy X-ray absorptiometry (DXA): DXA has been adapted from bone densitometry studies to make measurements of breast density (Shepherd et al. 554-57). Instead of bone and soft tissue, transmission through the breast is measured in terms of effective thicknesses of fibroglandular tissue and fat. Two X-ray energies are used first on a breast phantom of known attenuation coefficients to calibrate against the breast and then measurements are made through the breast at high and low X-ray energies. This system gives very precise estimates of breast density, but has several disadvantages, including calibrating against a phantom or "step-wedge" and requiring a separate procedure in connection with the mammogram. However, one advantage is that X-ray exposure is low with this technique.

Digital mammography can be considered as an alternative to regular mammography discussed above. In theory digital mammogram should improve estimation of mammographic density, because of the improved quality of the signal, and because it is not necessary to first obtain a standard mammographic film image and then scan or digitize the film image. Two images are generally obtained from digital mammography equipment; the "raw-image", which contains most of the composition and density information; and the "processed-image", which optimizes the image for display, removing much of the density information. For density analysis the raw image should be used. However, this may be difficult as much of the processing software is proprietary to the digital mammography equipment manufacturers. Mammography combined with computer aided detection technology and software (Hologic/R2, Hologic, Inc.) uses a software program (Quantra™) which estimates volumetric breast density from digital mammograms; the equipment is FDA approved for obtaining volumetric density information on screening mammograms (Hartman et al. 33-39). It reverses the processing of the pixel value of the "raw-image" and creates a map of dense tissue in the breast, where each pixel value in the image is related to the height of dense tissue above that pixel, rather than to X-ray exposure. Breast density is then expressed as the volume of fibroglandular tissue to the entire breast volume. This new technology still does not avoid the problem of X-ray exposure to women under the age of 40 when breast density for breast cancer risk assessment may be particularly important.

One advantage of using non-radiation based imaging modalities for assessing breast density is that the breast is not exposed to the potential carcinogenic influences of ionizing radiation. This is of particular concern in younger women were accurate density determination for use in assessing breast cancer risk may have the most potential benefit. Such alternative modalities include:

Ultrasound: With ultrasound the images are dependent on the speed of sound waves due to tissue composition and acoustic reflections at tissue boundaries. Ultrasound images are highly operator dependent which is likely to influence the accuracy of this approach. However preliminary reports suggest that this approach can provide equivalent density information to that obtained from radiation based mammography (Graham et al. 162-68; Blend et al. 293-98; Glide, Duric, and Littrup 744-53; Duric et al. 773-85).

Magnetic Resonance Imaging (MRI): MRI also avoids the use of ionizing radiation, but its use for measuring breast density may be limited by cost and the need to administer a contrast agent (gadolinium). It provides signals that correlate with water content, which indicates the amount of fibroglandular tissue, and another signal that correlates with fat content (Lee et al. 501-06; Klifa et al. 1667-70).

Only limited studies have been performed comparing breast density measurement methods. A study comparing two-dimensional density measurements derived from qualitative, quantitative, and semi-automated methods in 65 women found large differences based on qualitative and quantitative methods, consistent with the findings of *other studies (Martin et al. 656-65; Warner et al. 67-72). Reproducibility was less in qualitative assessments and they tended to overestimate the degree of density. Limited comparisons have been made between area-based and volumetric-based methods and despite the theoretical advantage of volumetric-based approaches, it was less reliable than a threshold-based two-dimensional assessment (The quantitative analysis of mammographic densities. Byng, J. W. et al. Phys Med Biol (1994) 39:1629-1638), possibly because of the difficulties involved in estimating breast thickness (McCormack et al. 1148-54). The volumetric approach also failed to provide a more accurate predictor of breast cancer risk (Ding et al. 1074-81).

The electrical impedance approach described in the present application is the only non-imaging technology described in the reviewed literature (apart from DXA, which relies on X-ray). Furthermore, the technology described herein provides an objective measure of breast density, which highly correlates with the standard clinical assessments of mammographic density and provides a volumetric measure of density based on the conductive properties of breast tissue.

One of the hallmarks of cancer is the loss of cell to cell communication, which is thought to be mediated by gap-junctions; this process is also referred to as gap-junction intercellular communication (GJIC). Connexins are protein channels that permit the passage of ions and small molecules between adjacent cells and are down-regulated during cancer development. Furthermore, gap-junction function and intercellular communication can be probed using electrophysiological and bioelectrical impedance methods. According to the present invention, altered intercellular communication can be probed in breast parenchyma using modifications of bioelectrical impedance analysis techniques.

Biological impedance analysis (BIA) has been used clinically to measure body composition (see, for example, a review by U. G. Kyle et al., 2004, Bioelectrical impedance analysis, Parts I and II, Clin. Nutr. 23:1226-43 and 1430-53). Although cancer cachexia (protein loss), dehydration, fat free mass, etc. have been estimated in cancer patients the methods of the present invention, particularly segmental bioelectrical impedance methods, have not been used for estimating percent mammographic breast density and/or assessing the risk that a patient will be found to have proliferative or pre-cancerous changes in the breast or of developing breast cancer. Segmental-BIA refers to the placement of sensor electrodes over or on the body part of interest, the breast for example, unlike whole body BIA where typically measurements are made between the hand and the foot to estimate body composition, and tend to overestimate the contribution of some body parts (for example, the arm) and underestimate the contribution of others (for example, the trunk), because of the low and high cross-sectional area of each, respectively.

Non-invasive electrical approaches may be used to characterize breast epithelia, which can then be modeled as an electrical circuit with resistors and capacitors in series and parallel. Depending on the frequency of the interrogating electrical signal, the high impedance of the skin can obscure the dielectric and resistance properties of the underlying ductal epithelia. Other approaches using electrical or impedance techniques to characterize breast tissue, do not probe the ductal epithelium, where breast cancer originates, or deal with the high impedance of the skin that obscures the underlying tissue. Therefore, the present inventor developed and previously disclosed a new technique, referred to as ductal epithelial impedance spectroscopy (DEIS). DEIS avoids the problem of high impedance of the overlying skin and which can be used to non-invasively probe the ductal epithelium in order to characterize the electrical signature of breast ductal epithelia during menstrual cycle as well as in the course of proliferative or pre-cancerous changes in the breast, which can lead to breast cancer. In addition, by applying DEIS measurements through the ductal system of the breast at sufficiently high frequencies, the obscuring impedance of the ductal system and overlying skin may be eliminated so that the sub-epithelial impedance characteristics of the breast parenchyma and/or stroma can be measured.

For purposes of the present invention and as understood by those skilled in the art, reference to stromal tissue and parenchymal tissue are the same and are used interchangeably. In the context of the breast, the terms are intended to refer to any non-epithelial tissue, and include mesenchymal cells, adipose (fat) cells, fibroblasts, connective tissue etc. The stromal or parenchymal tissue is rich in growth factors, * and may be associated with breast density seen on mammograms. Growth factors through paracrine mechanisms and gap junctions communicate with the epithelial cells forming the breast ducts stimulating proliferation. Upon application of a high frequency electrical current/voltage, impedance (capacitive reactance) of the skin and ductal epithelium of the breast break down so the residual or observed impedance is due to the impedance of the stromal/parenchymal tissue. At the high frequency current passes both through and between the cells and impedance is dominated by the total cell mass of the breast, i.e. the stromal/parenchymal cell mass. In contrast, at low frequency most of the impedance is due to the overlying skin and the epithelial cells lining the ducts, and their tight junctions. Typically, current will pass both through and between the epithelial cells at high frequency, but since the epithelium is only one or two cell layers in thickness, its contribution (without the dielectric properties of the epithelial cell membranes, which break-down at high frequency) is negligible. The parenchymal/stromal cell mass, which comprises most of the breast tissue mass, passes current at high frequency between cells and from cell to cell, so that the total impedance is considered a function of intracellular and extracellular fluid, but may also be related to gap-junction function. Gap-junctions permit the passage of small substances, ions and electricity between cells; such junctions have been found to break down during the carcinogenic process.

For purposes of the present invention, one aspect of electrical resistance to the flow of electrical current through biological tissues is referred to as bioimpedance. The impedance of a simple resistor can be measured using a direct current (I) and is related to voltage by V=IR (Ohm's law). In biological tissues, cell membranes act as insulators and only allow an electrical current to pass along the low impedance pathway. In the case of the breast, using a preferred method of the present invention, (see, for example FIG. 6), the low impedance pathway is between the nipple sensor electrode, across the duct ostia, along the larger collecting ducts, between the ductal epithelial cells (tight-junctions/paracellular pathway), across the breast parenchyma and skin to the surface electrode. At the preferred higher frequencies of the present invention, typically about 40 KHz to about 80 KHz, preferably about 50 KHz to about 60 KHz, it is predominantly the breast parenchyma that is probed, and not the ductal epithelium. Alternatively, when an alternating current is applied to the ductal system, for example as a series of different frequency sine waves, more of the current passes to the terminal duct at the lower frequencies. Conversely, at higher frequencies more of the current passes through the cells, and does not reach the terminal ducts. The present invention probes or "interrogates" breast tissue using alternating current at higher frequencies in order to estimate density and density changes in the breast parenchyma associated with an increased risk of proliferative or pre-cancerous changes in the breast or an increased risk of breast cancer.

As noted above, at high frequencies, which, for purposes of the present invention are frequencies such as about 50 KHz to about 60 KHz, when current is passed through the ductal system of the breast, most of the current passes through the parenchymal or stromal tissues of the breast, because the dielectric properties of the skin and ductal epithelium break down. The high frequency impedance or resistance measurement is then a measure of intracellular and extracellular fluid and intercellular communication or gap-junction function.

Figure 6:
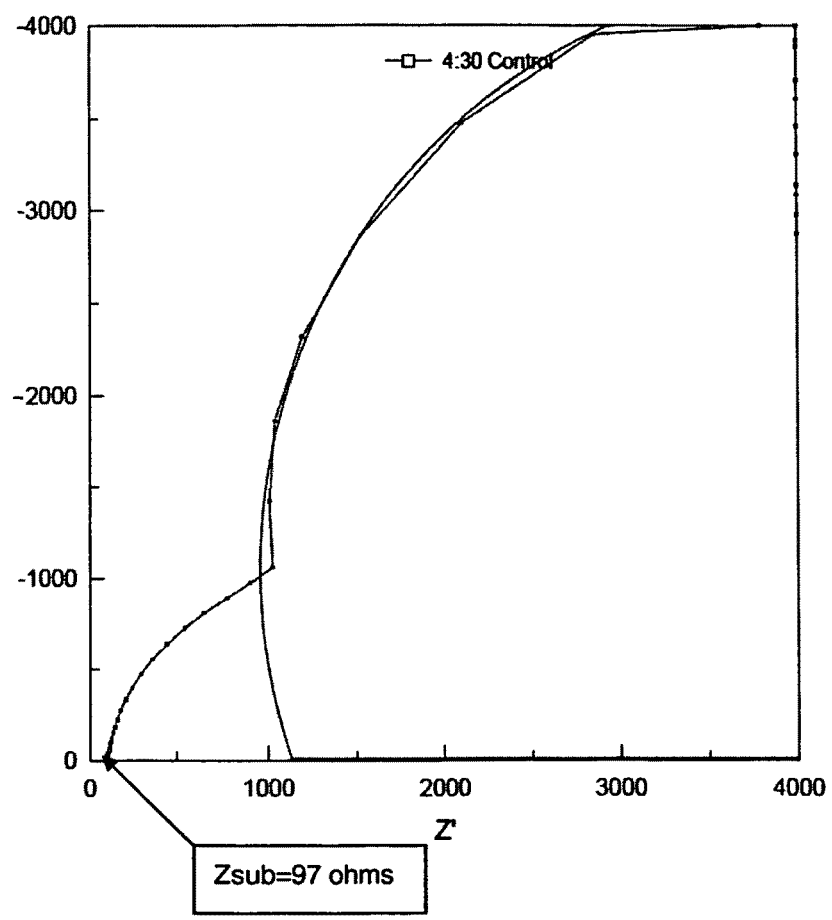
FIG. 6 illustrates a Nyquist plot for the measurement of subepithelial impedance (Zsub) based on ductal epithelial impedance spectra.

For purposes of the present invention it is preferable to make the electrical measurements through the breast ductal system, i.e. utilizing a nipple sensor as previously described by the inventor, because the parenchyma surrounding the ductal network may not be probed when measurements are made through the skin alone. Such measurements are then used to obtain reliable measured values of subepithelial impedance (Zsub) or subepithelial resistance (Rsub); such measurements are typically unreliable when a nipple sensor is not used. In a copending patent application of the present inventor, published as U.S. 2004/0253652, the disclosure of which is incorporated herein by reference, there is disclosed a method and system for determining a condition of a selected region of epithelial and stromal tissue in the human breast. The nipple sensor generally described therein is also useful. That method uses a plurality of measuring electrodes to measure the tissue and transepithelial electropotential of breast tissue. Surface electropotential and impedance are also measured at one or more locations. An agent may be introduced into the region of tissue to enhance electrophysiological characteristics. The condition of the tissue is determined based on the electropotential and impedance profile at different depths of the epithelium, stroma, tissue, or organ, together with an estimate of the functional changes in the epithelium due to altered ion transport and electrophysiological properties of the tissue. A nipple cup sensor is described as an apparatus for determining the condition of a region of tissue comprising: a cup having an interior, and first and second openings; an electrode disposed within the interior; and a source of suction connectable to the first opening; and wherein the second opening is placed over a region of tissue and suction is applied to the first opening and an electrical connection is made between the region of tissue to be examined and the electrode. The invention of the copending application provides for methods for determining a condition of a region of epithelial breast tissue or the location of a tumor in an organ, for example, the breast, comprising: establishing a connection between a first electrode and the epithelial tissue of a breast; placing a second electrode in contact with the surface of the breast; establishing a signal between the first and second electrodes; measuring at least one electrical property between the first and second electrode; and determining the condition of a region of epithelial tissue or the location of a tumor based on the signal between the first and second electrode. A plurality of electrical properties can be measured including, for example, impedance measured at at least two different frequencies. Such methods and devices, adjusted to account for the specific requirements of the present invention as described, can also be useful. For example, as noted above, a higher alternating current electrical signal frequency is preferred in the present invention, and a syringe, or automated vacuum pump, can be operatively connected to the nipple cup sensor in order to provide a source of suction as well as to deliver an electroconductive medium (ECM) to facilitate improved electrical contact (FIG. 6).

In the descriptions that follow, reference is made to an "organ." For purposes of the present invention, an "organ" refers to a relatively independent or differentiated part of the body or collection of tissues that carries out one or more special functions. Organs are generally made up of several tissue types, one of which usually predominates and determines the principal function of the organ. Major organ systems, particularly of the human body, comprise: circulatory system including the lungs, heart, blood, and blood vessels; digestive system including the salivary glands, esophagus, stomach, liver, gallbladder, pancreas, intestines, rectum, and anus; endocrine system including the hypothalamus, pituitary or pituitary glands, including the anterior and posterior pituitary glands, pineal body or pineal gland, thyroid, parathyroids, and adrenals or adrenal glands; integumentary system including skin, hair and nails; lymphatic system including the lymph nodes and vessels that transport lymph; immune system including tonsils, adenoids, thymus, and spleen; muscular system including the various muscles; nervous system including the brain, spinal cord, peripheral nerves, and nerves; reproductive system including the sex organs, such as ovaries, fallopian tubes, uterus, vagina, breasts, mammary glands, testes, vas deferens, seminal vesicles, prostate, and penis; respiratory system including the organs used for breathing, such as the pharynx, larynx, trachea, bronchi, lungs, and diaphragm; skeletal system including bones, cartilage, ligaments, and tendons; and urinary system including kidneys, ureters, bladder and urethra. The present invention is preferably directed to electrophysiological measurements and characteristics relating to the breast.

The present invention overcomes problems and inadequacies associated with prior methods used for characterizing abnormal or cancerous epithelial tissue. In summary, various embodiments of the present invention measure impedance, primarily subepithelial impedance, $Z_{sub}$, although if desired DC measurements can also be made, under ambient and/or variable suction, by passing an electrical current or signal across the breast epithelium using specially constructed electrodes. For example a nipple electrode is preferably used to measure the voltage and/or impedance between ductal epithelium, surrounding breast tissue, skin and surface or other electrode. The nipple electrode may also be used to pass the current along the ductal system of the breast. Another type of electrode may be used to measure the voltage and/or impedance signal, and/or pass a current and measure the signal at the individual ductal orifices at the nipple surface. Another type of electrode may be used to measure the voltage and/or impedance signal, and/or pass a current and measure the signal within individual ducts using a modified ductal probe or ductoscope which may have one or more electrodes attached to it. All of these electrodes may be used individually, in combination with one another, and/or in combination with a surface probe or electrodes. DC measurements can provide information about the functional state of the epithelium and can detect early pre-malignant changes and an adjacent malignancy. In particular, impedance measurements at several frequencies in specifically defined ranges using differently spaced electrodes can provide depth and topographic information to give both structural (high frequency range) and functional (low frequency range) information about the tissue being probed; as noted above, higher frequency measurements are particularly preferred.

The present inventor has previously disclosed that abnormal or cancerous tissue can be detected and characterized by detecting and measuring transport alterations in epithelial tissues, using ionic substitutions and/or pharmacological and hormonal manipulations to determine the presence of abnormal pre-cancerous or cancerous cells. A baseline level of transepithelial DC potential, impedance or other electrophysiological property that is sensitive to alterations in transport in epithelia is measured in the tissue to be evaluated. An agent may be introduced to enhance the transport or make it possible to detect the transport alteration. The transepithelial DC potential and/or impedance of the tissue (or other electrophysiological property that may reflect or make it possible to detect alterations in the transport) are then measured. Based on the agent introduced and the measured electrophysiological parameter, the condition of the tissue is determined. In contrast, the methods of the present invention measure subepithelial impedance at high frequency and use the measured value according to an algorithm developed by the present inventor so as to obtain a value for breast density which can be used to assess the risk that the patient, including one that may be asymptomatic, may develop (or possibly have) proliferative or pre-cancerous changes in the breast.

A method and system are provided for measuring the subepithelial impedance, $Z_{sub}$, of breast tissue, calculating an estimated mammographic breast density value and for an improved method for assessing the risk that a patient, particularly one who is a substantially asymptomatic female, will be found to have proliferative or pre-cancerous changes in the breast. For example, one or two current-passing electrodes can be located in contact with a first surface of the selected region of the tissue. Alternatively the current passing electrodes may pass current across the tissue or epithelium, as for example between the nipple ducts, ductal lumen, epithelium, breast parenchyma and surface of the breast. Alternatively, the ducts may be accessed by a central duct catheter or ductoscope. A plurality of measuring electrodes are located in contact with the first surface of the breast as well. One or more of the measuring electrodes can be used to measure the DC potential referenced to another electrode, or reference point. A signal is established between the current-passing electrodes. Impedance, associated with the established signal, is measured by one or more of the measuring electrodes. Alternatively, a three-electrode system may be used for measurements whereby one electrode is used for both current injection and voltage recording. If desired, an agent can be introduced into the region of tissue and the condition of the tissue further determined in response to the effect of the agent, including measured DC transepithelial potential, impedance or other electrophysiological characteristic. The electrodes in the described methods and apparatus can be used in contact with, in proximity to, over, or inserted into the tissues being examined. It should be understood that where the method is described in an embodiment as encompassing one of these arrangements, it is contemplated that it can also be used interchangeably with the other. For example, where the method is described as having an electrode in contact with the tissue, the method can also be used with the electrode inserted into or in proximity to the tissue. Similarly, where the method is described as having an electrode in proximity to the tissue, it is contemplated that the electrode can also be in contact with or inserted into the tissue.

Thus, systems and methods consistent with the present invention use impedance measurements, optionally in combination with other electrical properties such as transepithelial electropotential, to estimate breast density and/or to assess risk as described above. Further, systems and methods consistent with the present invention use preferred frequencies in order to obtain the desired value or values of subepithelial impedance required for the algorithm used to obtain an estimated mammographic density and/or to assess risk, as further described below. By using spaced electrodes, specifically in relation to the distance from the nipple, the method of the present invention provides the impedance data for calculation or estimation of mammographic density and/or assessment of breast cancer risk.

As discussed hereinabove, generally accepted methods for measuring breast density suffer from several drawbacks including, for example, the use of ionizing radiation such as X-rays which subject a patient to the risk of tissue damage and possibly cancer, methods such as magnetic resonance imaging (MRI), which are sufficiently expensive as to preclude their use on a regular or periodic basis, and methods that generally require subjectivity by the operator or in the interpretation of the results, such as the interpretation of X-ray mammograms and ultrasound scans. In contrast, the methods of the present invention are inexpensive and non-invasive and the electrical measurements, such as Zsub, are objective. Consequently, the methods can be applied serially and frequently so that a patient can be monitored if a suspicious condition is found. Furthermore, the test methods can be used to identify a change in the condition of breast tissue that may signal increased risk of abnormal tissue, thus warranting the use of one or more expensive, risky or invasive procedures in order to obtain specific, localized results, including for example, an MRI or a biopsy.

In order to measure the transepithelial or subepithelial breast impedance or DC potential it is necessary that the lumen of the duct be electrically accessed by a nipple electrode constructed to make an electrical connection between the Ag/AgCl (or similar low offset platinum/hydrogen, titanium, tin-lead alloy, nickel, aluminum, zinc, carbon, or other conductive metal or conductive polymer electrode) pellet recessed within the nipple cup. The cup is filled with an ECM (electro-conductive medium), which establishes electrical contact with the ductal system passively, or after aspiration with a syringe or pump. At least one surface electrode, preferably two or more surface electrodes as described below, placed at the surface of the breast completes the electrical circuit, so that measurements of transepithelial impedance or potential may be made between the ductal epithelium and the skin surface. In measuring the transepithelial or subepithelial AC impedance the measuring electrodes measure the voltage drop and phase shift across the ductal epithelium, by utilizing a nipple electrode, preferably the nipple cup electrode described, in combination with a skin surface electrode. Other configurations of this approach are more invasive, whereby measurement can be made between an electrode inserted via a ductoscope or nipple duct probe electrode referenced to the skin or an IV (intravenous), intradermal, or subcutaneous electrode. In another embodiment, the duct may also be accessed by a needle-electrode inserted through the skin.

In order to combine DC transepithelial measurement with impedance measurements, it is necessary to obtain baseline measurement of the DC potential using the voltage sensing electrodes, referenced to surface electrode with low-contact impedance, or the blood stream via an IV, or the interstitial body fluid via a needle electrode or electrode that permeabilizes the overlying epidermis or other epithelium, or other body reference point. The electrodes may contain different ionic concentrations, pharmacological agents or hormones in their ECMs. As used in this description, an ECM is a medium that permits transmission of electrical signals between the surface being measured and the electrode. An agent includes any ionic concentration, pharmacological agent, hormone or other compound added to the ECM or otherwise introduced to the tissue under investigation, selected to provide further information about the condition of the tissue, if desired. In another embodiment the concentrations of agents may be changed using a flow through system.

Electroconductive media or ECM can include conductive fluids, creams or gels used with external or internal electrodes to reduce the impedance (resistance to alternating current) of the contact between the electrode surface and the skin or epithelial surface. In the case of DC electrodes it is also desirable that the ECM results in the lowest DC offset at the electrode surface, or an offset that can be measured. The ECM will often contain a hydrogel that will draw fluid and electrolytes from deeper layers of the skin to establish electrical contact with the surface electrode. Electrodes that are used to pass current require ECMs with high conductance. Usually this is accomplished by using ECMs with high electrolyte content. The electrolytes frequently used are KCl (potassium chloride) because of the similar ionic mobility of these two ions in free solution, so that electrode polarization is less of a problem than when ions of different mobility are used. Other ions such as sodium may be used in ECM formulations, and the higher electrolyte concentration result in more rapid electrode equilibration.

In situations where estimations will be made of the permeability of the epithelium to specific ions, the concentration of K (potassium) in the ECM will be varied so that the conductance of the epithelium to potassium may be measured electrophysiologically. An enhancer or permeant may be added to the ECM to increase the conductance of the underlying skin to the electrolyte in the ECM. Other approaches to improving electrical contact and/or reducing surface skin impedance include mild surface abrasion with pumice and alcohol to reduce surface skin resistance, abrasive pads such as Kendall Excel electrode release liner (Tyco Health Care, Mansfield, Mass.), 3M Red Dot Trace. Prep (3M Corporation, St. Paul, Minn.), cleaning the skin with alcohol, an automated skin abrasion preparation device that spins a disposable electrode to abrade the skin (QuickPrep system, Quinton, Inc., Bothell, Wash.), ultrasound skin permeation technology (SonoPrep, Sontra Medical Corporation, Franklin, Mass.; U.S. Pat. No. 6,887,239, Elstrom et al.), or silicon microneedle array electrodes, which just penetrate the stratum corneum to reduce skin surface resistance. (See, for example, P. Griss et al., IEEE Trans. on Biomedical Eng., 2002, 49 (6), 597-604) (For a comparison and discussion of several methods see also, Biomedical Instrumentation & Technology, 2006; 39: 72-77. The content of the patent and journal documents are incorporated herein by reference).

Transepithelial electrical measurements typically require the positioning of electrodes on either side of an epithelium to make accurate measurements. This can be accomplished with an electrode placed in the lumen of an epithelial lined organ (stomach, colon, prostate, bronchus or breast) and with the reference electrode placed outside the lumen of the organ under study. Alternatively the intra- and extra-luminal electrodes can make indirect contact with the inside and outside surface of the epithelium using an electrolyte solution, gel, hydrogel or other electroconductive media.

Attempts to measure the transepithelial electrical properties of an epithelium without access to both sides of the epithelium may introduce significant sources of measurement error. For example placing a skin electrode over an epithelial lined organ such as stomach, colon, prostate or breast may result in a surface measurement that does not accurately reflect the transepithelial electrical properties of the underlying epithelium.

Application of a voltage, for example to a surface, produces an electrostatic field, even if no charge carriers move, that is, no current flows. As the voltage increases between two points separated by a specific distance, the electrostatic field becomes more intense. As the separation increases between two points having a given voltage with respect to each other, the electrostatic flux density diminishes in the region between them. This relationship is described by Coulomb's law, which is an inverse-square relationship indicating the magnitude and direction of electrostatic force that one stationary, electrically charged object of small dimensions (ideally, a point source) exerts on another. Coulomb's law may be stated as follows:

"The magnitude of the electrostatic force between two point charges is directly proportional to the magnitudes of each charge and inversely proportional to the square of the distance between the charges."

In the case of the voltage across an epithelium the value would be dependent on the charge across the epithelium which is usually due to a negative charge on the luminal side relative to the abluminal side of the epithelium. The greater the distance of a measuring electrode from the source of the charge the lower the measured electrostatic force. Mathematically, Coulomb's law may be stated as follows:

$$F = k \cdot [Q_1 \cdot Q_2]/d^2$$

Where $Q_1$ represents the quantity of charge on object 1 (in Coulombs), $Q_2$ represents the quantity of charge on object 2 (also in Coulombs), and d represents the distance of separation between the two objects (in meters). Also, k is the proportionality constant known as Coulomb's law constant, which depends on the medium between the charges and is approximately $9.0 \times 10^9$ $Nm^2/C^2$ for air and two orders of magnitude lower for water or saline.

It follows from the Lorentz Force Law that the magnitude of the electric field E created by a single point charge q is:

$$|E| = \frac{1}{4\pi\epsilon_0} \frac{|q|}{r^2}$$

For a positive charge q, the direction of E points along lines directed radially away from the location of the point charge, while the direction is the opposite for a negative charge; E is expressed in units of volts per meter or Newtons per Coulomb.

Simply stated this means that the further away from the point charge, the measured voltage falls off as an inverse function of the square of the distance from the source to the measuring electrode. Even when the impedance of the skin surface is reduced, the measured voltage with surface electrodes falls off significantly with increasing distance away from the epithelium. If a working electrode makes direct or indirect contact with luminal surface of the epithelium then the voltage measured at the skin surface will represent the voltage across the epithelium in series with the voltage drop between the outside (abluminal) surface of the epithelium and the interstitial space, and the voltage drop across the skin.

When contact is established with the luminal surface of the epithelium, directly or indirectly, with a measuring electrode and the skin surface impedance is reduced, the measurement between the luminal electrode and the skin surface more accurately represents the true transepithelial potential. This is because the voltage drop and electrical potential across the skin is partially eliminated. The voltage drop due to the interstitium, or interstitial tissue beneath the skin surface and the abluminal surface of the epithelium, is generally considered negligible. In other words, once high skin impedance is substantially eliminated, the underlying tissue has a minimal influence on the measured transepithelial DC potential and epithelial impedance, which are measurements of particular interest.

U.S. Pat. No. 6,887,239 (Elstrom, et al.) proposes use of sonophoresis to reduce the impedance of the skin to non-invasively prepare cells, tissues, and organs for transmission and reception of electrical signals. The term "sonophoresis" typically refers to ultrasonically enhanced transdermal drug delivery. For purposes of the present invention, sonophoresis refers not only to transdermal delivery of one or more compounds (for example, generally any pharmacological agent, including a drug, a hormonal agent, a solution of defined ionic composition, and the like), but more broadly to the application of ultrasonic energy to the skin surface in order to obtain a beneficial effect, including in particular, the improved measurement of electrophysiological characteristics, preferably in connection with measuring physical characteristics of an individual, especially the tissue or organ of such an individual. As stated above, reduction or even elimination of surface skin impedance by itself will not correct for the effect of Coulomb's Inverse Square Law or the Lorentz Force Law. Without an intraluminal measurement electrode or an indirect connection with the lumen of the organ under test, a surface electrical measurement will not accurately reflect the true transepithelial electrophysiological measurement.

Whereas transepithelial electrical measurements have been described in the colon, stomach, uterine cervix and other hollow organs, measurement of transepithelial electrical characteristics in the ductal epithelium of the breast (and other less "accessible" organs) are more challenging. While access to the ductal lumen may be obtained using ductal probes, catheters or ductoscopes, these approaches are invasive which can limit their utility. In contrast, the present invention provides a non-invasive approach, which uses a modified Sartorius nipple aspirator cup, described herein (also see, e.g., U.S. Pat. No. 3,786,801, Sartorius, and FIG. 4 herein). In a preferred method, the nipple is prepped with a dekeratinizing agent to remove keratin plugs that may be present, which can block the duct ostia. The cup is filled with an electroconductive medium such as physiological saline and placed over the nipple. The cup is aspirated several (e.g., about 4-5) times to remove air and/or air bubbles and to establish electrical contact between two Ag—AgCl electrodes within the nipple cup and the ductal epithelium via the physiological saline electroconductive medium. One of the two electrodes is used to measure the voltage between the ductal lumen and a skin surface electrode and the other nipple electrode is used to pass a current between the ductal lumen and a different skin surface electrode. Using this approach one can measure the transepithelial electropotential and the impedance and/or impedance spectrum (e.g., as a function of frequency) of the ductal epithelium and the breast parenchyma.

A combination of transepithelial measurements and reduction of skin and series resistance along the lumen of epithelial lined hollow organs permits more accurate and more effective measurement of the transepithelial electrical properties of an organ than using either approach alone. For example, where small differences in electrophysiological characteristics are present, application of the combined technology described herein may provide the sole opportunity to observe the desired response in order to diagnose the condition of the tissue. In various embodiments, this can be accomplished by the use of one or more of the following elements or features in combination:

(A) high conductance electrolytes in the nipple cup sensor (of particular value for establishing electrical contact with the ductal epithelium);
(B) dekeratinizing agents to reduce the impedance across the nipple;
(C) high conductance electrolytes within the ductal lumen;
(D) ductal catheters or probes to directly establish contact with the ductal epithelium;
(E) sonophoresis to reduce overlying skin impedance;
(F) skin permeants or "wetting agents" to reduce skin impedance (e.g. sodium lauryl sulfate);
(G) adhesive tape to strip away the stratum corneum;
(H) skin abrasion to reduce skin impedance (e.g., Kendall Excel electrode release liner, Tyco Health Care, Mansfield, Mass.; 3M Red Dot Trace Prep, 3M Corporation, St. Paul, Minn., or QuikPrep System, Quinton Inc, Bothell, Wash.);
(I) Hydrogel or hypertonic gel electrodes to hydrate the skin and reduce skin impedance;
(J) surface microinvasive electrodes to reduce skin impedance as described by P. Griss et al., "Characterization of micromachined spiked biopotential electrodes," IEEE Trans Biomed Eng. 2002 June; 49 (6):597-604 (also referred to as microneedles or micro-electro-mechanical systems, MEMS); and/or
(K) needle electrodes to penetrate the skin.

To the extent that sonophoresis is used in connection with the present invention, it refers to the application ultrasonic energy via a coupling medium in order to modify the properties of skin, preferably to reduce the skin's electrical impedance and improve the diagnostic methods of the present invention. For a detailed disclosure of the use of sonophoresis relating to, for example, the measurement of subepithelial impedance by the inventor herein, refer to copending patent application by the inventor herein, U.S. Ser. No. 11/879,805, filed Jul. 18, 2007, the disclosure of which is incorporated herein by reference. A particularly useful sonophoresis device is commercially available from Sontra Medical Corporation, Franklin Mass., under the brand name SonoPrep® System and in which the sonophoresis voltage is 12 V AC at 55,000 Hz and the sensor signal is 100 mV AC at 100 Hz.

However, for purposes of the present invention sonophoresis is typically not required where electrical measurements are preferably made at higher frequencies, including for example frequencies above about 5 KHz to about 10 KHz; for example at about 40 KHz to about 80 KHz, more preferably about 50 KHz to about 60 KHz, since the dielectric properties of the skin break down at higher frequencies. When measurements are to be made at lower frequencies, including those approaching zero, in other words, DC measurements, then sonophoresis and/or other methods noted above such as a microneedle electrode, is desirably used to reduce electrical interference from the skin surface.

A particularly preferred embodiment employs a working electrode that makes direct or indirect contact with the luminal epithelium referenced to a skin surface electrode combined with one or more of the techniques described above will give a more accurate transepithelial measurement than a surface electrode that is not referenced to an electrode that is in direct or indirect contact with the luminal epithelium. The improved measurement methods of the present invention, utilizing in particular the transepithelial and subepithelial electrical properties of an epithelial lined organ, may be used to measure, characterize, assess the risk for or assist in diagnosing epithelial disease states such as cancer, pre-cancerous conditions including, for example, polyps, papillomas, hyperplasia, dysplasia, aberrant colonic crypts, intraepithelial neoplasia, leukoplakia, erythroplakia and the like, as well as benign neoplastic processes of epithelial origin, inflammation, infection, ulceration and the like.

Preferably, the disclosure herein provides improved methods for estimating percent mammographic breast density and/or assessing the risk that a patient will be found to have proliferative or pre-cancerous changes in the breast; particularly a substantially asymptomatic female patient. The methods described herein are suitable for estimating mammographic density and/or assessing breast cancer risk for patients that exhibit as well as those that do not exhibit proliferative breast disease. Proliferative disease can be either benign or malignant. However, even benign proliferative disease, including for example hyperplasia, atypical ductal hyperplasia, atypical lobular hyperplasia, papillomatosis, lobular neoplasia etc., can indicate an increased risk of breast cancer after longer term or extended follow-up. Some patients may later be found to have non-proliferative benign conditions in follow-up biopsies, such as fibrocystic disease (FCD), fibroadenoma, etc.

Thus, using the methods of the present invention it is possible to detect proliferative, abnormal pre-cancerous or cancerous tissue while the development of such tissue is at an early stage. Generally, the methods and systems of the present invention are applicable to any epithelial derived cancer, such as, but not limited to, prostate, colon, breast, esophageal, and nasopharyngeal cancers, as well as other epithelial malignancies, such as lung, gastric, uterine cervix, endometrial, skin and bladder even though the methods are described specifically with regard to the breast.

Specifically, using the methods of the present invention the changes to measured values of subepithelial impedance that meet the criteria of the algorithm described below can suggest that they are a consequence of an early mutation, affecting a large number of cells (i.e., a field defect). Thus, they may be exploited as biomarkers for determining which patients should be either more frequently monitored, or conversely, possibly to identify particular regions of epithelium that require biopsy. The latter is especially helpful in the case of atypical ductal hyperplasia or ductal carcinoma in situ (DCIS), which are more difficult to detect mammographically, such as with the use of an X-ray based mammogram, or by clinical breast examination without having to resort to an invasive biopsy.

The methods of the present invention are particularly useful when impedance measurements are made at frequencies sufficiently high so that the dielectric properties of the cells lining the ducts and ductal-alveolar units of the breast, i.e., the breast epithelium, and the overlying skin of the breast, break down and do not significantly influence the measured value of subepithelial impedance or Zsub. There is very little increase in the observed or measured capacitive reactance using the methods of the present invention until measurements are made at a frequency of less than about 5 KHz. Preferably, impedance is measured at one or more frequencies including about 5 KHz to about 100 KHz; for example, about 8,000 Hertz to about 90,000 Hertz; or about 10,000 Hertz to about 80,000 Hertz, or to about 70,000 Hertz, or to about 60,000 Hertz. For purposes of measuring Zsub and obtaining a corresponding value for breast density according to one or more algorithms of the present invention, suitable measurements of Zsub can be made at frequencies between about 10 KHz and about 100 KHz, including, for example measurements at least one frequency selected from the group consisting of about 10 KHz, about 20 KHz, about 30 KHz, about 40 KHz, about 50 KHz, about 60 KHz, about 70 KHz, about 80 KHz, about 90 KHz, and about 100 KHz. Particularly useful observations in this regard can be made at, for example, about 50 KHz or about 60 KHz. Alternatively, useful information can be obtained at frequencies in the range of about 10 KHz to about 100 KHz; such as about 20 KHz to about 90 KHz; or about 30 KHz to about 80 KHz; for example about 40 KHz to about 60 KHz. Furthermore, when obtaining measurements at such higher frequencies the use of sonophoresis is optional and measurements can be made with or without the use of sonophoresis as a prelude to obtaining electrophysiological properties.

A number of variations are possible for devices useful with the present invention. Further, within a device design, there are a number of aspects that may be varied. These variations, and others, are described below.

One probe or other device includes a plurality of miniaturized electrodes in recessed wells. Disposable commercially available silicon chips processing functions, such as filtering, may perform surface recording and initial electronic processing. Each ECM solution or agent may be specific to the individual electrode and reservoir on the chip. Thus, for one measurement, a particular set of electrodes is used. For another measurement, for example, at a different ionic concentration, a different set of electrodes is used. While this produces some variations, as the electrodes for one measurement are not located at the same points as for another, this system provides generally reliable results.

An alternative approach is to use fewer electrodes and use a flow-through or microfluidic system to change solutions and agents. Specifically, solutions or agents are changed by passing small amounts of electrical current to move solution or agent through channels and out through pores in the surface of the probe. In this embodiment, the electrode remains in contact with the same region of the skin or ductal epithelium, thus eliminating region-to-region variation in measurement. This approach requires time for equilibration between different solutions.

In detecting the presence of abnormal pre-cancerous or cancerous breast tissue, a hand-held probe is provided for obtaining surface measurements at the skin. The probe may include electrodes for passing current as well as for measuring. An impedance measurement may be taken between the nipple cup electrode and the hand-held probe, or may be taken between electrodes on the hand-held probe. Alternatively, a ductoscopic or non-optical ductal probe may be interfaced with one or more miniaturized electrodes. After taking initial DC measurements, a wetting/permeabilizing agent may be introduced to reduce skin impedance or one of the methods described hereinabove may be used. The agent may be introduced using a microfluidic approach, as described above, to move fluid to the surface of the electrodes. Alternatively, surface electrodes that just penetrate the stratum corneum may be used to decrease impedance.

Regardless of the configuration of the device, FIG. 1 is a schematic of a DC and AC impedance measurement system 100 used in cancer diagnosis, consistent with the present invention. The system 100 interfaces with a probe device 105 including multiple electrodes, wherein the actual implementation of the probe device 105 depends on the organ and condition under test. The probe device 105 may incorporate the electrodes attached to a needle, body cavity, ductoscopic, non-optical ductal or surface probe. A reference probe 110 may take the form of an intravenous probe, skin surface probe, nipple-cup or ductal epithelial surface reference probe depending on the test situation and region of breast under investigation.

To avoid stray capacitances, the electrodes may be connected via shielded wires to a selection switch 120 which may select a specific probe 105 following a command from the Digital Signal Processor (DSP) 130. The selection switch 120 also selects the appropriate filter interfaced to the probe 105, such that a low pass filter is used during DC measurements and/or an intermediate or high pass filter is used during the AC impedance measurements. The selection switch 120 passes the current to an amplifier array 140 which may be comprised of multiple amplifiers or switch the signals from different electrodes through the same amplifiers when multiple electrodes are employed. In a preferred embodiment digital or analogue lock-in amplifiers are used to detect minute signals buried in noise. This enables the measurement of the signal of interest as an amplitude modulation on a reference frequency. The switching element may average, sample, or select the signal of interest depending on the context of the measurement. This processing of the signal will be controlled by the DSP following commands from the CPU. The signals then pass to a multiplexer 150, and are serialized before conversion from an analogue to a digital signal by the ADC. A programmable gain amplifier 160 matches the input signal to the range of the ADC 170. The output of the ADC 170 passes to the DSP 130. The DSP 130 processes the information to calculate the DC potential and its pattern on the ductal-epithelial or skin surface as well as over the region of suspicion. In addition the impedance at varying depth and response of the DC potential and impedance to different ECM concentrations of ions, drug, hormones, or other agent are used to estimate the probability of cancer. The results are then sent to the CPU 180 to give a test result 185.

Alternatively the signal interpretation may partly or completely take place in the CPU 180. An arbitrary waveform generator 190 or sine wave frequency generator will be used to send a composite waveform signal to the probe electrodes and tissue under test. While a sine wave form is preferred, other wave forms can be used in the present invention including, for example, square waves. The measured signal response (in the case of the composite wave form stimulus) may be deconvolved using FFT (Fast Fourier Transforms) in the DSP 130 or CPU 180 from which the impedance profile is measured under the different test conditions. An internal calibration reference 195 is used for internal calibration of the system for impedance measurements. DC calibration may be performed externally, calibrating the probe being utilized against an external reference electrolyte solution.

Figure 2:
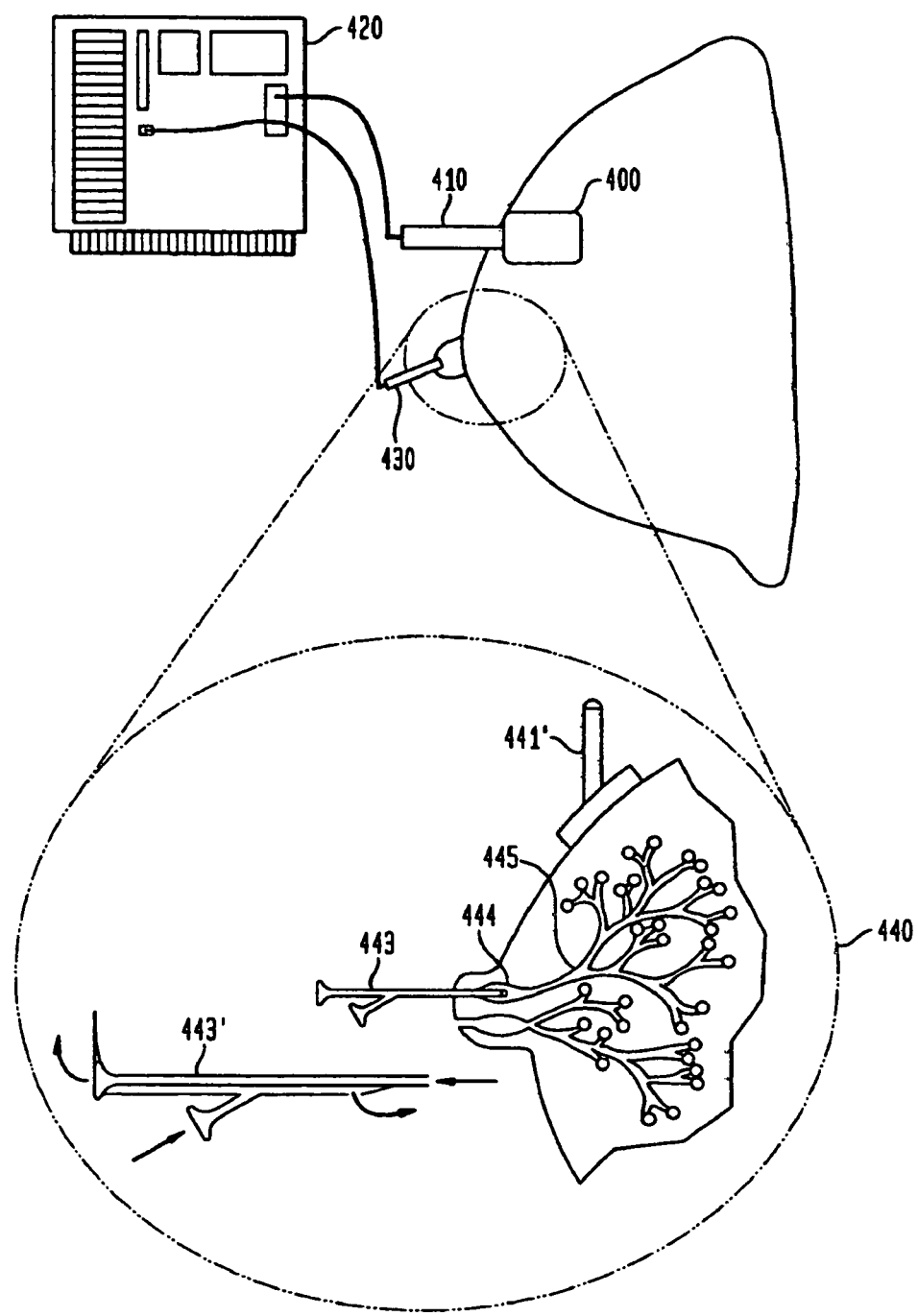
FIG. 2 illustrates an exemplary embodiment of a device suitable for use with systems and methods consistent with the present invention.

FIG. 2 includes a handheld probe 400, consistent with the present invention, which may be applied to the surface of the breast. The probe may include a handle 410. The probe 400 may be attached, either directly or indirectly using, for example, wireless technology, to a measurement device 420. The probe 400 may be referenced to an intravenous electrode, a skin surface electrode, other ground, nipple electrode, or ductal probe electrode within the duct or at the nipple orifice. In one embodiment, illustrated in FIG. 2, the reference is a nipple electrode or ductal probe 430, illustrated in greater detail at close-up 440. One advantage of this configuration is that DC electropotential and impedance can be measured between the nipple electrode 430 and the probe 400. The measurement is thus a combination of the DC potentials or/and impedance of the breast ductal epithelium, non-ductal breast-parenchyma, and the skin.

Referring to close-up 440, the ductal probe is inserted into one of several ductal orifices that open onto the surface of the nipple. Ductal probe 443 is shown within a ductal sinus 444, which drains a larger collecting duct 445.

Another advantage of using a nipple electrode is that a solution for irrigating the ductal system may be exchanged through the probe, permitting introduction of pharmacological and/or hormonal agents. As shown in magnified nipple probe 443, 443' fluid can be exchanged through a side port. Fluid may be infused into the duct and aspirated at the proximal end (away from the nipple) of the nipple probe. Different electrolyte solutions may be infused into the duct to measure altered permeability of the ductal epithelium to specific ions or the epithelium may be probed with different drugs to identify regions of abnormality. Estradiol, or other hormonal agents, may be infused into a breast duct to measure the abnormal electrical response associated with pre-malignant or malignant changes in the epithelium.

It should be understood that different configurations may also be used, such as a modified Sartorius cup that applies suction to the nipple. With this configuration, gentle suction is applied to a cup placed over the nipple. Small amounts of fluid within the large ducts and duct sinuses make contact with the electrolyte solution within the Sartorius cup, establishing electrical contact with the fluid filling the breast ducts. DC or AC measurements may then be made between the cup and a surface breast probe.

Figure 3:
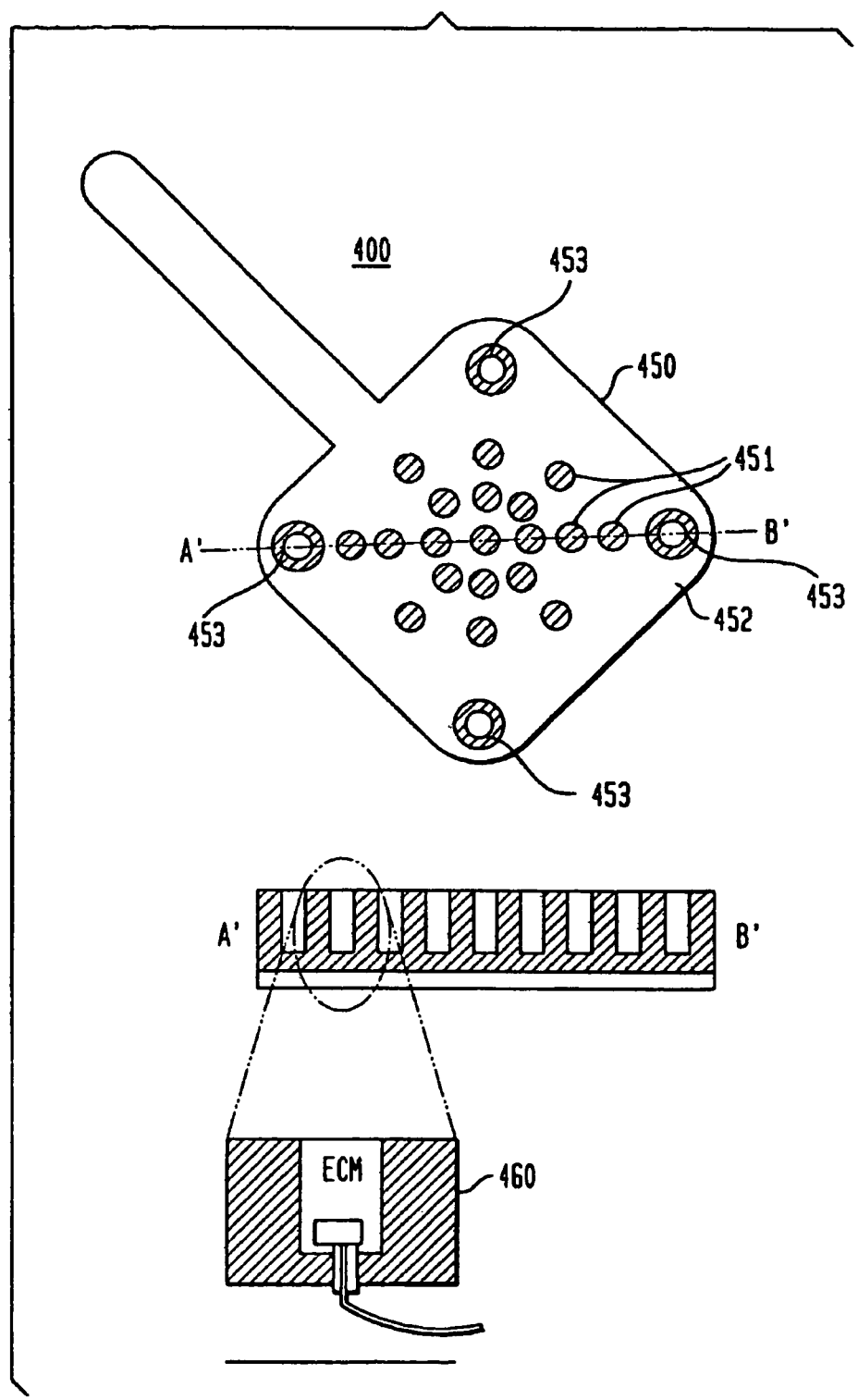
FIG. 3 illustrates an exemplary embodiment of a surface measurement probe suitable for use with systems and methods consistent with the present invention.

FIG. 3 illustrates the probe 400 of FIG. 2 in greater detail. The skin contact of the surface 450 is placed in contact with the breast. The surface electrodes 451 measure DC or AC voltages. The current passing electrodes 452 are used for impedance measurements. Probe 400 may also include one or more recessed wells containing one or more ECMs. Multiple sensor electrode arrays may be attached to the surface probe together with current passing electrodes. The individual electrodes may be recessed and ECMs with different composition may be used to pharmacologically, electrophysiologically, or hormonally probe the deeper tissues or epithelium under test. Spacing of the electrodes may be greater for the breast configuration than for other organ systems so that deeper tissue may be electrically probed and the impedance of the deeper tissue evaluated. This probe may either be placed passively in contact with the surface of the breast or held in place by pneumatic suction over the region of interest. Ports may be placed for the exchange of solutions or for fluid exchange and suction (not shown). Guard rings (not shown) may be incorporated to prevent cross-talk between electrodes and to force current from the contact surface into the breast. In this configuration there are four current passing electrodes [453] each positioned radially 90° apart. This permits current to be passed and the voltage response to be measured in perpendicular fields. The electrodes will be interfaced via electrical wire, or wireless technology, with the device described in FIG. 1 above.

Further embodiments of this technique may involve the use of spaced electrodes to probe different depths of the breast, and the use of hormones, drugs, and other agents to differentially alter the impedance and transepithelial potential from benign and malignant breast tissue, measured at the skin surface. This enables further improvements in diagnostic accuracy.

Figure 4:
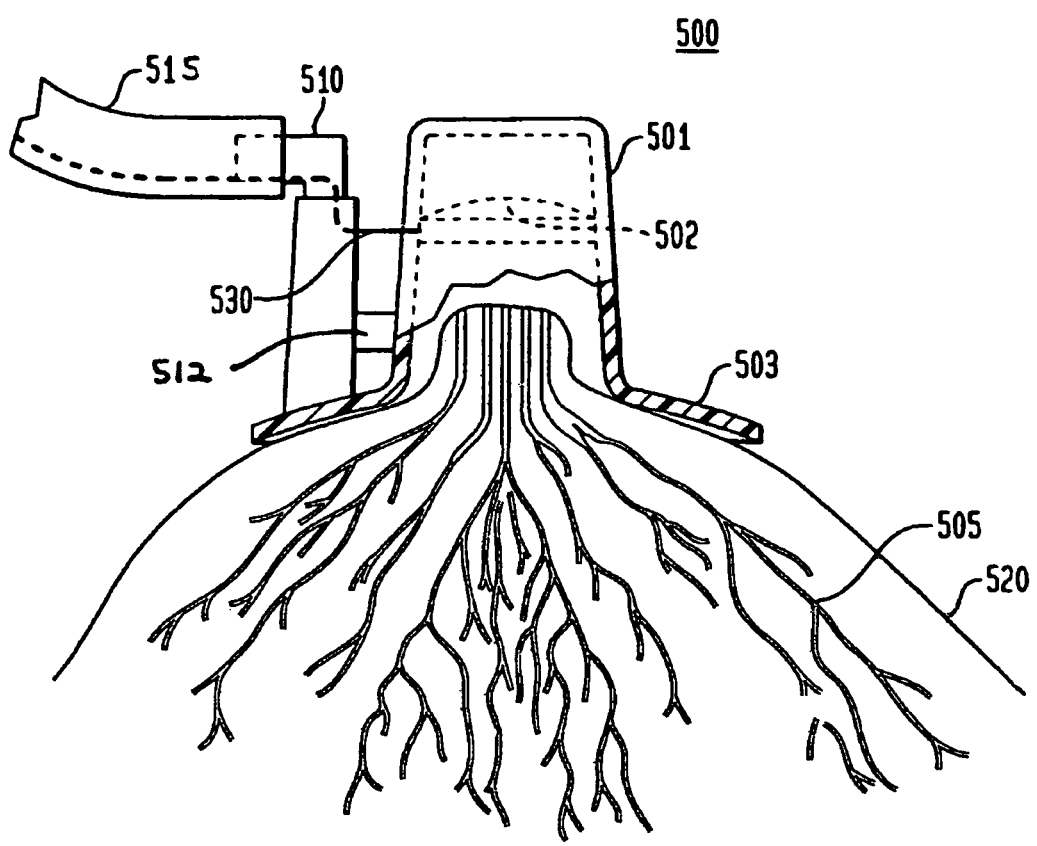
FIG. 4 illustrates an exemplary embodiment of a nipple electrode suitable for use with systems and methods consistent with the present invention.

FIG. 4 illustrates a nipple cup electrode [500] that may be used as a reference, current passing, voltage measuring or combination electrode [502]. In this configuration suction and fluid exchange is applied to the electrode housing [501] through a side port [510] connected by a flexible hose [515] to a suction device, aspirator or syringe (not shown). The flange [503] at the base of the cup is applied to the areola of the breast [520]. Pneumatic suction is applied through the side port and communicated to the housing by passage [512] so as to obtain a seal between the breast [520] and the nipple electrode [501]. Electrolyte solution is used to fill the cup and make electrical contact with the underlying ductal system. Fluid may be exchanged, or pharmacological and hormonal agents introduced, by applying alternating suction and injecting fluid or drugs into the cup through the side port. The pneumatic suction will open up the duct openings [505] either by itself or after preparation with alcohol or de-keratinizing agents to remove keratin plugs at the duct openings at the surface of the nipple. The nipple cup electrode [502] may be interfaced by means of an electrical connection [530] or by a wireless connection (not shown) with the devices illustrated in FIGS. 1-3 to obtain DC potential, AC impedance or combination measurements.

Figure 5:
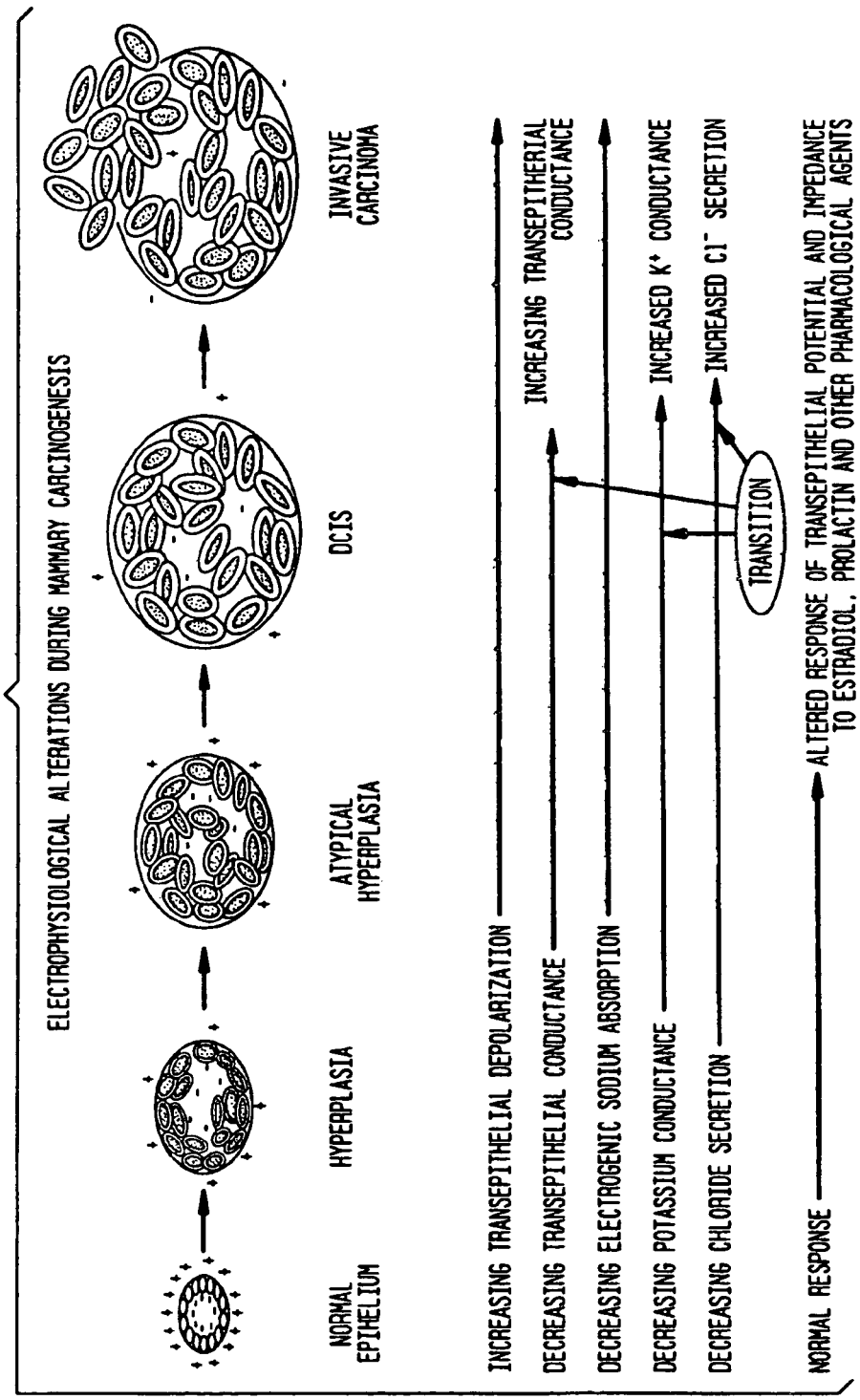
FIG. 5 illustrates electrophysiological changes that occur within the ductal epithelium during the development of breast cancer.

FIG. 5 illustrates the histological and electrophysiological changes that occur during the development of breast cancer. The continuum from normal ductal epithelium, through hyperplasia, atypical hyperplasia, ductal carcinoma in situ (DCIS), to invasive breast cancer is thought to take 10 to 15 years. Some of the steps may be skipped although usually a breast cancer develops within a background of disordered ductal proliferation. The normal duct maintains a transepithelial potential (inside of duct negatively charged), which depolarizes and impedance, which increases during the development of cancer. Once an invasive breast cancer develops the impedance decreases with loss of tight junction integrity, and conductance through the tumor is enhanced. The disordered ducts have altered electrophysiogical and ion transport properties. These properties are illustrated in the lower aspect of FIG. 5. These electrophysiological and transport alterations are exploited to diagnose breast cancer, proliferative and premalignant changes in the breast using, for example, transepithelial measurements of potential, or impedance, or a combination of transepithelial surface potential measurement, AC-impedance measurements and pharmacological manipulations. Using DEIS at higher frequencies, such as about 5K Hz to about 100K Hz, the sub-epithelial impedance of the breast parenchyma is measured to estimate mammographic density (a property of the non-epithelial breast parenchyma), and breast cancer risk.

FIG. 6 illustrates the determination of subepithelial impedance, Zsub, based on a ductal epithelial impedance spectra, in other words, a Nyquist plot at high frequency, obtained from a 37 year old woman with no risk factors for breast cancer. As defined above, Zsub is the impedance value corresponding to the point on the Nyquist plot where the curve approaches or meets, intersects, the x-axis at the highest frequency tested. For example, in FIG. 6 Zsub is 97 ohms at a frequency of 60 KHz. Also as discussed above, at this frequency it is believed that the dielectric properties of cell membranes and surface skin overlying the breast break down so that Zsub is dominated by the impedance of the breast parenchyma. The curve obtained in FIG. 6 was obtained from measurements at several frequencies, but the present invention does not require a testing at a substantial number of frequencies (for example, greater than about 5 frequencies) in order to obtain a useful value for Zsub. Preferably, and for practical reasons, it is suitable to obtain make impedance measurements at about two sufficiently high frequencies in order to obtain a value for Zsub.

The methods of the present invention have been applied as follows: With IRB and patient consent, electrical contact with ductal epithelium was established non-invasively, using the nipple cup sensor as shown schematically in FIG. 7 in 232 women scheduled for breast biopsy. Testing was conducted as follows:
1. The nipple cup/sensor is placed over the nipple and the nipple cup is filled with physiological saline;
2. The saline is aspirated to a negative pressure of approximately 100 mm Hg (5 ml of saline withdrawn);
3. 3 ml of saline is added back (i.e. negative pressure reduced to approximately 20 mm Hg);
4. Steps 2 and 3 are repeated two to three times to remove air bubbles, and to raise the nipple slightly;
5. The nipple cup sensor is connected to the leads of the frequency response analyzer;
6. Skin electrodes (hydrogel) are placed on the skin in each quadrant of the breast approximately 4 cm (inner) and 7 cm (outer) from the nipple;
7. Additional current passing electrodes are placed outside the outermost current passing electrodes (the electrode at 7 cm from the nipple); these electrodes are on the edge of the breast at approximately 8-10 cm from the nipple depending on the size of the breast.

Typically two sets of measurements were made between the nipple sensor and skin surface electrodes placed in each of 4 quadrants of the breast. Zsub was measured at 60 KHz using a frequency response analyzer, and sine-wave correlation technique. Zsub was averaged for each of the four breast quadrants. Data were analyzed using a t-test, Mann-Whitney test, ANOVA, Pearson Moment Correlation, and logistic regression as appropriate.

Based on the data obtained in the above tests, the following factors have been found to correlate with Zsub:
Positive Correlation
1. Age
2. Weight or body mass index (BMI)
3. Distance electrodes are placed away from the nipple
4. Presence of proliferative lesion or cancer on subsequent biopsy, which may be related to age, BMI or other factor influencing risk
5. Strong family history or genetic risk of breast cancer
Negative Correlation
1. Day of menstrual cycle (value 0 for post-menopausal woman
2. Mammographic breast density Initial test results and analysis were based on a smaller sample size. This was followed by a further analysis based on additional subjects resulting in an increased sample size. Both are reported below. While they are consistent with one another, the later, larger population has produced more reliable and useful algorithms It was initially found that Zsub correlated with the age of the patient in benign (BN, n=114), (0.61 Correlation Coefficient (CC), p<0.0001), and in proliferative disease (PROL, n=118), which includes both malignant disease and benign proliferative disease (0.46 CC, p=0.0001). Similarly, Zsub significantly correlated with both patient weight and the distance that the electrodes were placed from the nipple, and inversely correlated with position in menstrual cycle for BN but not PROL patients (See FIGS. 8, 9, 11 and 12). Zsub was 170±7 ohms in BN patients (n=97), 229±10 ohms in benign proliferative patients (PROL-BN) (n=32) and 258±10 ohms in PROL-cancer (CA) patients (n=61), (p<0.001). Body mass index (BMI) and breast size increased with age and significantly correlated with Zsub in both BN, and in PROL patients (data not shown). Even with limited initial data it was found that mammographic breast density was inversely related to Zsub (−0.622 CC, (Correlation Coefficient) p<0.000001). Zsub is correlated with (can be predicted by) a combination of age, BMI and mammographic breast density (MD). Similarly MD can be predicted by a linear combination of age, BMI and Zsub and is inversely correlated with these factors as described herein.

Figure 8:
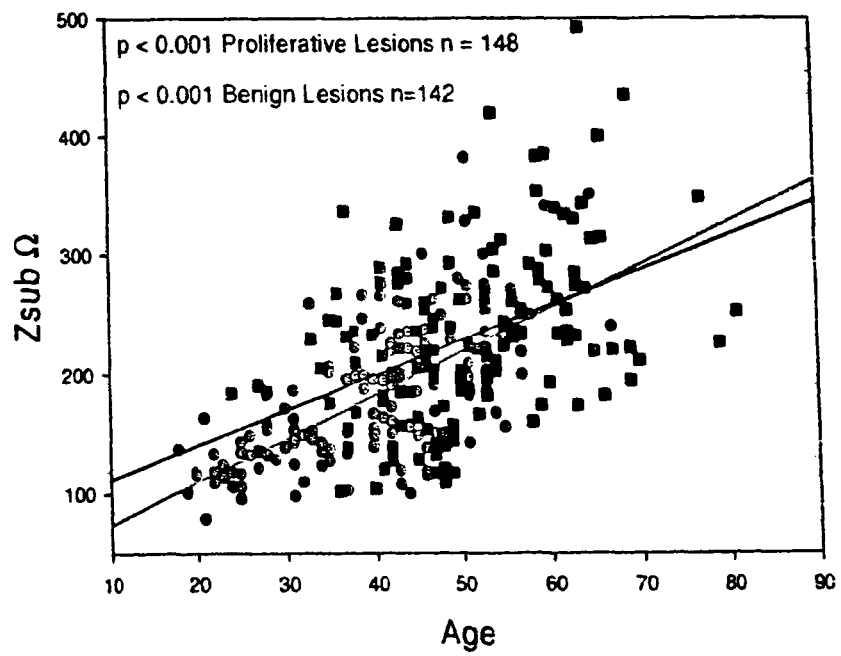
FIG. 8 illustrates the correlation of subepithelial impedance with age.
Figure 9:
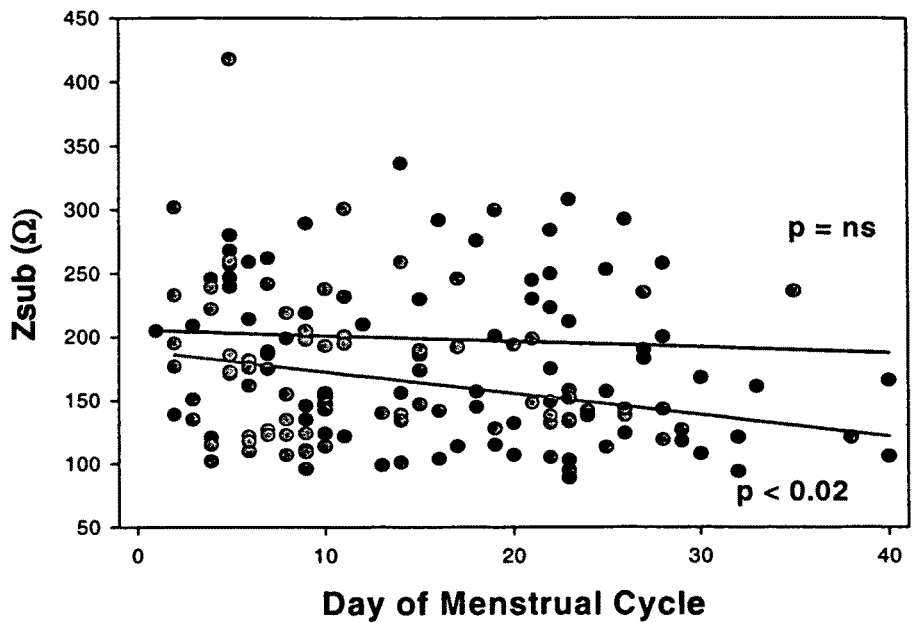
FIG. 9 illustrates the effect of menstrual cycle on subepithelial impedance.
Figure 10:
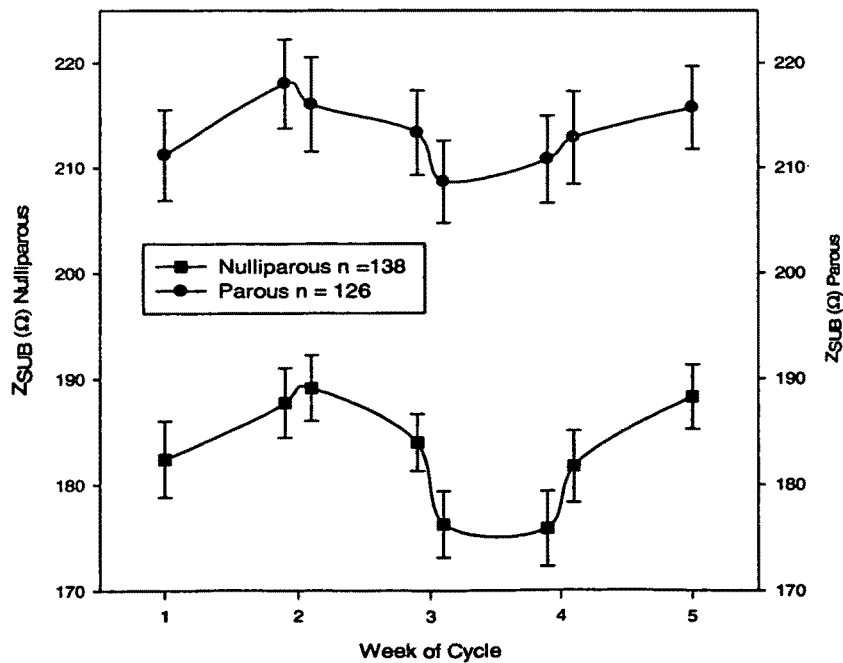
FIG. 10 illustrates changes in sub-epithelial impedance during menstrual cycle by parity.

Referring to the data figures individually:

FIG. 8: Correlation of age with Zsub in benign (n=114 initially, currently=142) and proliferative breasts (n=118 initially, currently=148). The circles denote patients whose subsequent biopsy showed benign changes whereas the squares denote proliferative changes or cancer. Zsub was lower in benign versus proliferative breasts;

FIG. 9: Correlation of day of menstrual cycle with Zsub in benign (n=78) and proliferative breasts (n=60). Zsub correlates with position in menstrual cycle for benign, but not for proliferative breasts;

FIG. 10: Illustration of changes in sub-epithelial impedance during menstrual cycle by parity, i.e., parous and nulliparous women. As can be seen, Zsub is higher in parous women and Zsub decreases significantly in nulliparous women between follicular and luteal phase (weeks 3 and 4) and significantly more than in parous women between the same phases. As discussed herein, it has been found that mammographic density decreases with age. The decrease in mammographic density is referred to as "involution". Involution occurs throughout a woman's life. Women in their early twenties frequently have mammographic densities of greater than 70%, and corresponding Zsub values of about 100 ohms to about 130 ohms. Two events result in significant involution: (1) first full term pregnancy; and (2) menopause.

Figure 11:
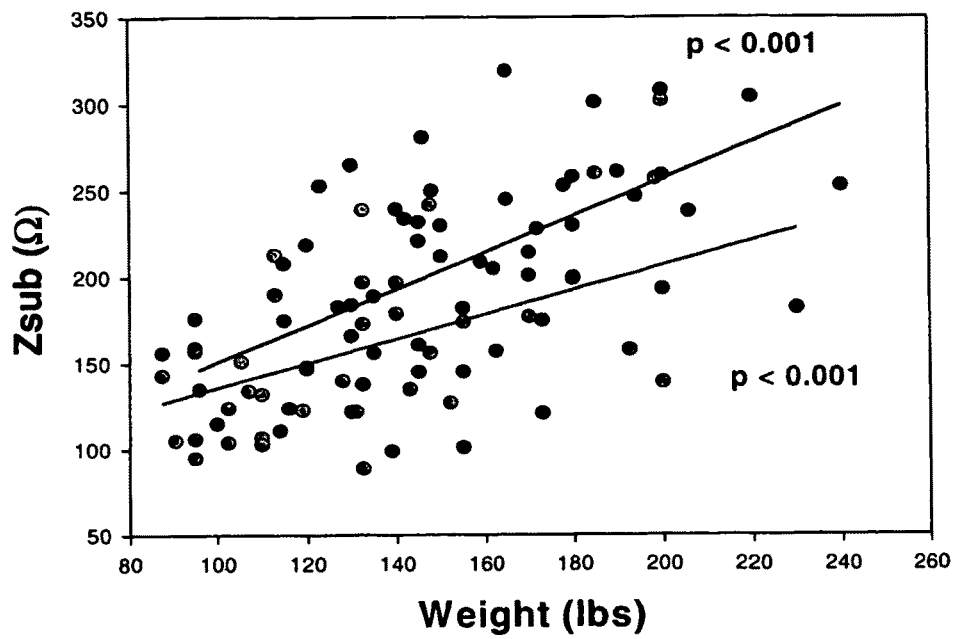
FIG. 11 illustrates the correlation of subepithelial impedance with weight.
Figure 12:
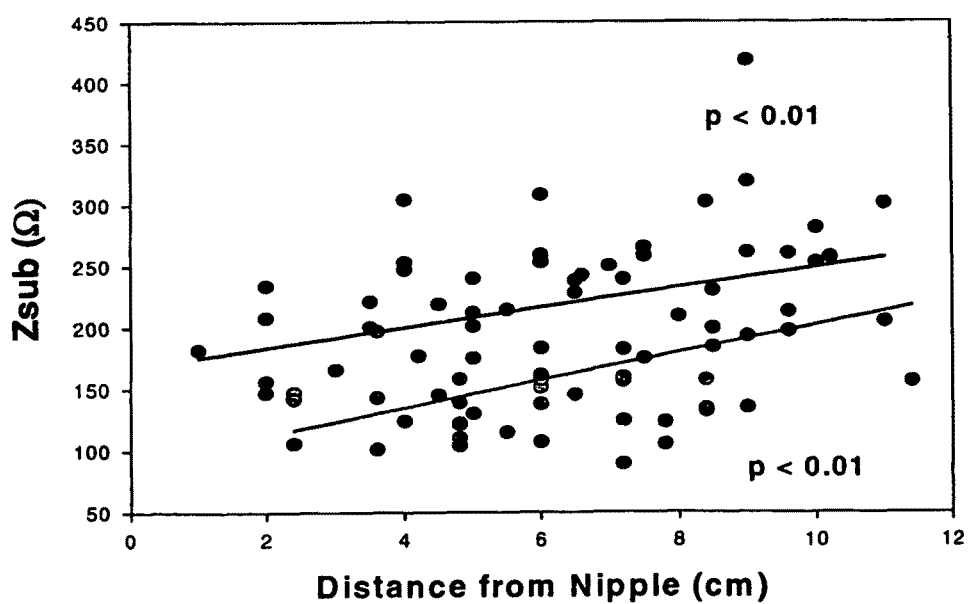
FIG. 12 illustrates the correlation of subepithelial impedance with placement distance of electrodes from the nipple.

Subsequent pregnancies will often result in further involution although usually not as great as the first full term pregnancy. Failure of involution to occur with increasing age, obesity, menopause or full term pregnancy is an indicator of an increased risk for breast cancer. This can be measured in women at any stage of life using ductal epithelial impedance spectroscopy (DEIS), a method developed by the inventor herein, and specifically using the methods of the present invention, because of the non-invasive nature of the method(s) compared with, for example, X-ray mammography, which is generally only used with women over 40 years of age because of the radiation risk. Using the methods of the present invention, women in their twenties can undergo baseline Zsub testing followed by annual or biannual testing to monitor age- and BMI-related mammographic density changes. Failure to involute with age, increased BMI, change in breast size and particularly with full term pregnancy, and menopause may identify women at increased risk for breast cancer in whom subsequent further evaluation may be indicated e.g. breast examination using X-ray mammography, breast MRI, nuclear imaging, tomosynthesis, biopsy, genetic testing, etc.;

FIGS. 11 and 12: Correlation of patient's weight and electrode distance from the nipple with Zsub in benign (light circles) or proliferative lesions (dark circles).

Figure 15:
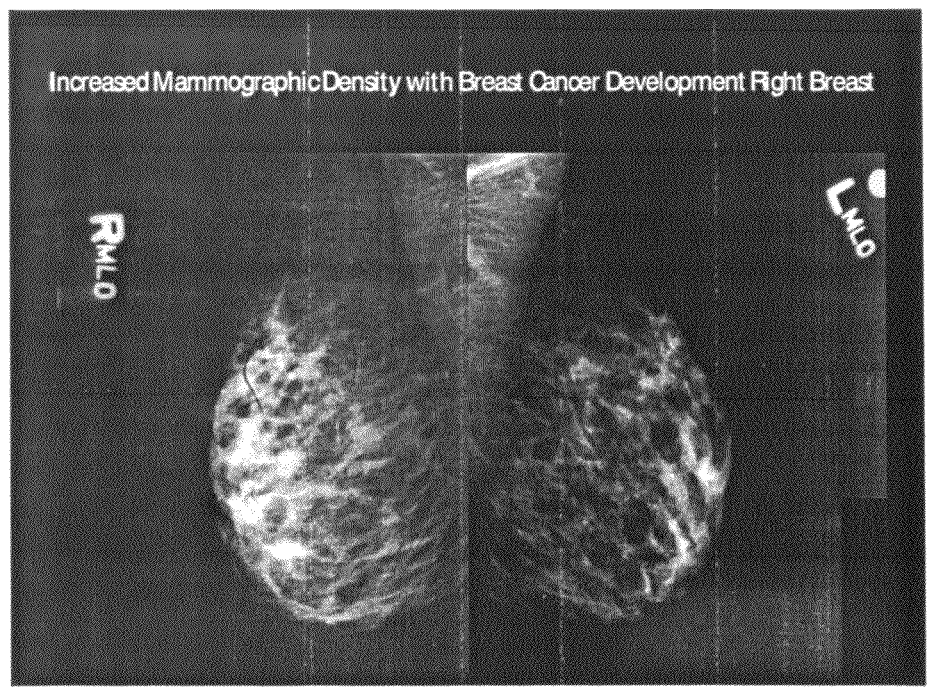
FIG. 15 is an X-ray mammogram showing differences in breast density between the two breasts of a patient.

FIG. 15: This is an X-ray mammogram showing differences in breast density between the two breasts of a patient. Since measurement of Zsub can be made independently in each of the breasts, it is possible to identify asymmetric breast density and the concomitant risk that such asymmetry is an indicator of breast cancer. It has been observed that the density difference between the breasts of an individual is typically within about 5 to about 10%. Zsub measurements between breasts are also usually highly correlated, typically within about 5 to about 10%. Zsub measurements can be made according to the methods herein to estimate asymmetry developing between breasts with the lower Zsub indicating a higher density and an increased risk for breast cancer. Therefore Zsub measurements between breasts may be used to monitor for increased risk for breast cancer.

The X-ray mammograms shown in FIG. 15 illustrate increased density in the right breast of a 39 year-old woman. Mammographic density was visually estimated from the X-ray films as 70% (percent density) in the right breast compared with 50% in the left breast. Electrodes were placed 5 cm from the nipple on the skin surface. Average Zsub (average for 4 breast quadrants) was 110 ohms in the right breast compared with an average Zsub of 151 ohms in the left breast, indicating significant density and Zsub asymmetry between breasts. Although the X-ray mammograms do not show a mass, (note that a radio-opaque marker, or white dot, was placed over an area in the right breast where the patient described a "thickening"), a subsequent breast MRI with contrast identified multifocal breast cancer developing in the right breast which was confirmed on subsequent biopsies. Therefore both the X-ray mammograms and Zsub measurements identified an asymmetric density condition developing in the right breast.

Risk that a female patient will be found to have proliferative or pre-cancerous changes in the breast can be estimated based on the methods of the present invention. Specifically, the Zsub of one or both breasts of the patient is measured, Zsub (measured) or Zsubm. In addition, a value for Zsub can be estimated, Zsub (estimated) or Zsube, using an algorithm obtained from forward stepwise regression of the data:

$$Zsube=107.753+(1.083*Age)+(-1.074*Breast\ Density)+(3.196*Body\ Mass\ Index);$$

where Age is measured in years; Breast Density is expressed in % and is estimated from the appearance of the breast(s) on a mammogram; and Body Mass Index, BMI, is defined as:

Wt (lbs)*703)/Height$^2$(inches$^2$), or

Wt (lbs)*4.88/Height$^2$(ft$^2$).

From the values of Zsubm and Zsube, the ratio $Zsub_m/Zsub_e$ (referred to as the "Risk Ratio") is calculated; Risk Ratio means the risk that a patient not exhibiting overt symptoms of proliferative breast disease or cancer will be found to have such condition on subsequent direct testing, such as biopsy. Based on analysis of the data, including information obtained from follow-up biopsies, it has been concluded that the Risk Ratio can be used as an indicator as follows.

It would be expected that the ratio of Zsubm/Zsube would be about 1.0 if Zsube is accurately predicted from known factors that influence it, for example increased age, higher BMI and/or and interaction of the two. When the Risk Ratio is about 1.2 the measured Zsub (Zsubm) is about 20% higher than estimated based on age and BMI (and additionally, distance electrodes are placed from the nipple, DFN, where this variable in included in the algorithm, as explained elsewhere herein), etc. In patients who are considered to be at higher risk because they are older and have a higher BMI, the higher risk is expected primarily to be due to these factors rather than having a higher Zsub than one would predict due to the effect on risk of tissue impedance. Statistically this is referred to as an interaction or confounding effect. In other words age affects Zsub, breast density also affects Zsub, age also affects breast density. It is then necessary to sort out the contribution of density to Zsub which is not simply just an age effect. Furthermore, both age and BMI are independent variables that influence the observed or measured Zsub in an individual; if not, they would not be retained in the logistic regression modeling. Thus, older patients with higher than normal (or typical) BMI, and exhibiting Zsubm/Zsube or Risk Ratio greater than about 1.2 (for example, greater than about 1.1, 1.15, 1.2, 1.25, 1.3, 1.35, etc.) are at increased risk of proliferative disease or breast cancer.

On the other hand, it has been observed that high mammographic density correlates with low Zsub. Thus, a ratio of Zsubm/Zsube lower than about 0.8 for example, lower than about 0.9, 0.85, 0.8, 0.75, 0.7, 0.65, etc.) can indicate a higher risk of finding a proliferative lesion or cancer on subsequent biopsy because of increased mammographic density, a known risk factor for breast cancer, particularly when adjusted for the known influence of age and BMI. Such a low value of Zsubm/Zsube can be of particular concern in a younger, physically fit person, i.e., a person with a normal, typical or even low BMI.

Overall, where a person exhibits a Risk Ratio of greater or lesser than about 1.0±0.2 it would suggest that closer examination is warranted using more invasive, risky and/or more expensive test methods, including, for example, biopsy, MRI, X-ray (for a younger patient), etc.

Since the initial results, additional data was obtained and added to the initial data resulting in a larger data set. Analysis of all of the data, including the models and algorithms derived therefrom, is reported below. For convenience, mammographic density, MD, is sometimes referred to as "density".

1. An expected value for Zsub, Zsube, for the total sample population (including both pre-menopausal and post-menopausal women) can be predicted from the following model (the symbol * indicates multiplication):

$$Zsube=107.753+(1.083*Age(years))+(-1.074*Breast\ Density(\%\ Density\ from\ Mammogram)+(3.196*BMI(body\ mass\ index))$$

Body Mass Index is defined as (Wt (lbs)*703)/Height$^2$ (inches$^2$)), or (Wt (lbs)*4.88/Height$^2$(ft$^2$)).

Variables in Model:

| Group | Coefficient | Standard Coefficient | Standard Error | F-to-Remove | P |
|---|---|---|---|---|---|
| Constant | 107.753 | — | 41.366 | — | — |
| Age | 1.083 | 0.182 | 0.475 | 5.210 | 0.025 |
| Density | −1.074 | −0.470 | 0.203 | 27.939 | <0.001 |
| BMI | 3.196 | 0.245 | 1.000 | 10.205 | 0.002 |

Note that MD is the strongest factor predicting the value of Zsub (p < 0.001)

2. Alternatively Mammographic Density (for the total population), a known risk factor for breast cancer, can be predicted from the following model:

Percent Mammographic Density(MD)=141.788+(−0.716*age)+(−1.113*BMI)+(−0.199*Zsub (ohms))

Note that negative coefficients indicate that mammographic density inversely correlates with age, BMI and Zsub as may be expected since breast density decreases with increasing age and BMI, and hence Zsub increases (increased impedance). Both age and Zsub are the strongest predictors of mammographic density (p<0.001) as would be expected since age and Zsub (strongly relate to density and are both significant risk factors for breast cancer Variables in Model:

| Group | Coefficient | Standard Coefficient | Standard Error | F-to-Remove | P |
|---|---|---|---|---|---|
| Constant | 141.788 | — | 11.931 | — | — |
| Age | −0.716 | −0.274 | 0.197 | 13.208 | <0.001 |
| BMI | −1.113 | −0.195 | 0.438 | 6.469 | 0.012 |
| Zsub | −0.199 | −0.454 | 0.0376 | 27.939 | <0.001 |

3. When logistic regression is applied to a pre-menopausal population of women, mammographic density (MD) can be predicted from the following model:

MD=127.770+(−1.339*BMI)+(−0.259*Zsub)

Note that age is no longer included in the model for the population of pre-menopausal women, implying that obesity (BMI) may be more important than age in predicting MD in pre-menopausal women. BMI has been forced into the model as p value approaches significance (p=0.051). Note in the later modeling when an adjustment is made for the distance that the electrodes are placed from the nipple (thus taking into consideration the volume of breast tissue being electrically "interrogated") BMI becomes significant for pre-menopausal women. Whatever variability may have been present due to electrode placement may have been overwhelmed by the BMI of this particular population of individuals.

Variables in Model

| Group | Coefficient | Standard Coefficient | Standard Error | F-to-Remove | P |
|---|---|---|---|---|---|
| Constant | 127.770 | — | 13.308 | — | — |
| Pre BMI | −1.339 | −0.239 | 0.673 | 3.957 | 0.051 |
| Pre Z'sub | −0.259 | −0.477 | 0.0652 | 15.759 | <0.001 |

4. When logistic regression is applied to a post-menopausal population of women, mammographic density can be predicted from the following model:

MD=127.178+(−0.874*Age)+(−0.219*Zsub)

Note that BMI is excluded from the post-menopausal model, possibly because menopausal involution results in significant replacement of dense breast tissue by high impedance fat, regardless of BMI status.

Variables in Model

| Group | Coefficient | Standard Coefficient | Standard Error | F-to-Remove | P |
|---|---|---|---|---|---|
| Constant | 127.178 | — | 20.991 | — | — |
| Age | −0.874 | −0.274 | 0.343 | 6.494 | 0.014 |
| Z'sub | −0.219 | −0.607 | 0.0389 | 31.765 | <0.001 |

5. In the regression analysis of the initial data population, distance that the electrodes are placed from the nipple is retained in the model as a predictor of Zsub. In the current larger study of 200 patients there is a less obvious association, probably because the positioning of the electrodes has been standardized. However, in individual patients the further electrodes are placed from the nipple the greater the value for Zsub, since a larger volume of tissue is subject to electrical analysis. In the modeling of mammographic density a more parsimonious model is to adjust the Zsub measurement for the distance each electrode is placed away from the nipple. This in turn changes the predictive models as shown below:

ZsubDFN (Zsub adjusted for distance electrodes placed from nipple in cm) is defined by the formula:

Zsub$_{DFN}$=169.512+(6.668*DFN(cm)) derived from the linear regression of Zsub versus DFN The adjusted Zsub (ADJZsub) is then derived from the formula:

ADJZsub=Zsub$_M$/Zsub$_{DFN}$ (where subscript M=measured, i.e., measured Zsub).

6. When logistic regression is applied to a pre-menopausal population of women, mammographic density (MD) can be predicted from the following model:

MD=131.936+(−1.444*BMI)+(−54.752*ADJZsub (in arbitrary units derived as in 5 above)

Variables in Model

| Group | Coefficient | Standard Coefficient | Standard Error | F-to-Remove | P |
|---|---|---|---|---|---|
| Constant | 131.936 | — | 13.325 | — | — |
| BMI | −1.444 | −0.258 | 0.645 | 5.016 | 0.028 |
| ADJZsub | −54.752 | −0.474 | 13.307 | 16.929 | <0.001 |

7. When logistic regression is applied to a post-menopausal population of women, mammographic density can be predicted from the following model:

MD=120.178+(−0.869*Age)+(−39.179*ADJZsub (in arbitrary units derived as in 5 above))

Variables in Model

| Group | Coefficient | Standard Coefficient | Standard Error | F-to-Remove | P |
|---|---|---|---|---|---|
| Constant | 120.079 | — | 22.273 | — | — |
| Age | −0.869 | −0.273 | 0.368 | 5.584 | 0.023 |
| ADJZsub | −39.179 | −0.542 | 8.351 | 22.012 | <0.001 |

Note that both 6 and 7 for pre- and post-menopausal women incorporate the DFN as a variable influencing Zsub and are preferred, more universal models, even if efforts are made to place electrodes a standard distance from the nipple when conducting measurements.

8. As may be expected given the relationship between Zsub and Density, Zsub is significantly higher in post-menopausal patients (Post Z'sub) with mean values of 241.938±8.403 (mean±SEM) ohms compared with 183.343±5.769 ohms (p<0.001) in pre-menopausal patients (Pre Z'sub).
t-Test
Normality Test: Passed (P=0.097)
Equal Variance Test: Passed (P=0.523)

| Group Name | N | Mean | Standard Deviation | SEM** |
|---|---|---|---|---|
| Post-menopausal Z'sub | 48 | 241.938 | 58.219 | 8.403 |
| Pre-menopausal Z'sub | 70 | 183.343 | 48.271 | 5.769 |

**Standard Error of the Mean

Difference of means: 58.595
t=5.952 with 116 degrees of freedom. (P=<0.001)
95 percent confidence interval for difference of means: 39.097 to 78.092

Thus the difference in the mean values of the two groups is greater than would be expected by chance; there is a statistically significant difference between the input groups (P=<0.001).
Power of performed test with alpha=0.050:1.000

Similarly mammographic density (percent density) is significantly lower in post-menopausal patients 17.5 (7.5-32.5) % (median (25-75% confidence limits) ("Post Density") compared with pre-menopausal patients 47.5 (25.0-60.0) % ("Pre Density") (p<0.001)
Mann-Whitney Rank Sum Test

| Group | N | Median | 25% | 75% |
|---|---|---|---|---|
| Post-menopausal Density | 48 | 17.500 | 7.500 | 32.500 |
| Pre-menopausal Density | 70 | 47.500 | 25.000 | 60.000 |

Mann-Whitney U Statistic=798.000
T=1974.000 n(small)=48 n(big)=70 (P=<0.001)

The difference in the median values between the two groups is greater than would be expected by chance; there is a statistically significant difference (P=<0.001)

9. FIG. 10 illustrates the correlation of Zsub with position in menstrual cycle. The circles denote parous (n=16), and the squares nulliparous (n=17) controls. Nulliparous controls have a lower Zsub suggesting a more conductive parenchyma particularly during luteal phase. Not only is Zsub higher in parous women, but the change in Zsub between follicular and luteal phase is approximately 50% greater in nulliparous women. The decrease in Zsub between follicular and luteal phase suggest a decrease in impedance possibly due to a higher fluid content of the breast, or a physical change in breast tissue affecting Zsub, in nulliparous women. The ratio of the impedance measured at 60 KHz to the impedance measured at 10 KHz or 6 KHz may give more discriminatory information with regard to risk. If the change in impedance is measured when the frequency of the electrical signal is decreased from 60 KHz to 10 KHz a significant increase in impedance is identified in both parous and nulliparous women. The impedance change is still greater when the frequency is changed from 60 KHz to 6 KHz. If the change in impedance is multiplied for the 60 to 10 KHz change by the change from 60 KHz to 6 KHz an interaction term is obtained which shows a significant difference in the change, i.e., parous women (P-interaction) have a median result of 766 versus 844 (p=0.011) compared to nulliparous women (N-interaction) respectively. These data were analyzed as follows:
t-test: Normality Test Failed (P<0.050). No further analysis according to the t-test.
Mann-Whitney Rank Sum Test:

| Group | N | Median | 25% | 75% |
|---|---|---|---|---|
| P-interaction | 487 | 766.135 | 456.959 | 1149.406 |
| N-interaction | 595 | 843.600 | 491.173 | 1256.176 |

Mann-Whitney U Statistic=131909.000
T=250737.000 n(small)=487 n(big)=595 (P=0.011)

The difference in the median values between the two groups is greater than would be expected by chance; there is a statistically significant difference (P=0.011).

It should be noted that at frequencies above approximately 5000 Hz (5 KHz) there is very little change in the reactance because the dielectric properties of the skin and epithelium have little influence on the overall impedance and the electrical signal interrogates subepithelial tissue of the breast; the impedance is effectively a simple resistance above 5 KHz using the intraductal measurement approach disclosed herein. Thus, in addition to a Zsub measurement at about 50 KHz or about 60 KHz, additional Zsub measurements at one or more frequencies between about 5 KHz and 20 KHz, including calculation of the magnitude of the change in values between the higher and lower frequencies and ratios thereof can provide additional information relating to the fluid status of the breast or other characteristics of the breast tissue.

Additionally, the above studies were performed in a control group of women under the age of 40 without known risk factors for breast cancer, except parity status. Women at increased risk because of family history, breast density etc., may be expected to have a greater difference in these intermediate frequency measurements between "at risk" and "normal-risk". Hence parous versus nulliparous women, examined at different points in menstrual cycle, serves as a model for slightly higher risk, i.e., nulliparous women have a higher risk of breast cancer than parous women.

10. In the initial analysis discussed above, position in menstrual cycle is a factor in the algorithm predicting the estimated value of Zsub. As can be seen in FIG. 10 above, Zsub tends to be lower in the luteal phase of cycle compared with weeks 1 and 2 (follicular phase), although the relationship is no longer clearly linear and it may be necessary to normalize the data by combining data in the first and second weeks and the data in the third and fourth weeks. Thus, position in menstrual cycle continues to represent a useful variable for estimating breast density because of the observed relationship between Zsub and position in cycle. Changes in breast density have been observed during menstrual cycle in mammographic studies, so that this is generally known in the radiology literature. Breast density is observed to be higher in luteal phase, consistent with the observations herein that Zsub is lower.

Overall, there is significant interaction between the variables of body mass index (BMI), age, mammographic breast density (MD) and Zsub so that Zsub appears also to be correlated with risk of developing breast cancer. Furthermore, since age and BMI are both related to Zsub and MD the stronger correlation is between Zsub to density, and the higher apparent risk of developing breast cancer due to increased age also correlates with higher Zsub and higher BMI also correlates with increased age. In the logistic regression models, age and BMI are controlled for so that when Zsub is retained as a variable in the model it implies that Zsub is related to MD, independent of the effects of age and BMI.

Figure 14:
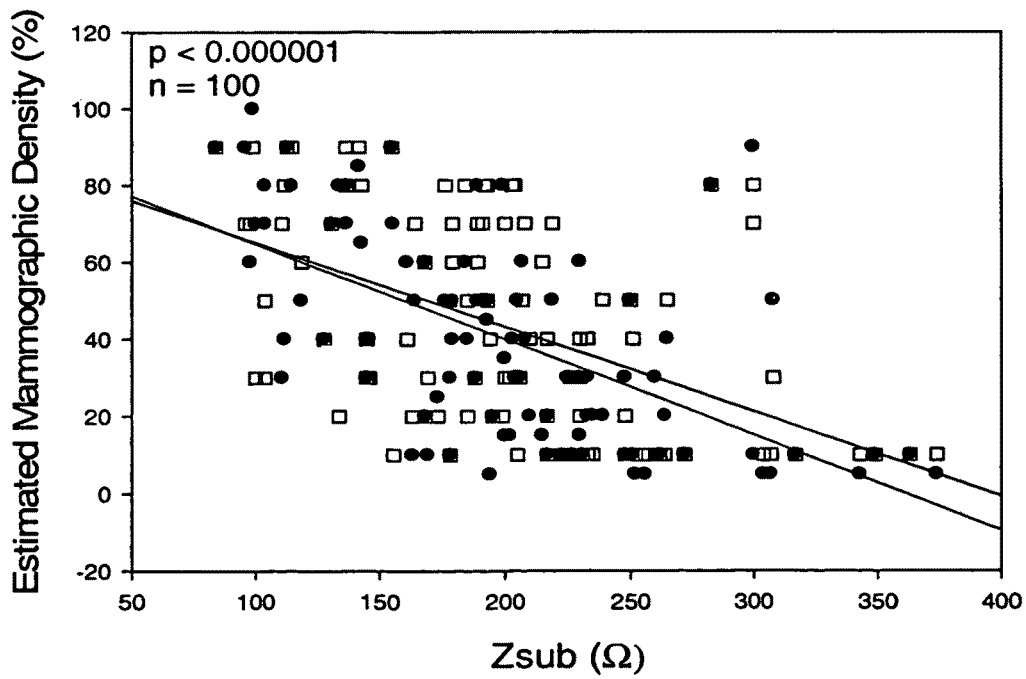
FIG. 14 illustrates the correlation of estimate of mammographic density with subepithelial impedance (Zsub)

Using the methods described above for estimating mammographic density, and specifically the ACR BI-RADS method, estimated mammographic density has been correlated with sub-epithelial impedance, Zsub; these results are illustrated in FIG. 14. Estimation of mammographic density was made by two blinded observers, whose estimates were highly correlated with each other and to Zsub (see FIG. 13). Much of the variability in FIG. 14 is accounted for by Age and BMI, as indicated in the algorithms above.

In a further embodiment of the invention, in addition to the use of a single frequency for measuring Zsub, for example about 50 KHz or about 60 KHz, a second impedance measurement can be made at a significantly lower frequency, $Z_0$. For this value impedance would be measured at a frequency approaching or at a value of 0 or DC (direct current). However, at very low frequencies skin impedance can dominate the measured value so that it would be necessary to avoid such interference by using sonopheresis at the skin site, as described above, or to use spiked or microneedle electrodes or the like. Alternatively, a compromise frequency can be used, such as about 1000 Hz to about 5000 Hz at which frequency the impedance of the skin has less influence. The measured value of $Z_0$ would function as an estimate of extracellular fluid i.e. all the current passes through the extracellular (interstitial fluid) compartment and this condition likely changes in women at high risk. Therefore the ratio of $Zsub/Z_0$ or each value individually may provide additional characterizing criteria which can be used for various purposes, including assessing the risk of breast cancer.

Devices to measure the electrophysiological characteristics of tissue and the differences between normal and abnormal tissue may include those known in the art such as electrical meters, digital signal processors, volt meters, oscillators, signal processors, potentiometers, or any other device used to measure voltage, conductance, resistance or impedance.

DC potential is usually measured using a voltmeter, consisting of a galvanometer in series with a high resistance, and two electrodes (one working and one reference). Voltmeters may be analog or digital. Ideally these should have an extremely high input resistance to avoid current-draw. DC potential may also be measured with an oscilloscope.

Impedance may be measured using a number of approaches. Without limitation, examples include phase-lock amplifiers, which may be either digital or analog lock-in amplifiers. Pre-amplifiers may be used in conjunction with the lock-in amplifier to minimize stray currents to ground improving accuracy. Digital lock-in amplifiers are based on the multiplication of two sine waves, one being the signal carrying the amplitude-modulated information of interest, and the other being a reference signal with a specific frequency and phase. A signal generator can be used to produce the sine waves or composite signal to stimulate the tissue. Analog lock-in amplifiers contain a synchronous rectifier that includes a phase-sensitive detector (PSD) and a low-pass filter. Other approaches include the use of an impedance bridge with an oscillator to produce an AC sine wave. These devices when automated are referred to as LCR-meters and use an auto-balancing bridge technique. Constant current or constant voltage current sources may be used. In one preferred embodiment, a constant current source is used. Rather than an oscillator with a fixed frequency signal a signal generator, which produces, superimposed sine waves may be used.

The tissue response is deconvolved using fast Fourier transforms or other techniques. Bipolar, tripolar or tetrapolar current and voltage electrodes may be used to make measurements. In one preferred embodiment tetrapolar electrode configurations are employed to avoid inaccuracies that are introduced due to electrode polarization and electrode-tissue impedance errors. Rather than impedance, current density may be measured using an array of electrodes at the epithelial or skin surface. Impedance may also be measured using electromagnetic induction without the need for electrode contact with the skin or epithelium.

In order to process large amounts of data, the methods of the present invention, including in combination with measuring Zsub, can be implemented by software; on computer readable medium and executed by computerized equipment or central processor units.

Example of Measurement System and Method

Figure 7:
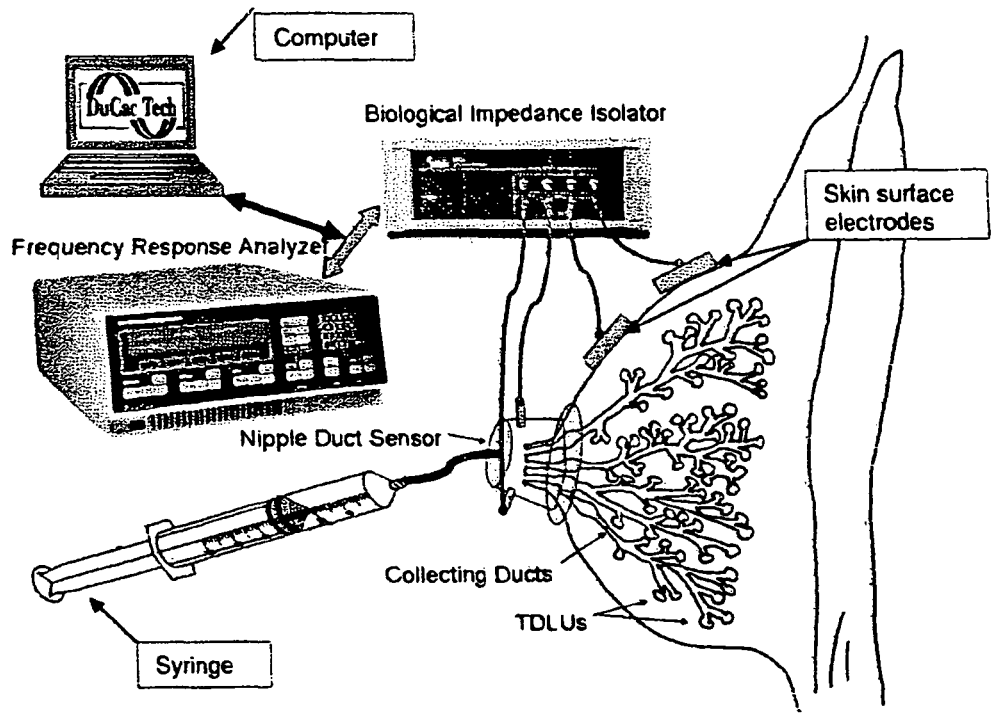
FIG. 7 illustrates an embodiment of the measurement system for determining subepithelial impedance.

One embodiment of the present invention is illustrated in FIG. 7. The figure illustrates the system used for making ductal epithelial impedance and Zsub measurements described above. Electrical contact with the ductal epithelium was established non-invasively and pain-free (as reported by 400 patients already tested), using a the specially designed nipple duct sensor illustrated in this figure and in FIG. 4, filled with physiological saline, which establishes electrical contact between the nipple sensor electrode and ductal epithelium across the duct opening. Skin impedance was reduced to <3,000 ohm-cm$^2$ using sonopheresis as described above and keratin plugs were removed from the nipple using a dekeratinizing agent to open up the duct ostia. Measurements were made between the nipple sensor and low offset Ag—AgCl skin surface electrodes. Transepithelial potential (TEP) and DEIS measurements were obtained over a frequency range of 0.1 Hz to 60 KHz and processed using a frequency response analyzer and sine-wave correlation using a tetrapolar electrode technique. Data was collected using ZPlot and analyzed using ZView (Scribner Associates, Inc.). Each of 4 quadrants was measured in every patient. All electrical connections to the patient were made through a Biological Impedance Isolator (Solarton 1294, Farnborough, UK) in compliance with IEC-60101 electrical safety standards. A laptop computer (DuCac Tech) was used to control the FRA, biological impedance analyzer, and to analyze the data.

In an alternative embodiment, impedance data for estimation of percent mammographic breast density and/or breast cancer risk assessment can be obtained using a single frequency or two or multiple frequency device, but fewer than the numerous frequencies used to obtain full spectral data as reported above. For example, it can be suitable to obtain phase and impedance measurements at one or two frequencies. Furthermore, the system and method can be used with or without sonopheresis or spiked electrodes as circumstances dictate. Suitable sonophoresis equipment is available commercially as described above and spiked or microneedle electrodes are also available for example from Silex Microsystems Inc., Boston, Mass. (see also Characterization of Micromachined Spiked Biopotential Electrodes, P. Griss et al., IEEE Trans. Biomed. Eng., 49, 6, 597-604 (June 2002); U.S. Pat. No. 7,050,847; and US 2007/0265512). Preferably the nipple sensor described and illustrated above is used to facilitate interrogation of the subepithelial parenchyma.

A further alternative embodiment of the invention would use 2 sensor electrodes in each quadrant or segment of the breast so that an impedance quotient (IQ) or resistance quotient (RQ) may be obtained. Since impedance is affected by age, weight, position in menstrual cycle etc., a quotient can be obtained in the individual patient by measuring Zsub or $Z_0$ at two locations in the same breast maintaining the same spacing between the skin sensing electrodes in relation to the nipple. Thus a measurement would be made of the impedance between the nipple sensor electrode and the inner skin sensor electrode and outer sensor electrode at approximately 3 cm and approximately 7 cm from the nipple using an extra skin sensor electrode added to the configuration illustrated in FIG. 7. The quotient being measured in the same patient would be corrected for the other confounding factors such as age, weight, menstrual cycle and would give a resistivity or permittivity value for the breast parenchyma related to the risk that the patient will be found to have proliferative or pre-cancerous changes in the breast or breast cancer.

Devices for Use with the Present Invention

A number of variations are possible for devices to be used with the present invention. Further, as noted above, within a device design, there are a number of aspects that may be varied. These variations, and others, are described below.

One embodiment of a probe or other device for use in the present invention includes a plurality of miniaturized electrodes in recessed wells. Surface recording and initial electronic processing, such as filtering, may be performed by disposable commercially-available silicon chips. Each ECM solution or agent may be specific to the individual electrode and reservoir on the chip. Thus, for one measurement, a particular set of electrodes would be used. For another measurement, for example, at a different ionic concentration, a different set of electrodes would be used. While this produces some variations, as the electrodes for one measurement are not located at the same points as for another, this system provides generally reliable results.

An alternative approach is to use fewer electrodes and use a flow-through or microfluidic system to change solutions and drugs. Specifically, solutions or agents are changed by passing small amounts of electrical current to move solution or agent through channels and out through pores in the surface of the device. In this embodiment, the electrode remains in contact with the same region of the surface of the breast, thus eliminating region-to-region variation in measurement. This approach requires time for equilibration between different solutions. In detecting the presence of proliferative, abnormal pre-cancerous or cancerous breast tissue, a hand-held probe is provided for obtaining surface measurements at the skin. The probe may include electrodes for passing current as well as for measuring. An impedance measurement may be taken between the nipple cup electrode and the hand-held probe, between a nipple cup electrode and adhesive skin electrodes, between electrodes on a miniature ductoscope, between electrodes on a ductoscope and the skin surface electrodes, or may be taken between electrodes on the hand-held probe. After taking initial DC measurements, a wetting/permeabilizing agent may be introduced to reduce skin impedance. The agent may be introduced using a microfluidic approach, as described above, to move fluid to the surface of the electrodes. Alternatively, surface electrodes that just penetrate the stratum corneum may be used to decrease impedance.

Fluids for use with the present inventions could include various electrolyte solutions such as physiologic saline (e.g. Ringers) with or without pharmacological agents. One preferable electrolyte solution to infuse into the ductal system will represent a physiological Ringer solution. Typically this consists of NaCl 6 g, KCl 0.075 g, $CaCl_2$ 0.1 g, $NaHCO_3$ 0.1 g, and smaller concentrations of sodium hyper and hypophosphate at a physiological pH of 7.4. Other electrolyte solution may be used were the electrolyte comprises approximately 1% of the volume of the solute. Hypertonic or hypotonic solutions that are greater or less than 1% may be used in provocative testing of the epithelium and/or tumor. The concentration of Na, K and Cl will be adjusted under different conditions to evaluate the conductance and permeability of the epithelium. Different pharmacological agents such as amiloride (to block electrogenic sodium absorption), Forskolin (or similar drugs to raise cyclic-AMP) and hormones such as prolactin or estradiol can also be infused with the Ringer solution to examine the electrophysiological response of the epithelium and tumor to these agents. Similarly, the calcium concentration of the infusate will be varied to alter the tight junction permeability and measure the electrophysiological response of the epithelium to this manipulation. Dexamethasone may be infused to decrease the permeability of the tight junctions, and the electrophysiological response will be measured.

Although specific examples have been given of drugs and hormones that may be used in "challenge" testing of the epithelium and tumor, any agonist or antagonist of specific ionic transport, or tight-junctional integrity, known to be affected during carcinogenesis may be used, particularly when it is known to influence the electrophysiological properties of the epithelium or tumor.

Regardless of the configuration of the device, a signal is used to measure the ductal transepithelial potential by itself, or the transepithelial impedance or the subepithelial impedance. Measurements may then be combined to characterize the electrical properties of the epithelium associated with a proliferative and/or developing abnormality of the breast, and can be compared with uninvolved areas of the same or opposite breast. Surface electropotential measurements and impedance measurements are made to characterize the non-transepithelial electrical properties of the breast. These measurements involve DC potential measurements where the surface potential is referenced to an electrode that is not in contact directly or indirectly through an ECM, with the duct lumen. Impedance measurements are similarly made between surface electrodes or a surface electrode and a reference electrode not in contact directly or indirectly (through an ECM) with the ductal lumen. These measurements can be compared and combined with the transepithelial electrical measurements to further characterize the breast tissue.

Furthermore an understanding of the electrophysiological basis of the altered impedance or DC potential permits more accurate diagnosis. For example impedance or DC potential may increase or decrease because of several factors. Increased stromal density of the breast may alter its impedance. Additionally, a decrease in the potassium permeability of the epithelia around a developing malignancy would increase impedance and is likely associated with a developing malignancy. Additional information is obtained from the methods of the present invention by probing the tissue to different depths using spaced voltage-sensing electrodes. The use of electrophysiological, pharmacological and hormonal manipulations to alter DC potential and/or DC potential differentially in normal compared to proliferative, cancer-prone, pre-malignant or malignant tissue is another significant difference, which enhances the diagnostic accuracy of the present invention.

It should be noted that skin impedance is a particularly significant factor if it is so high that it obscures the underlying impedance signature of the ductal epithelium and breast parenchyma. However, it isn't possible to know beforehand whether or not there will be a significant change when the skin is treated with sonophoresis, therefore it is necessary to establish a "uniform" or standard condition in order to interpret test results. Sonophoresis removes noise from the diagnostic measurements, both open-circuit potential noise and skin impedance noise.

High skin impedance may obscure the "true" transepithelial impedance profile. Reduction of skin impedance can result in measurements that reveal the multiple impedance dispersions of the epithelium and breast parenchyma under the skin. Furthermore, the transepithelial voltage cannot be accurately estimated by reducing skin impedance alone, and an estimation of the transepithelial electrical signal (impedance or voltage) requires reference to the inside of the ductal epithelium when making surface measurements.

The embodiments described herein are described in reference to humans. However, cancers in non-humans may be also diagnosed with this approach and the present invention is also intended to have veterinary applications.

Furthermore, various aspects or embodiments of the present invention may include features such as:

A method to measure the parenchymal impedance properties of an organ by combining skin surface electrical measurements with a reference or working electrode, and/or the use of an electroconductive medium that makes direct or indirect electrical contact with the luminal surface of an epithelium;

The passage of a sine wave, square wave or other electrical signal shape to probe the sub-epithelial, especially parenchymal, properties of the organ under test;

Measurement of voltage amplitude, phase shift and other impedance properties of the sub-epithelial, especially parenchymal, tissue using a combination of a reference or working electrode that makes direct or indirect electrical contact with the luminal surface of an epithelium and a skin surface electrode;

Use of Zsub alone or in combination with other electrical or patient characteristics to estimate percent mammographic breast density of a single breast of an individual, or of both breasts of an individual and to compare such values at a given point in time or serially over a period of time in order to identify values and changes in those values that may be indicative of an abnormal condition in the breast;

Using impedance measurement in combination with information about the age, weight (or body mass index, BMI), breast size, the distance that one or more surface electrodes are placed from the nipple, day of menstrual cycle at the time of electrical property measurement (or menopausal status), parity and mammographic density, such factors that can influence the impedance of sub-epithelial, especially parenchymal, tissues of the breast in order to estimate the risk of cancer development when compared with a normal risk or control population;

The above electrode combination can be combined with any method that reduces the surface impedance of the skin so that the skin does not obscure the sub epithelial electrical properties of the tissues;

Alternatively, a high enough frequency signal may be used so that the dielectric properties of the surface skin or internal epithelium do not mask the subepithelial tissues;

The addition of a second surface electrode placed at a different distance from the nipple, in the same quadrant or segment, so that the sub epithelial (parenchymal) impedance or resistance quotient can be estimated for the underlying tissue by adjusting for the influence of factors other than risk (age, weight, menstrual cycle day) that affect the sub epithelial (parenchymal) impedance. (Quotient is the difference or the ratio of the impedance measured at two different locations in the same quadrant or segment of the breast at different distances from the nipple or working electrode). In the case of resistance the quotient would be similar to the relative resistivity ($\rho$) of the tissue, or in the case of admittance the relative permittivity ($\in$) adjusted for distance from the nipple and other factors affecting resistance or impedance. The relative resistivity or permittivity of the sub epithelial tissues can then be used to estimate risk;

The use of a frequency high enough (for example greater than about 5 KHz to about 10 KHz and typically about 50 KHz to about 60 KHz) to probe the intracellular and extracellular fluid compartment of the tissue and thus obtain information about both intercellular communication and paracellular conductance;

The addition of a second lower frequency measurement to probe the extracellular fluid compartment alone, with measurement of the voltage amplitude, phase shift and other impedance properties of the tissue using a combination of the reference or working electrode in 1) above that makes direct or indirect electrical contact with the luminal surface of an epithelium and a skin surface electrode;

Using the ratio of impedance measurements at a high and a low frequency ($Z_\infty/Z_0$) to estimate the distribution of fluid between the intracellular and extracellular compartment, and the intercellular communication of the tissue to estimate the risk of cancer;

Using the ratio $Z_{\infty a}/Z_{0a}$ adjusted for factors known influence the value of the ratio (i.e. age, weight (BMI), breast size, distance electrodes are placed from the nipple, day of menstrual cycle (or menopausal status), parity and mammographic density) to estimate the risk of cancer;

Although most cancers are of epithelial origin, stromal or non-epithelial elements are frequently altered and intercellular communication disrupted. Intercellular communication may be characterized as between stromal cells or between epithelial and stromal cells and such communication can be evaluated using approaches outlined as above and thereby applied to assessing risk of cancer in organs with epithelial and stromal elements such as stomach, bowel, prostate, ovary, cervix, uterus, bladder skin etc;

The various aspects or embodiments described above can be used individually or in combination to assess modulation of cancer or proliferative cell risk as well as response to preventative strategies using agents such as hormones, drugs, etc., generally referred to as chemoprevention, or other therapeutic modalities, including, for example, radiation, electroporation, gene therapy, etc.

The technology represented by the various embodiments of the present invention are unlikely to completely do away with the need for mammographic imaging as, for example, there will still be a need to accurately localize a cancer developing in a region of high density. However, Zsub or an estimate of breast density can be used to estimate risk for an individual patient to guide the both need and frequency of imaging such as mammograms, MRI, nuclear imaging, "challenge tests" etc. Furthermore, since breast density is a modifiable risk factor, i.e., it changes in response to risk factors and/or risk reduction strategies such as childbirth, diet, exercise and chemopreventative drugs, breast density can be used to evaluate increasing or decreasing risk in response to the introduction or elimination of a risk factor, or cancer prevention with drugs or other interventions. Additionally, measurement of Zsub can be particularly useful for individuals, especially younger individuals, for whom use of X-rays may present an increased risk, whereas electrical test measurements avoid such risk and may be repeated on a regular, multiple or serial basis to follow a course of treatment or merely changes with age and/or lifestyle.

Any range of numbers recited in the specification hereinabove or in the paragraphs and claims hereinafter, referring to various aspects of the invention, such as that representing a particular set of properties, units of measure, conditions, physical states or percentages, is intended to literally incorporate expressly herein by reference or otherwise, any number falling within such range, including any subset of numbers or ranges subsumed within any range so recited. Furthermore, the term "about" when used as a modifier for, or in conjunction with, a variable, characteristic or condition is intended to convey that the numbers, ranges, characteristics and conditions disclosed herein are flexible and that practice of the present invention by those skilled in the art using temperatures, frequencies, times, concentrations, amounts, contents, properties such as size, surface area, etc., that are outside of the range or different from a single value, will achieve the desired results as described in the application, namely, measuring electrophysiological properties as well as detecting electrophysiological changes in normal, pre-cancerous and cancerous tissue and epithelium, including parenchymal tissue, preferably, breast tissue in order to estimate percent mammographic breast density and/or assess the risk of a patient developing breast cancer or proliferative disease of the breast.

For purposes of the present invention the following terms shall have the indicated meaning:

Comprise or comprising: Throughout the entire specification, including the claims, the word "comprise" and variations of the word, such as "comprising" and "comprises," as well as "have," "having," "includes," "include" and "including," and variations thereof, means that the named steps, elements or materials to which it refers are essential, but other steps, elements or materials may be added and still form a construct with the scope of the claim or disclosure. When recited in describing the invention and in a claim, it means that the invention and what is claimed is considered to what follows and potentially more. These terms, particularly when applied to claims, are inclusive or open-ended and do not exclude additional, unrecited elements or methods steps.

Consisting essentially of: In the present context, "consisting essentially of" is meant to exclude any element or combination of elements as well as any amount of any element or combination of elements that would alter the basic and novel characteristics of the invention. Thus, by way of example and not limitation, estimation of percent mammographic breast density and/or breast cancer risk assessment that did not take into account sub-epithelial impedance would be excluded.

Substantially: Unless otherwise defined with respect to a specific property, characteristic or variable, the term "substantially" as applied to any criteria, such as a property, characteristic or variable, means to meet the stated criteria in such measure such that one skilled in the art would understand that the benefit to be achieved, or the condition or property value desired is met.

All documents described herein are incorporated by reference herein, including any patent applications and/or testing procedures. The principles, preferred embodiments, and modes of operation of the present invention have been described in the foregoing specification.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the various aspects or embodiments of the present invention as set forth in the application and the appended claims.

REFERENCES CITED HEREINABOVE
INCLUDE THE FOLLOWING

American College of Radiology. Breast Imaging Reporting and Data System (BIRADS) (1993).
Blend, R., et al. Eur J Cancer Prev 4 (1995): 293-98.
Boone, J., et al. Med Phys 33 (2006): 2185.
Boyd, N. F., et al. N. Engl. J Med 356.3 (2007): 227-36
Buist, D. S., et al. Cancer Epidemiol Biomarkers Prev 15 (2006): 2303-06.
Buist, D. S., et al. J Natl Cancer Inst 96 (2004): 1432-40.
Byng, J. W., et al. Phys Med Biol 39 (1994): 1629-38
Caldwell, C. B., et al. Phys Med Biol 35 (1990): 235-47.
Carney, P. A., et al. Ann Intern Med 138 (2003): 168-75.
Chang, Y. H., et al. Acad Radiol 9 (2002): 899-905.
Chen, B., et al. Med Phys 29 (2002): 755-70.
Ding, J., et al. Cancer Epidemiol Biomarkers Prev 17 (2008): 1074-81.
Duric, N., et al. Med Phys 34.2 (2007): 773-85.
Glide, C., et al. Med Phys 34 (2007): 744-53.
Glide-Hurst, C. K., et al. Medical Physics 34 (2007): 4491-98.
Goodwin, P. J., et al. Am J Epidemiol 127 (1988): 1097-108.
Graham, S. J., et al. Br J Cancer 73 (1996): 162-68.
Gram, I. T., et al. Breast Cancer Res 7 (2005): R854-R861.
Hartman, Keith et al. IWDM 2008. Ed. E. A. Krupinski (Ed.). Berlin Heidelberg Springer-Verlag, 2008. 33-39.
Highnam, R. P., et al. Mammographic Image Processing (1999).
Huo, Z., et al. Med Phys 27 (2000): 4-12.
Karssemeijer, N. Phys Med Biol 43 (1998): 365-78.
Kaufhold, J., et al. Med Phys 29 (2002): 1867-80.
Khan, Q. J., et al. J Clin Oncol 24 (2006): 1011.
Klifa, C., et al. IEMBS '04: 26th Annual International Conference of the IEEE: San Francisco, Calif.; 1-4 Sep. 2004 1 (2004): 1667-70.
Kopans, D. B. Radiology 246.2 (2008): 348-53.
Lee, N. A., et al. AJR Am J Roentgenol 168 (1997): 501-06.
Li, H., et al. Acad Radiol 12 (2005): 863-73.
Li, H., et al. Med Phys 31 (2004): 549-55.
Magnin, I. E., et al. Optical Eng 25 (1986): 780-84.
Martin, K. E., et al. Radiology 240 (2006): 656-65.
McCormack, V. A., et al. Cancer Epidemiol Biomarkers Prev 16 (2007): 1148-54.
Megalooikonomou, V., et al. Proceedings of SPIE Medical Imaging 2007: Computer-Aided Diagnosis: 20 Feb. 2007; San Diego, Calif., USA 6514 (2007): 651421.
Miller, P., et al. Image and Vision Computing 10 (1992): 277-82.
Mitchell, G., et al. Cancer Res 66 (2006): 1866-72.
Niklason, L. T., et al. Radiology 205 (1997): 399-406.

Palomares, M. R., et al. Cancer Epidemiol Biomarkers Prev 15 (2006): 1324-30.
Pawluczyk, O., et al. Med Phys 30 (2003): 352-64.
Saftlas, A. F., et al. Epidemiol Rev 9 (1987): 146-74.
Shepherd, J. A., et al. Radiology 223 (2002): 554-57.
Sivaramakrishna, R., et al. Acad Radiol 8 (2001): 250-56.
Vachon, C. M., et al. Cancer Epidemiol Biomarkers Prev 11 (2002): 1382-88.
Warner, E., et al. Cancer Detect Prev 16 (1992): 67-72.
Wolfe, J. N. AJR Am J Roentgenol 126.6 (1976): 1130-37.
Wolf, J. N. Cancer 37 (1976): 2486-92.
Wolfe, J. N., et al. AJR Am J Roentgenol 148 (1987): 1087-92.
Wu, T., et al. Med Phys 30 (2003): 365-80.
Yaffe, Martin Breast Cancer Research 10.3 (2008): 209.
Zhou, C., et al. Med Phys 28 1056-69.

The invention claimed is:

1. A method for estimating a percent mammographic density (MD) of at least one breast of an individual, the breast comprising an overlying skin surface and nipple, the method comprising the following steps:
   (A) establishing a connection between a first electrode and subepithelial parenchymal tissue in the breast of the individual;
   (B) placing at least one second electrode in contact with the skin surface of the breast proximate the subepithelial tissue at a fixed distance from the nipple of the breast;
   (C) establishing at least one electrical signal having a frequency between the first and second electrodes;
   (D) measuring the subepithelial impedance (Zsub) at at least one frequency between the first and second electrodes; and
   (E) calculating an estimate of percent mammographic density of the breast according to an algorithm defined by an equation relating Zsub to mammographic breast density wherein values of mammographic breast density used to determine the algorithm have been estimated or calculated according to at least one method independent of steps (A) through (D).

2. The method according to claim 1 wherein the algorithm includes variables associated with (i) characteristics of the individual; (ii) conditions under which the electrical measurement are made; or (iii) both (i) and (ii).

3. The method according to claim 2 wherein the variables are selected from the group consisting of the individual's age, body mass index, weight, parity, whether such individual is a premenopausal female, whether such individual is a post-menopausal female, where a female individual is in her menstrual cycle, and distance from the nipple that the skin surface electrode is placed.

4. The method according to claim 1 wherein the independent method for estimating or calculating breast density is based on images selected from the group consisting of X-rays, ultrasound and magnetic resonance imaging (MRI).

5. The method according to claim 4 wherein the method is based on X-ray images selected from the group consisting of: the Wolfe Pattern; Six Category Classification; BI-RADS; ACR BI-RADS; planimetry; image digitization; interactive threshold of digitized X-ray images; texture measurement of X-ray images; computer-calculated image texture measurements; computed tomography (CT) imaging; breast tomosynthesis; dual-energy X-ray absorptiometry; and digital mammography.

6. The method according to claim 1 wherein the algorithm is selected from the group consisting of:

$$MD = 141.788 + (-0.716*age) + (-1.113*BMI) + (-0.199*Zsub); \quad (I)$$

$$MDpmw = 127.770 + (-1.339*BMI) + (-0.259*Zsub); \quad \text{and} \quad (II)$$

$$MDpstmw = 127.178 + (-0.874*Age) + (-0.219*Zsub); \quad (III)$$

wherein the symbol * indicates multiplication of the terms preceding and following the symbol; BMI=body mass index calculated as (Wt*703)/Height$^2$(inches$^2$)), or (Wt*4.88/Height$^2$(ft$^2$)), where Wt is in pounds; Zsub is expressed in ohms; age is expressed in years; MDpmw=mammographic density for pre-menopausal women;
MDpstmw=mammographic density for post-menopausal women.

7. The method according to claim 1 wherein Zsub is adjusted for the distance that the electrode is from the nipple (ADJZsub) according to the equation:

$$ADJZsub = Zsub_M/Zsub_{DFN} \text{ (where subscript } M=\text{measured); and}$$

$$Zsub_{DFN} = 169.512 + (6.668*DFN), \text{ where } DFN=\text{distance of the electrode from the nipple in cm.}$$

8. The method according to claim 1 wherein Zsub is adjusted for the distance that the electrode is from the nipple (ADJZsub) and the algorithm is selected from the group consisting of:

$$MDpmw = 131.936 + (-1.444*BMI) + (-54.752*ADJZsub) \quad (I)$$

or $$MDpstmw = 120.178 + (-0.869*Age) + (-39.179*ADJZsub); \quad (II)$$

wherein
MDpmw=mammographic density for pre-menopausal women;
MDpstmw=mammographic density for post-menopausal women;
$ADJZsub = Zsub_M/Zsub_{DFN}$ (where subscript M=measured); and
$Zsub_{DFN} = 169.512 + (6.668*DFN)$, where DFN=distance of the electrode from the nipple in cm.

9. A method for assessing the risk that a substantially asymptomatic female patient will be found to have proliferative or pre-cancerous changes in the breast, or may be at subsequent risk for the development of pre-cancerous or cancerous changes, said method comprising the following steps:
   (A) establishing a connection between a first electrode and subepithelial parenchymal tissue in the breast of the patient;
   (B) placing at least one second electrode in contact with the skin surface of the breast proximate the subepithelial tissue at a fixed distance from the nipple of the breast;
   (C) establishing at least one electrical signal having a frequency between the first and second electrodes;
   (D) measuring the subepithelial impedance at at least one frequency between the first and second electrode;
   (E) obtaining an estimate of subepithelial impedance ($Zsub_e$) of parenchymal breast tissue for the patient according to variables pertaining to the patient based on the following equation:

$$Zsube = 107.753 + (1.083*Age) + (-1.074*Breast Density) + (3.196*Body Mass Index);$$

wherein Age is measured in years; Breast Density is expressed in % and is estimated from the appearance of the breast(s) on a mammogram; and Body Mass Index, BMI, is defined as:

Wt (lbs)*703)/Height$^2$(inches$^2$), or

Wt (lbs)*4.88/Height$^2$(ft$^2$);

(F) obtaining at least one measured value of subepithelial impedance ($Zsub_m$) of parenchymal breast tissue for the patient; and (G) calculating a value for the ratio of $Zsub_m/Zsub_e$;

wherein there is a statistically significant increased risk that the female patient will be found to have breast cancer or be at increased risk of developing breast cancer provided that the ratio of $Zsub_m/Zsub_e$ is less than about 0.8 or greater than about 1.2.

10. A computer-readable medium having computer-executable instructions for performing a method for assessing the risk that a substantially asymptomatic female patient will be found to have breast cancer or be at increased risk of developing breast cancer, or may be at subsequent risk for the development of pre-cancerous or cancerous changes, the method comprising the following steps:

(A) establishing a connection between a first electrode and subepithelial parenchymal tissue in the breast of the patient;

(B) placing at least one second electrode in contact with the skin surface of the breast proximate the subepithelial tissue at a fixed distance from the nipple of the breast;

(C) establishing at least one electrical signal having a frequency between the first and second electrodes;

(D) measuring the subepithelial impedance at at least one frequency between the first and second electrode;

(E) calculating an estimate of subepithelial impedance ($Zsub_e$) of parenchymal breast tissue for the patient according to input values for variables pertaining to the patient based on the following equation:

$$Zsub_e=107.753+(1.083*Age)+(-1.074*Breast\ Density)+(3.196*Body\ Mass\ Index);$$

wherein Age is measured in years; Breast Density is expressed in % and is estimated from the appearance of the breast(s) on a mammogram; and Body Mass Index, BMI, is defined as:

Wt (lbs)*703)/Height$^2$(inches$^2$), or

Wt (lbs)*4.88/Height$^2$(ft$^2$);

(F) obtaining at least one measured value of subepithelial impedance ($Zsub_m$) of parenchymal breast tissue for the patient; and (G) calculating a value for the ratio of $Zsub_m/Zsub_e$;

wherein there is a statistically significant increased risk that the female patient will be found to have breast cancer provided that the ratio of $Zsub_m/Zsub_e$ is less than about 0.8 or greater than about 1.2.

11. A computer-readable medium having computer-executable instructions for performing a method for estimating the percent mammographic density (MD) of at least one breast of an individual, the breast comprising an overlying skin surface and nipple, the method comprising the following steps:

(A) establishing a connection between a first electrode and subepithelial parenchymal tissue in the breast of the individual;

(B) placing at least one second electrode in contact with the skin surface of the breast proximate the subepithelial tissue at a fixed distance from the nipple of the breast;

(C) establishing at least one electrical signal having a frequency between the first and second electrodes;

(D) measuring the subepithelial impedance (Zsub) at at least one frequency between the first and second electrode;

(E) calculating an estimate of the density of the breast according to an algorithm defined by an equation relating Zsub to mammographic breast density wherein mammographic breast density that was used to determine the algorithm has been estimated or calculated according to at least one method independent of steps (A) through (D).

12. The method according to claim 11 wherein the algorithm is selected from the group consisting of:

$$MD=141.788+(-0.716*age)+(-1.113*BMI)+(-0.199*Zsub); \quad (I)$$

$$MDpmw=127.770+(-1.339*BMI)+(-0.259*Zsub); \quad (II)$$

and $$MDpstmw=127.178+(-0.874*Age)+(-0.219*Zsub); \quad (III)$$

wherein the symbol * indicates multiplication of the terms preceding and following the symbol; BMI=body mass index calculated as (Wt*703)/Height$^2$(inches$^2$)), or (Wt*4.88/Height$^2$(ft$^2$)), where Wt is in pounds; Zsub is expressed in ohms; age is expressed in years; MDpmw=mammographic density for pre-menopausal women; MDpstmw=mammographic density for post-menopausal women.

13. The method according to claim 11 wherein Zsub is adjusted for the distance that the electrode is from the nipple (ADJZsub) according to the equation:

$$ADJZsub=Zsub_M/Zsub_{DFN}\ (where\ subscript\ M=measured);\ and$$

$$Zsub_{DFN}=169.512+(6.668*DFN),\ where\ DFN=distance\ of\ the\ electrode\ from\ the\ nipple\ in\ cm.$$

14. The method according to claim 11 wherein Zsub is adjusted for the distance that the electrode is from the nipple (ADJZsub) and the algorithm is selected from the group consisting of:

$$MDpmw=131.936+(-1.444*BMI)+(-54.752*ADJZsub) \quad (I)$$

or $$MDpstmw=120.178+(-0.869*Age)+(-39.179*ADJZsub); \quad (II)$$

wherein

MDpmw=mammographic density for pre-menopausal women;

MDpstmw=mammographic density for post-menopausal women;

$ADJZsub=Zsub_M/Zsub_{DFN}$ (where subscript M=measured); and $Zsub_{DFN}=169.512+(6.668*DFN)$, where DFN=distance of the electrode from the nipple in cm.

* * * * *